(12) United States Patent
Lee et al.

(10) Patent No.: US 11,840,538 B2
(45) Date of Patent: Dec. 12, 2023

(54) HETEROCYCLIC COMPOUNDS AND ORGANIC LIGHT EMITTING DEVICE USING THE SAME

(71) Applicant: LG CHEM, LTD., Seoul (KR)

(72) Inventors: Jung Ha Lee, Daejeon (KR); Dong Hoon Lee, Daejeon (KR); Tae Yoon Park, Daejeon (KR); Seong Mi Cho, Daejeon (KR); Dong Uk Heo, Daejeon (KR); Min Woo Jung, Daejeon (KR)

(73) Assignee: LG Chem, Ltd., Seoul (KR)

( * ) Notice: Subject to any disclaimer, the term of this patent is extended or adjusted under 35 U.S.C. 154(b) by 407 days.

(21) Appl. No.: 16/621,210

(22) PCT Filed: Jul. 20, 2018

(86) PCT No.: PCT/KR2018/008232
§ 371 (c)(1),
(2) Date: Dec. 10, 2019

(87) PCT Pub. No.: WO2019/017730
PCT Pub. Date: Jan. 24, 2019

(65) Prior Publication Data
US 2020/0190069 A1 Jun. 18, 2020

(30) Foreign Application Priority Data

Jul. 20, 2017 (KR) .......... 10-2017-0092174
Jul. 19, 2018 (KR) .......... 10-2018-0084350

(51) Int. Cl.
*C07D 495/04* (2006.01)
*C07D 491/048* (2006.01)
(Continued)

(52) U.S. Cl.
CPC ....... *C07D 491/048* (2013.01); *C07D 209/82* (2013.01); *C07D 307/91* (2013.01);
(Continued)

(58) Field of Classification Search
None
See application file for complete search history.

(56) References Cited

U.S. PATENT DOCUMENTS 8,946,984 B2  2/2015  Tanabe et al.
8,951,647 B2  2/2015  Parham et al.
(Continued)

FOREIGN PATENT DOCUMENTS

CN  102077384  5/2011
CN  104370904  2/2015
(Continued)

*Primary Examiner* — Robert S Loewe
(74) *Attorney, Agent, or Firm* — Bryan Cave Leighton Paisner LLP

(57) ABSTRACT

Provided is a heterocyclic compound of Formula 1:

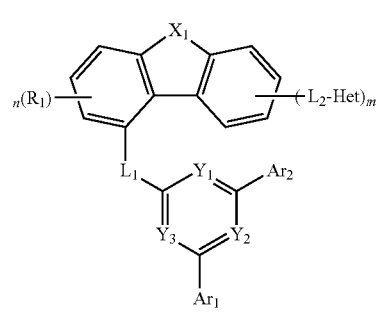

[Formula 1]

and an organic light emitting device comprising the same.

11 Claims, 1 Drawing Sheet

(51) Int. Cl.
    *C07D 209/82*     (2006.01)
    *C07D 307/91*     (2006.01)
    *C07D 333/52*     (2006.01)
    *C07D 407/14*     (2006.01)
    *C07D 409/14*     (2006.01)
    *C07D 471/04*     (2006.01)
    *C07D 487/04*     (2006.01)
    *C07D 413/14*     (2006.01)
    *C07D 417/14*     (2006.01)
    *H10K 85/60*     (2023.01)
    *H10K 50/11*     (2023.01)
    *H10K 50/12*     (2023.01)
    *H10K 50/16*     (2023.01)
    *H10K 50/17*     (2023.01)
    *H10K 101/10*     (2023.01)

(52) U.S. Cl.
    CPC ......... *C07D 333/52* (2013.01); *C07D 407/14* (2013.01); *C07D 409/14* (2013.01); *C07D 413/14* (2013.01); *C07D 417/14* (2013.01); *C07D 471/04* (2013.01); *C07D 487/04* (2013.01); *C07D 495/04* (2013.01); *H10K 85/615* (2023.02); *H10K 85/654* (2023.02); *H10K 85/657* (2023.02); *H10K 85/6572* (2023.02); *H10K 85/6574* (2023.02); *H10K 85/6576* (2023.02); *H10K 50/11* (2023.02); *H10K 50/12* (2023.02); *H10K 50/16* (2023.02); *H10K 50/166* (2023.02); *H10K 50/171* (2023.02); *H10K 2101/10* (2023.02)

(56) References Cited

U.S. PATENT DOCUMENTS

| | | | |
|---|---|---|---|
| 9,614,161 | B2 | 4/2017 | Park et al. |
| 9,865,822 | B2 | 1/2018 | Song et al. |
| 2004/0251816 | A1 | 12/2004 | Leo et al. |
| 2011/0095282 | A1 | 4/2011 | Pflumm et al. |
| 2011/0309343 | A1 | 12/2011 | Langer et al. |
| 2014/0077191 | A1 | 3/2014 | Mizutani et al. |
| 2014/0291645 | A1 | 10/2014 | Inoue et al. |
| 2014/0346483 | A1 | 11/2014 | Yu et al. |
| 2015/0207082 | A1 | 7/2015 | Dyatkin et al. |
| 2016/0093808 | A1 | 3/2016 | Adamovich et al. |
| 2016/0111657 | A1 | 4/2016 | Lee et al. |
| 2016/0181548 | A1 | 6/2016 | Parham et al. |
| 2016/0226001 | A1 | 8/2016 | Parham et al. |
| 2016/0276603 | A1 | 9/2016 | Beers et al. |
| 2016/0308142 | A1 | 10/2016 | Kim et al. |
| 2016/0329502 | A1 | 11/2016 | Dyatkin et al. |
| 2016/0351826 | A1 | 12/2016 | Kim et al. |
| 2017/0012216 | A1 | 1/2017 | Kim et al. |
| 2017/0025618 | A1 | 1/2017 | Zheng et al. |
| 2017/0054087 | A1 | 2/2017 | Zeng et al. |
| 2017/0179403 | A1 | 6/2017 | Kim et al. |
| 2017/0186965 | A1 | 6/2017 | Parham et al. |
| 2017/0186971 | A1 | 6/2017 | Kanamoto et al. |
| 2017/0200903 | A1 | 7/2017 | Park et al. |
| 2017/0207399 | A1 | 7/2017 | Parham et al. |
| 2017/0222157 | A1 | 8/2017 | Jatsch et al. |
| 2017/0237017 | A1 | 8/2017 | Parham et al. |
| 2018/0037546 | A1 | 2/2018 | Sugino et al. |
| 2018/0162843 | A1 | 6/2018 | Parham et al. |
| 2018/0166641 | A1 | 6/2018 | Inoue et al. |
| 2019/0165282 | A1 | 5/2019 | Parham et al. |
| 2020/0058877 | A1 | 2/2020 | Cha et al. |
| 2020/0144511 | A1 | 5/2020 | Bae et al. |
| 2020/0259098 | A1 | 8/2020 | Lee et al. |

FOREIGN PATENT DOCUMENTS

| | | |
|---|---|---|
| CN | 105189455 A | 12/2015 |
| CN | 105934436 A | 9/2016 |
| CN | 106459018 | 2/2017 |
| CN | 106565433 | 4/2017 |
| CN | 106661006 A | 5/2017 |
| CN | 108250189 A | 7/2018 |
| CN | 108884086 A | 11/2018 |
| CN | 108884087 A | 11/2018 |
| CN | 110268036 A | 9/2019 |
| CN | 110313078 A | 10/2019 |
| CN | 110869372 A | 3/2020 |
| CN | 111183204 A | 5/2020 |
| JP | 2013131518 | 7/2013 |
| JP | 5831654 | 12/2015 |
| JP | 6128119 | 5/2017 |
| JP | 2017098561 | 6/2017 |
| JP | 2017107992 | 6/2017 |
| KR | 10-20100007143 | 1/2010 |
| KR | 10-20100077675 | 7/2010 |
| KR | 10-20100118690 | 11/2010 |
| KR | 10-20120033017 | 4/2012 |
| KR | 10-20130036048 | 4/2013 |
| KR | 10-20130069431 | 6/2013 |
| KR | 10-20130073537 | 7/2013 |
| KR | 10-20140065863 | 5/2014 |
| KR | 10-20150054797 | 5/2015 |
| KR | 10-20150074603 | 7/2015 |
| KR | 10-20150084657 | 7/2015 |
| KR | 10-20150121394 | 10/2015 |
| KR | 10-20150129282 | 11/2015 |
| KR | 10-20150136942 | 12/2015 |
| KR | 10-20160026661 | 3/2016 |
| KR | 10-20160028524 | 3/2016 |
| KR | 1020160045507 A | 4/2016 |
| KR | 10-20170003502 | 1/2017 |
| KR | 10-20170039209 | 4/2017 |
| KR | 10-1857703 | 5/2018 |
| KR | 10-20180055698 | 5/2018 |
| KR | 10-2018-0068869 A | 6/2018 |
| KR | 10-20180133376 | 12/2018 |
| WO | 2003012890 | 2/2003 |
| WO | 2006128800 | 12/2006 |
| WO | 2009069442 | 6/2009 |
| WO | 2010015306 | 2/2010 |
| WO | 2010126270 | 11/2010 |
| WO | 2011126224 | 10/2011 |
| WO | 2011157790 | 12/2011 |
| WO | 2011158204 | 12/2011 |
| WO | 2013168534 | 11/2013 |
| WO | 2014042420 | 3/2014 |
| WO | 2014123369 | 8/2014 |
| WO | 2014178532 | 11/2014 |
| WO | 2015014434 | 2/2015 |
| WO | 2015036080 | 3/2015 |
| WO | 2015083974 | 6/2015 |
| WO | 2015169412 | 11/2015 |
| WO | 2016012075 | 1/2016 |
| WO | 2016013735 | 1/2016 |
| WO | 2016015810 | 2/2016 |
| WO | 2016023608 | 2/2016 |
| WO | 2016027938 | 2/2016 |
| WO | 2016129672 | 8/2016 |
| WO | 2016198144 | 12/2016 |
| WO | 2017016630 | 2/2017 |
| WO | 2017178311 | 10/2017 |

【FIG. 1】
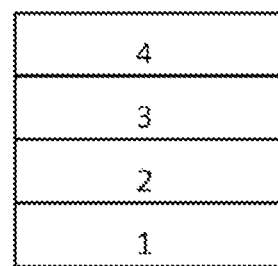
【FIG. 2】
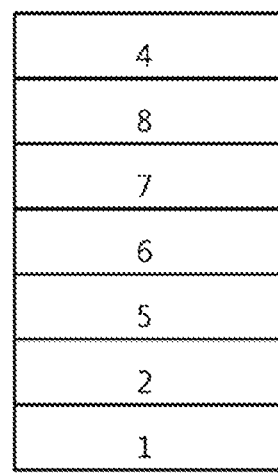

HETEROCYCLIC COMPOUNDS AND ORGANIC LIGHT EMITTING DEVICE USING THE SAME

CROSS-REFERENCE TO RELATED APPLICATIONS

This application is a National Stage Application of International Application. No. PCT/KR2018/008232 filed on. Jul. 20, 2018, which claims priority to and the benefit of Korean Patent Application No. 10-2017-0092174 filed on Jul. 20, 2017 and Korean Patent Application No. 10-2018-0084350 filed on Jul. 19, 2018 with the Korean Intellectual Property Office, the disclosures of which are incorporated herein by reference in their entirety.

TECHNICAL FIELD

The present invention relates to a novel heterocyclic compound and an organic light emitting device including the same.

BACKGROUND

In general, an organic light emitting phenomenon refers to a phenomenon where electrical energy is converted into light energy by using an organic material. The organic light emitting device using the organic light emitting phenomenon has characteristics such as a wide viewing angle, excellent contrast, a fast response time, and excellent luminance, driving voltage, and response speed, and thus many studies about it have proceeded.

The organic light emitting device generally has a structure which includes an anode, a cathode, and an organic material layer interposed between the anode and the cathode. The organic material layer can have a multilayered structure that includes different materials in order to enhance efficiency and stability of the organic light emitting device, and for example, the organic material layer can be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and the electrons meet each other, an exciton is formed, and light is emitted when the exciton falls to a ground state.

There is a continuing need for the development of new materials for the organic materials used in such organic light emitting devices.

PRIOR ART LITERATURE

Patent Literature (Patent Literature 0001) Korean Patent Laid-open Publication No. 10-2013-073537

DETAILED DESCRIPTION OF THE INVENTION

Technical Problem

It is an object of the present invention to provide a novel heterocyclic compound and an organic light emitting device including the same.

Technical Solution

In order to achieve the above object, the present invention provides a compound of the following Formula 1:

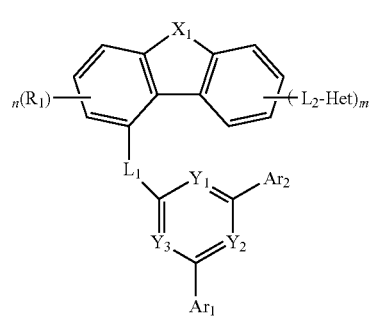

[Formula 1]

wherein in Formula 1 above:

$X_1$ is O or S;

$R_1$ is hydrogen or a substituted or unsubstituted $C_{1-60}$ alkyl;

$L_1$ and $L_2$ are each independently a direct bond or a substituted or unsubstituted $C_{6-60}$ arylene;

$Y_1$, $Y_2$, and $Y_3$ are each independently N or $CR_2$, provided that at least one of $Y_1$, $Y_2$, and $Y_3$ is N;

$R_2$ is hydrogen or a substituted or unsubstituted $C_{1-60}$ alkyl;

$Ar_1$ and $Ar_2$ are each independently a substituted or unsubstituted $C_{6-60}$ aryl or a substituted or unsubstituted $C_{5-60}$ heteroaryl containing at least one of N, O, and S, which can be combined with an adjacent $Y_1$, $Y_2$, or $Y_3$ to form a ring;

Het is a substituted or unsubstituted $C_{5-60}$ heteroaryl containing at least one N; and m and n are each independently 1 or 2.

The present invention also provides an organic light emitting device including a first electrode, a second electrode provided at a side opposite to the first electrode, and at least one organic material layer provided between the first electrode and the second electrode, wherein the at least one organic material layer includes the compound of the present invention described above.

Advantageous Effects

The compound of Formula 1 described above can be used as a material of an organic material layer of an organic light emitting device, and can allow improvement of the efficiency, low driving voltage, and/or improvement of the lifetime characteristic when applied to the organic light emitting device. In particular, the compound of Formula 1 can be used as a material for hole injection, hole transport, hole injection and transport, light emission, electron transport, or electron injection.

BRIEF DESCRIPTION OF DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, a light emitting layer 7, an electron transport layer 8, and a cathode 4.

DETAILED DESCRIPTION OF THE EMBODIMENTS

Hereinafter, the present invention will be described in more detail to help understanding of the present invention.

The present invention provides a compound of Formula 1 as follows.

A compound of the following Formula 1:

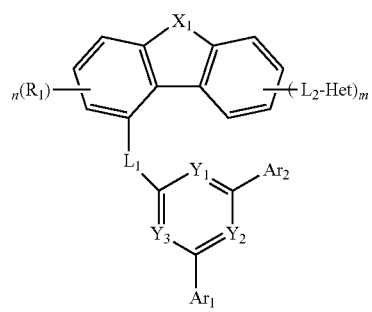

[Formula 1]

wherein in Formula 1 above:

$X_1$ is O or S;

$R_1$ is hydrogen or a substituted or unsubstituted $C_{1-60}$ alkyl;

$L_1$ and $L_2$ are each independently a direct bond or a substituted or unsubstituted $C_{6-60}$ arylene;

$Y_1$, $Y_2$, and $Y_3$ are each independently N or $CR_2$, provided that at least one of $Y_1$, $Y_2$, and $Y_3$ is N;

$R_2$ is hydrogen or a substituted or unsubstituted $C_{1-60}$ alkyl;

$Ar_1$ and $Ar_2$ are each independently a substituted or unsubstituted $C_{6-60}$ aryl or a substituted or unsubstituted $C_{5-60}$ heteroaryl containing at least one of N, O, and S, which can be combined with an adjacent $Y_1$, $Y_2$, or $Y_3$ to form a ring;

Het is a substituted or unsubstituted $C_{5-60}$ heteroaryl containing at least one N; and m and n are each independently 1 or 2.

In the present specification,

means a bond connected to another substituent group.

As used herein, the term "substituted or unsubstituted" means that substitution is performed with one or more substituent groups selected from the group consisting of deuterium, a halogen group, a nitrile group, a nitro group, a hydroxyl group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, or a heterocyclic group containing at least one of N, O, and S atoms, or there is no substituent group, or substitution is performed with a substituent group where two or more substituent groups of the exemplified substituent groups are linked or there is no substituent group. For example, the term "substituent group where two or more substituent groups are connected" can be a biphenyl group. That is, the biphenyl group can be an aryl group, or can be interpreted as a substituent group in which two phenyl groups are connected.

In the present specification, the number of carbon atoms in a carbonyl group not particularly limited, but is preferably 1 to 40. Specifically, the carbonyl group can be a compound having one of the following structures, but is not limited thereto:

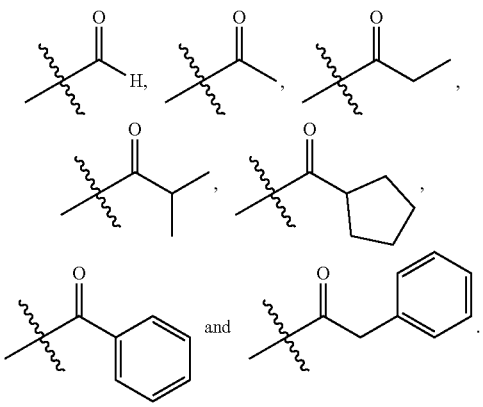

In the present specification, the ester group can have a structure in which oxygen of the ester group can be substituted by a straight-chain, branched-chain, or cyclic alkyl group having 1 to 25 carbon atoms, or an aryl group having 6 to 25 carbon atoms. Specifically, the ester group can be a compound having one of the following structures, but is not limited thereto:

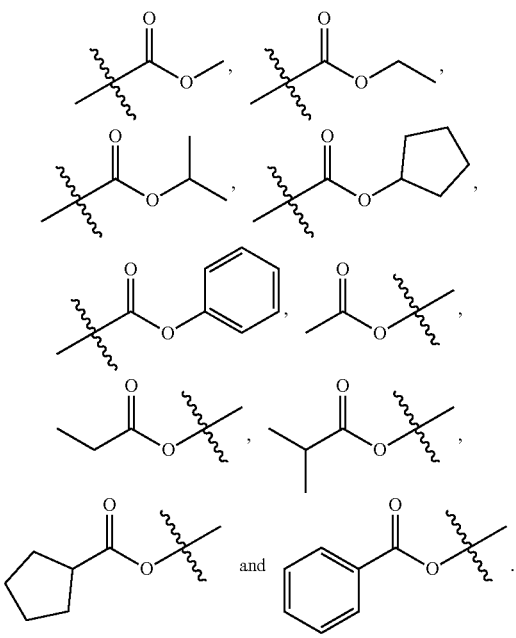

In the present specification, the number of carbon atoms in an imide group is not particularly limited, but is preferably 1 to 25. Specifically, the imide group can be a compound having one of the following structures, but is not limited thereto:

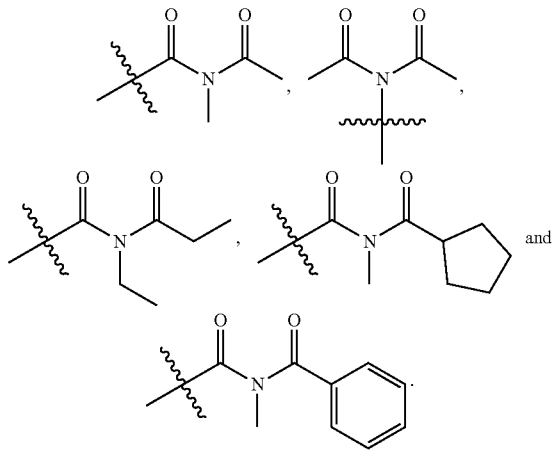

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes trimethylboron group, a triethylboron group, a t-butyldimethylboron group, a triphenylboron group, a phenylboron group, and the like, but is not limited thereto.

In the present specification, examples of a halogen group include fluorine, chlorine, bromine, and iodine.

In the present specification, the alkyl group can be a straight chain or a branched chain, and the number of carbon atoms thereof is not particularly limited, but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl, and the like, but are not limited thereto.

In the present specification, the alkenyl group can be a straight chain or a branched chain, and the number of carbon atoms thereof is not particularly limited, but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, the cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to still another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and can be a monocyclic aryl group or a polycyclic aryl group. According to one embodiment, the aryl group has 6 to 30 carbon atoms. According to another embodiment, the aryl group has 6 to 20 carbon atoms. The aryl group can a phenyl group, a biphenyl group, a terphenyl group, or the like as the monocyclic aryl group, but is not limited thereto. Examples of the polycyclic aryl group include a naphthyl group, an anthracenyl group, a phenanthryl group, a pyrenyl group, a perylenyl group, a chrycenyl group, a fluorenyl group, and the like, but are not limited thereto.

In the present specification, a fluorenyl group can be substituted, and two substituent groups can be combined with each other to form a spiro structure. In the case where the fluorenyl group is substituted,

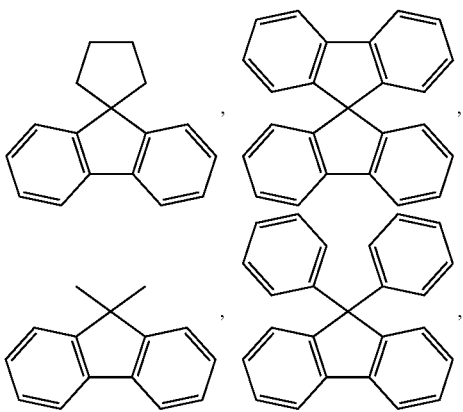

and the like can be formed. However, the structure is not limited thereto.

In the present specification, the heterocyclic group is a heterocyclic group containing at least one of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group, and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but is formed by combining two substituent groups. In the present specification, the aforementioned description of the heterocyclic group can be applied, except that the heterocycle is not a monovalent group but is formed by combining two substituent groups.

Preferably, the compound of Formula 1 can be any one selected from compounds of the following Formulas 2 to 6:

[Formula 2]

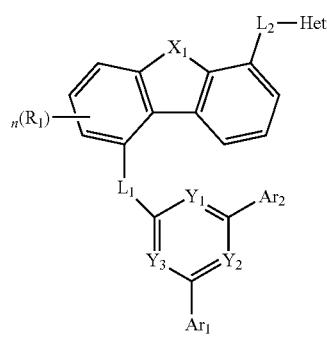

[Formula 3]

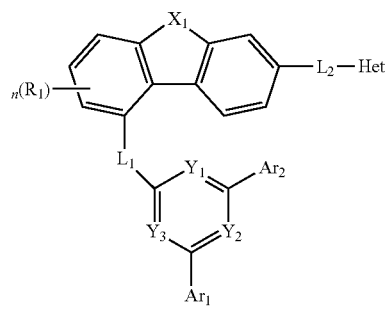

[Formula 4]

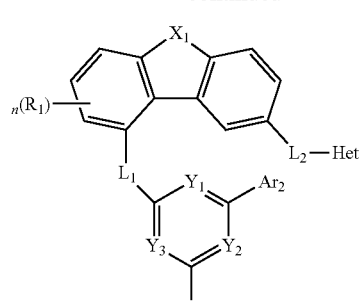

[Formula 5]

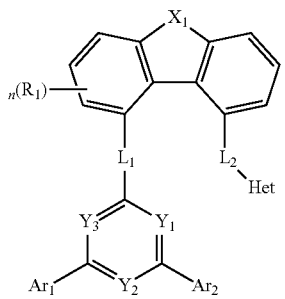

[Formula 6]

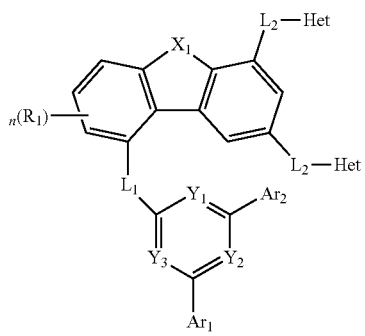

wherein in Formulas 2 to 6 above:

$X_1$, $L_1$, $L_2$, Het, $Y_1$, $Y_2$, $Y_3$, $R_1$, $Ar_1$, $Ar_2$, and n are as defined in Formula 1.

Further, more preferably, the compound of Formula 1 can be a compound of Formula 2, 4, or 6.

Further, preferably, the compound of Formula 1 can be any one selected from compounds of the following Formulas 7 to 11:

[Formula 7]

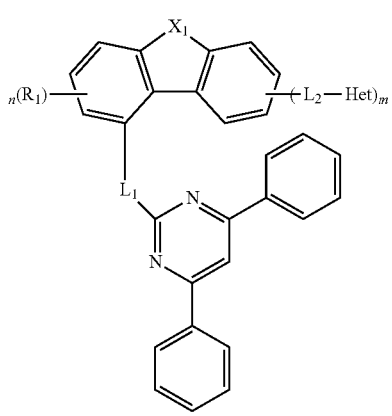

-continued

[Formula 8]

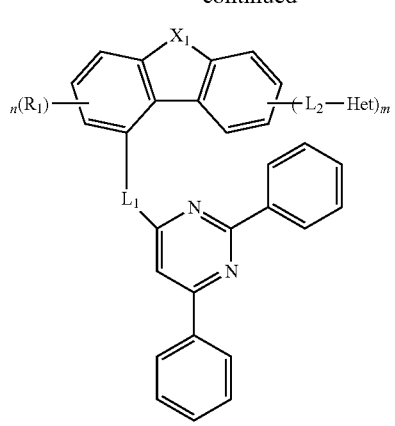

[Formula 9]

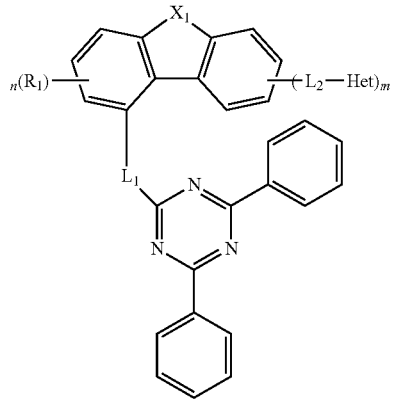

[Formula 10]

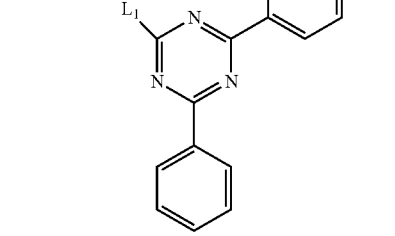

[Formula 11]

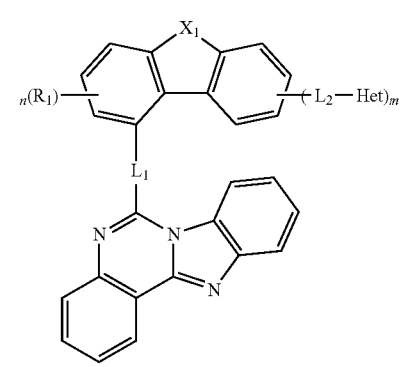

wherein in Formulas 7 to 11 above:
$X_1$, $L_1$, $L_2$, Het, $R_1$, n, and m are as defined above.

Preferably, $R_1$ can be hydrogen or a substituted or unsubstituted $C_{1-10}$ alkyl, more preferably hydrogen.

Preferably, in Formula 1, $L_1$ and $L_2$ are each independently a direct bond or

Preferably, in Formula 1, Het can be any one selected from compounds of the following formulas:

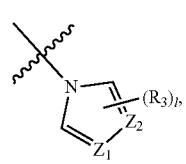

[1-1]

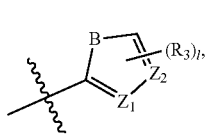

[1-2]

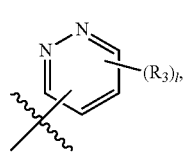

[1-3]

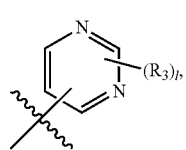

[1-4]

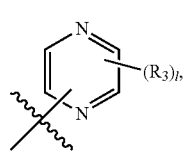

[1-5]

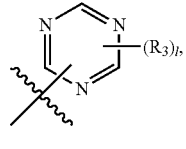

[1-6]

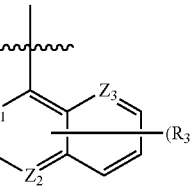

[1-7]

[1-8]
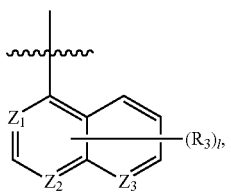

[1-9]
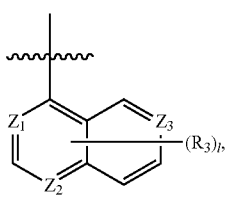

[1-10]
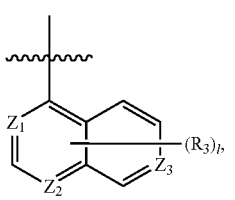

[1-11]
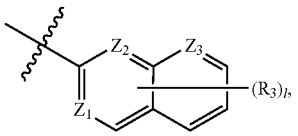

[1-12]
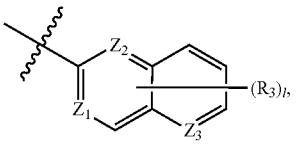

[1-13]
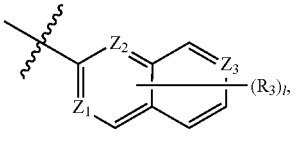

[1-14]
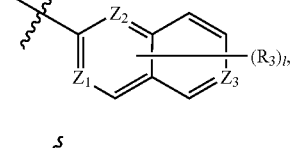

[1-15]
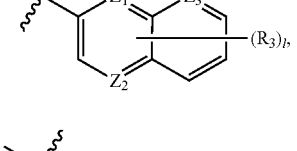

[1-16]
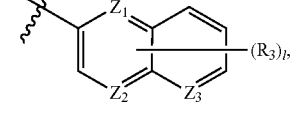

[1-17]
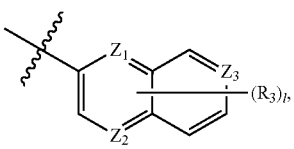

[1-18]
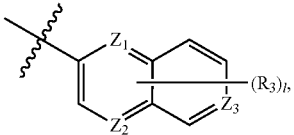

[1-19]
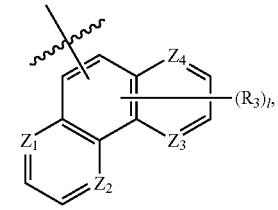

[1-20]
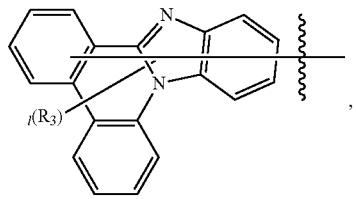

,

[1-21]
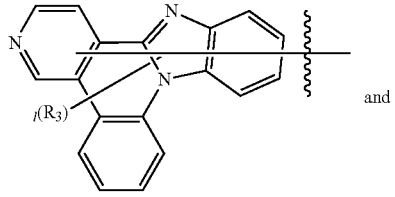

and

[1-22]
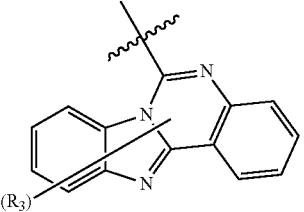

wherein in Formulas [1-1] to [1-22] above:

B is O or S;

$Z_1$, $Z_2$, $Z_3$, and $Z_4$ are each independently N or CH, provided that at least one of $Z_1$, $Z_2$, $Z_3$, and $Z_4$ in each formula is N;

each $R_3$ is independently hydrogen, a substituted or unsubstituted $C_{1-60}$ alkyl, a substituted or unsubstituted $C_{6-60}$ aryl, or a substituted or unsubstituted $C_{5-60}$ heteroaryl containing at least one of N, O, and S; and each l is independently 1 or 2.

Preferably, $R_3$ can be hydrogen or any one selected from the group consisting of compounds of the following formulas:

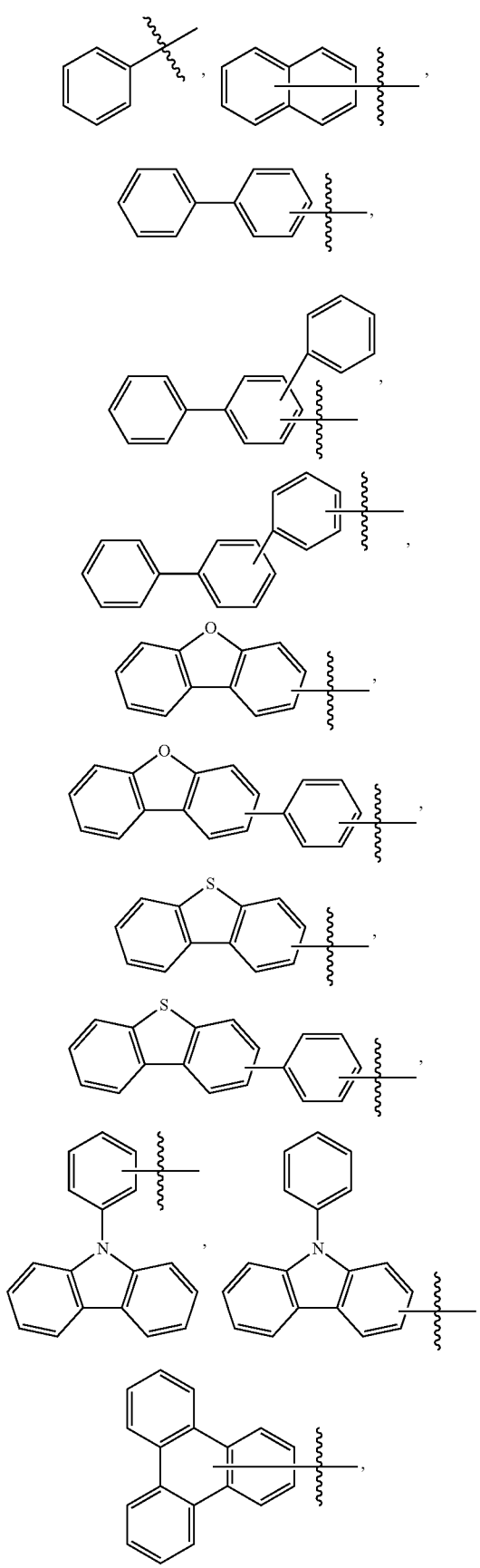
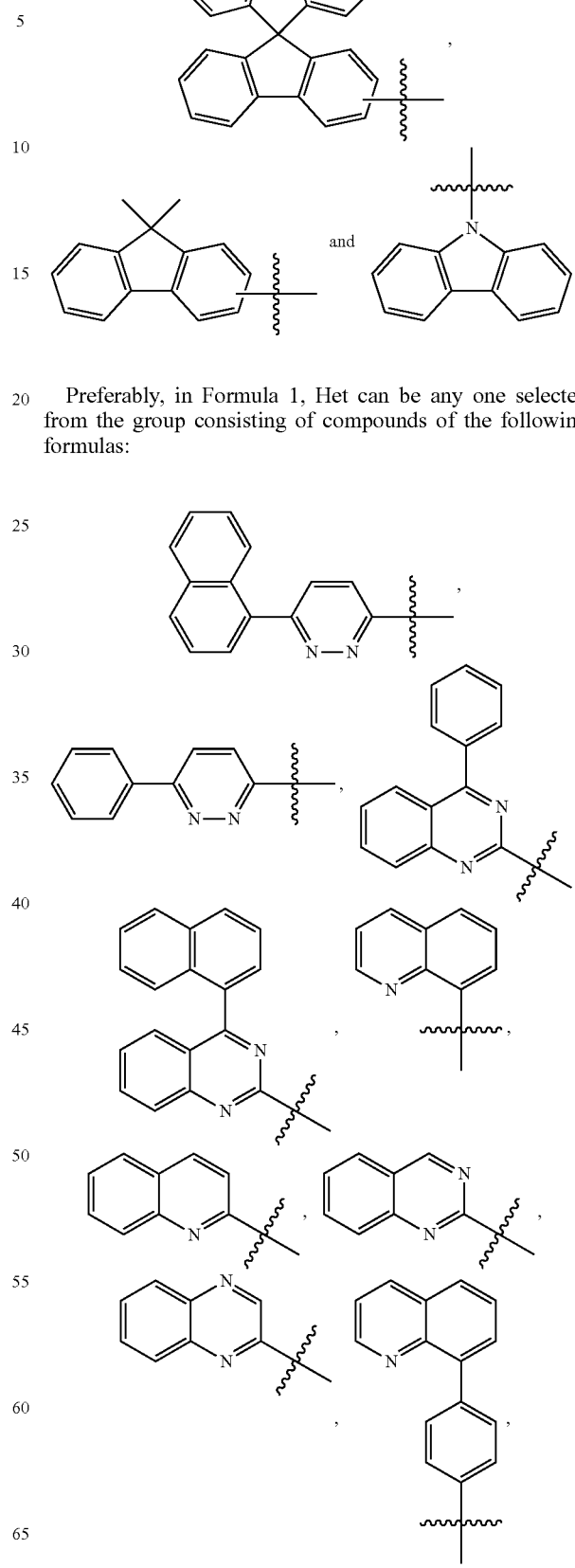
Preferably, in Formula 1, Het can be any one selected from the group consisting of compounds of the following formulas:

15
-continued
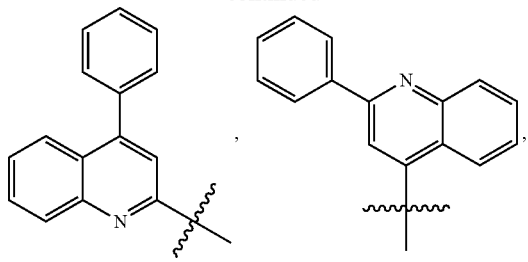
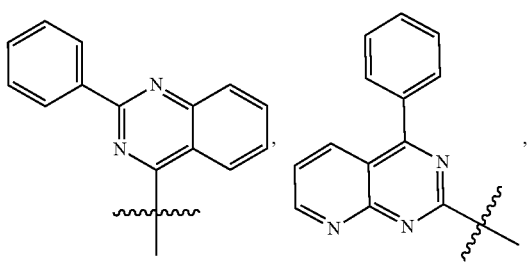
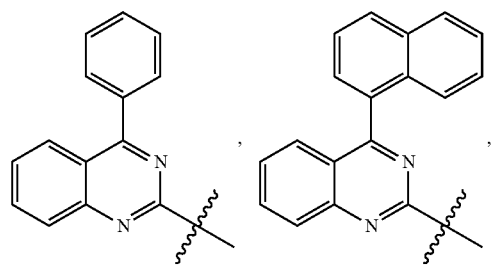
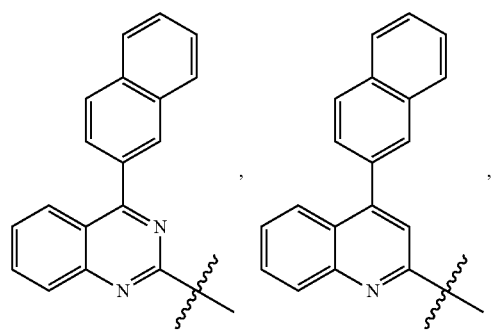
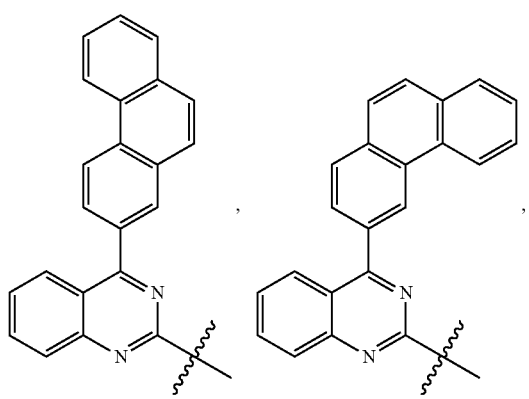
16
-continued
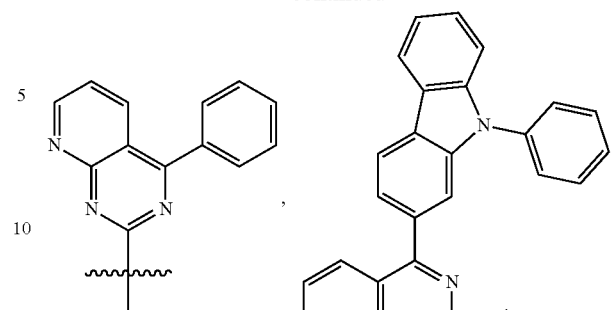
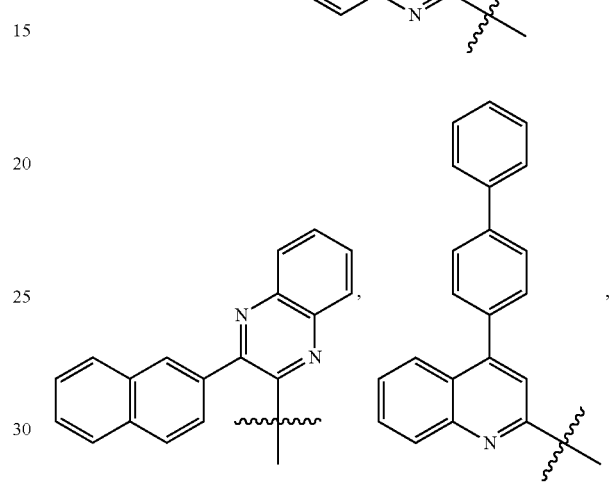
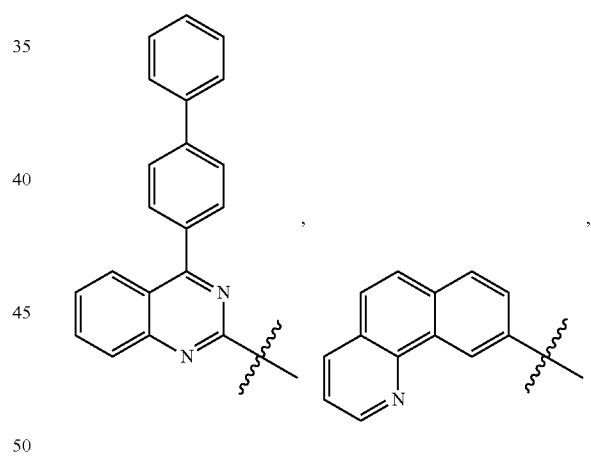
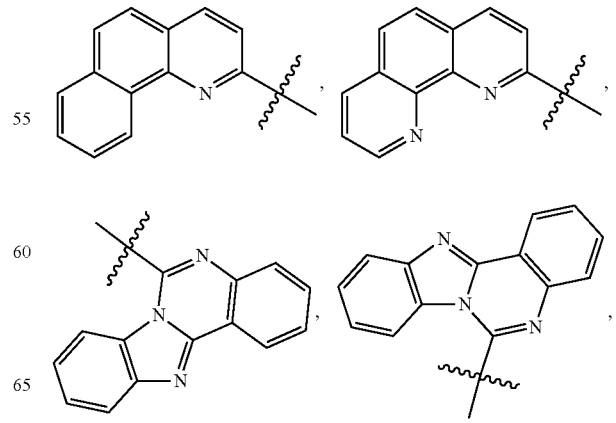

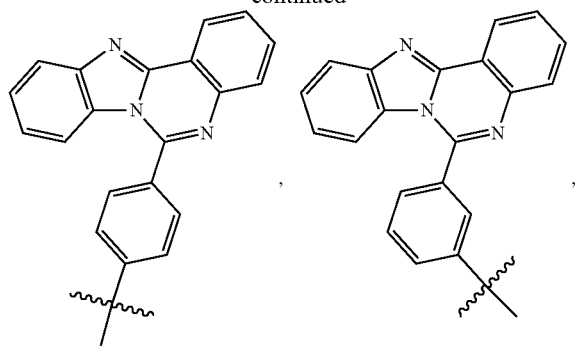
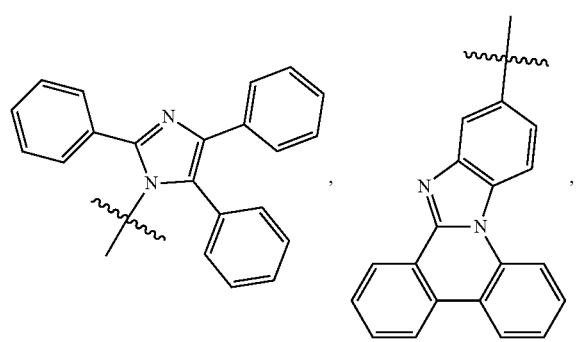
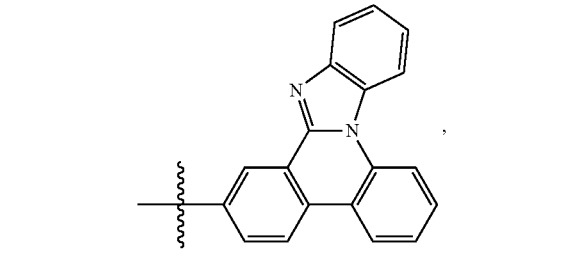
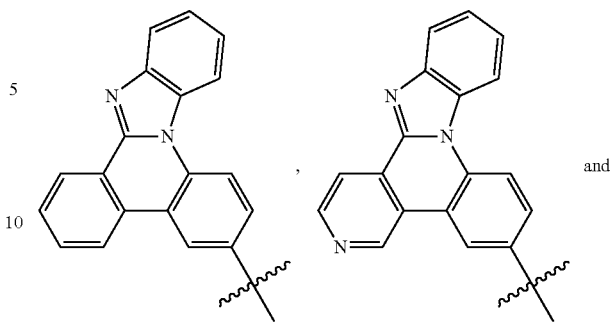
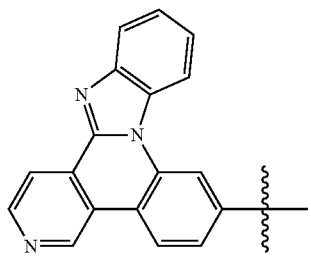
Preferably, the compound of Formula 1 can be any one selected from the group consisting of compounds of the following formulas:
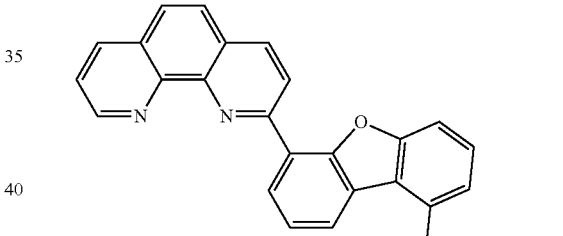
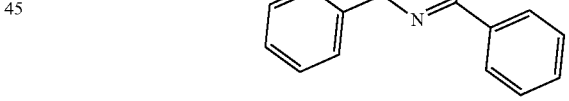
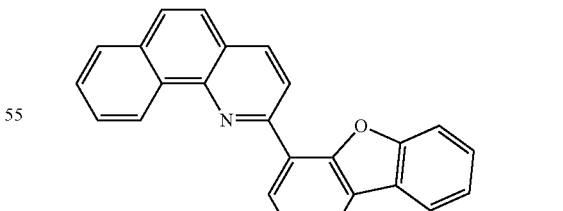
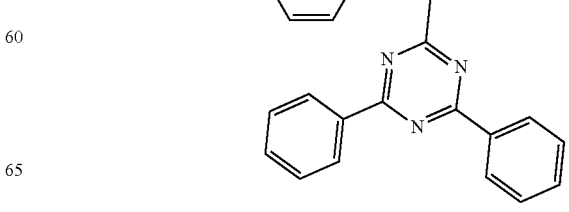

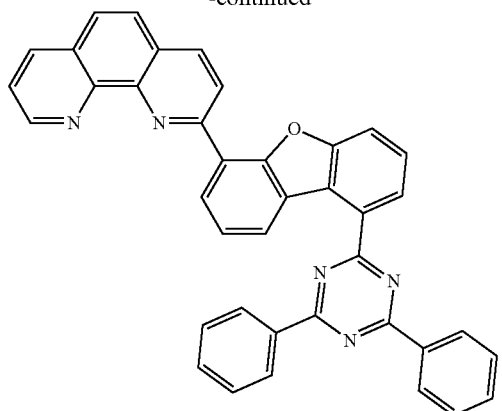
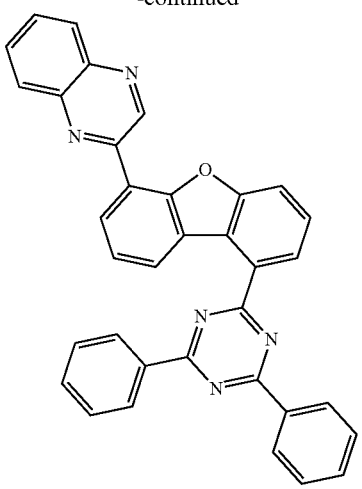
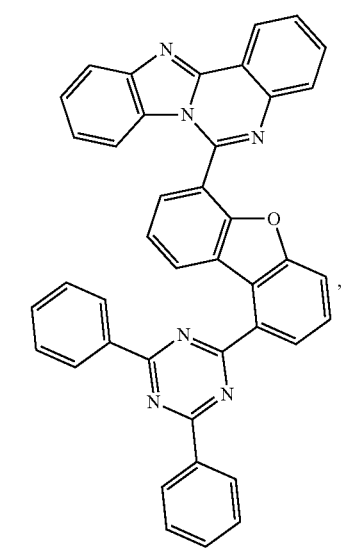
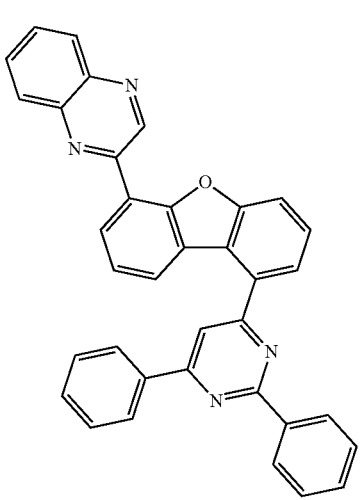
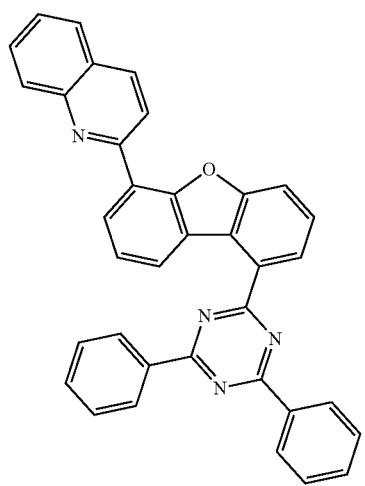
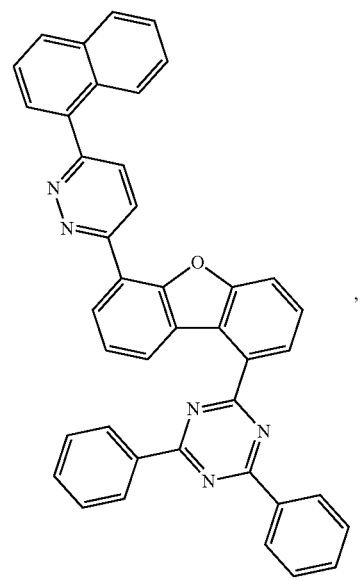

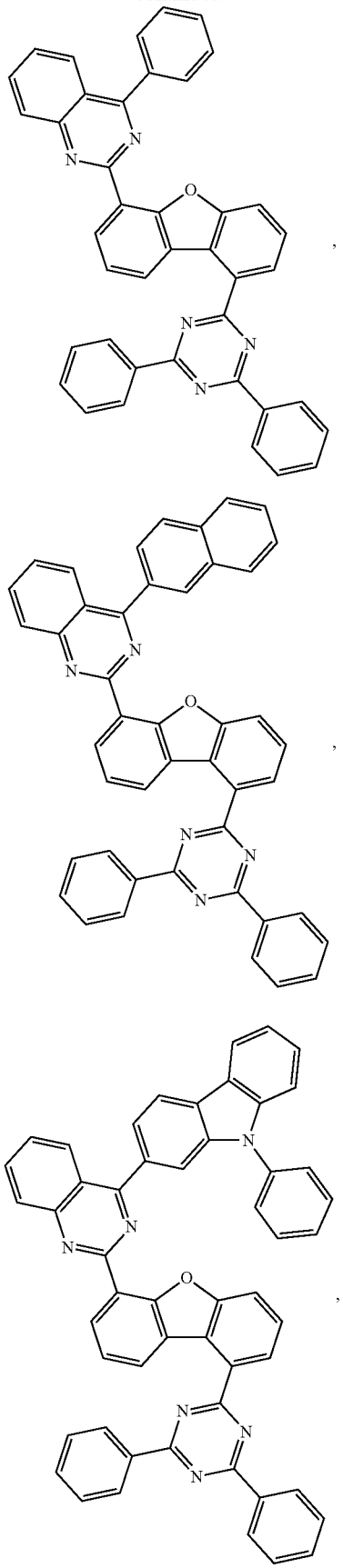

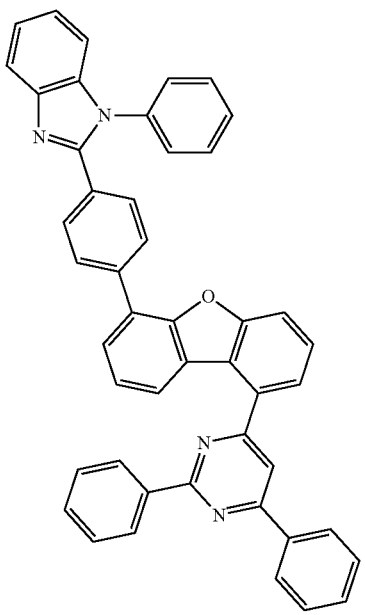
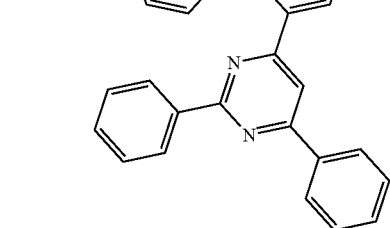
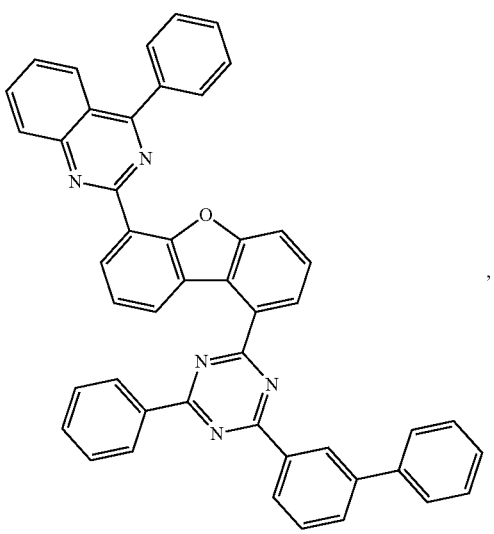
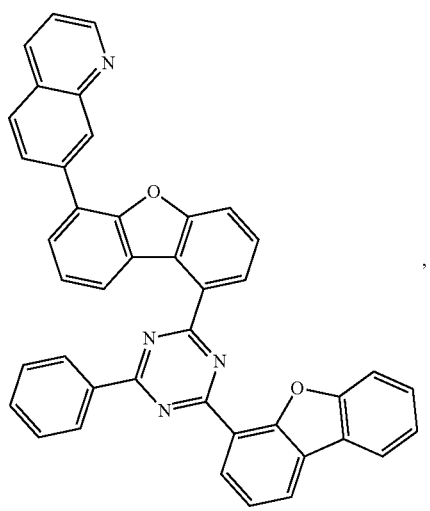
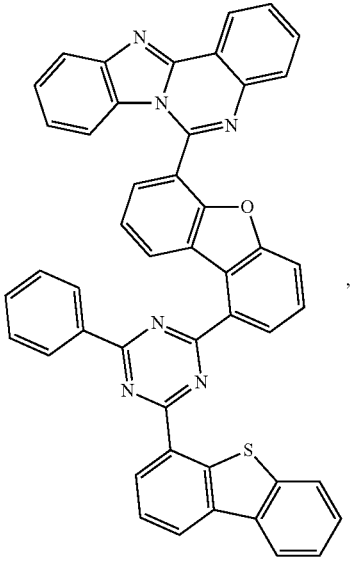
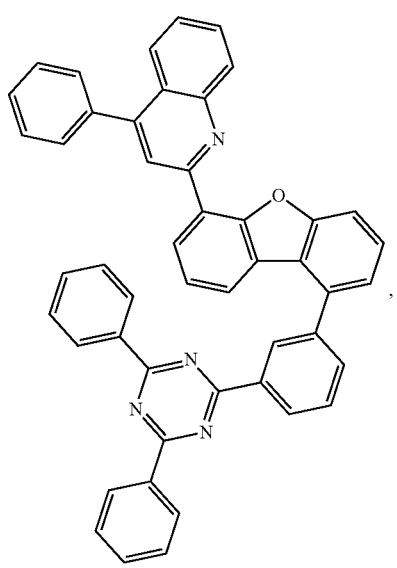
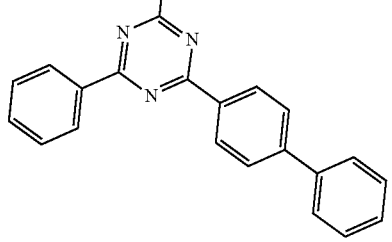

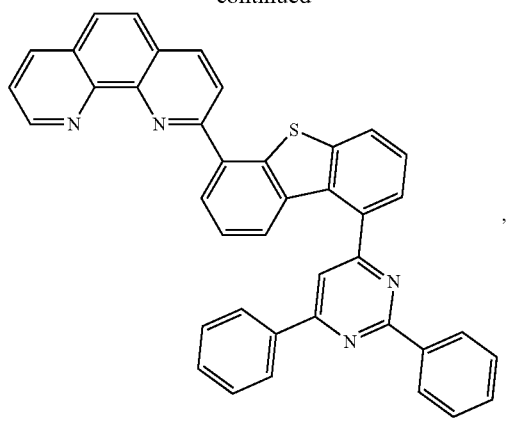
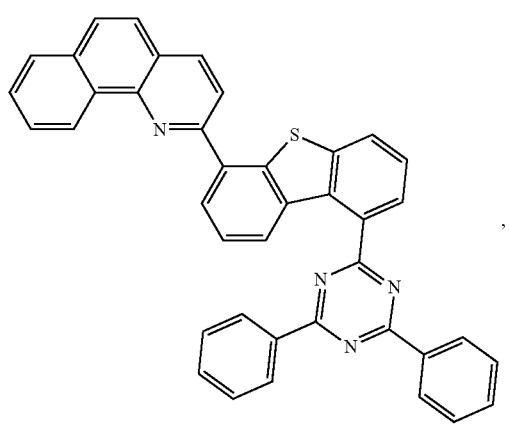
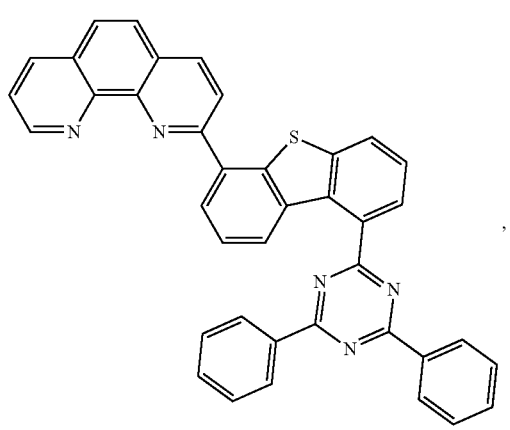
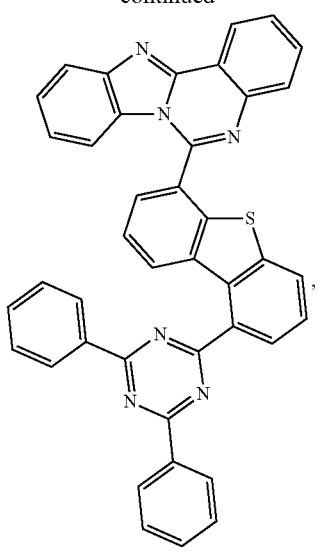
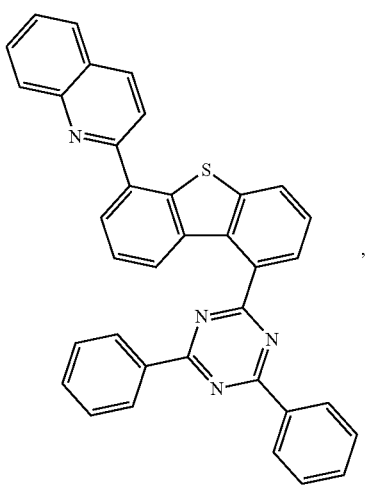
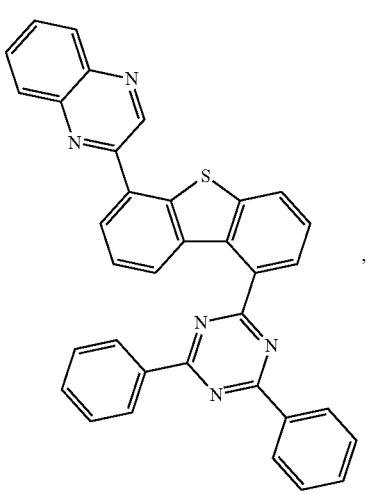

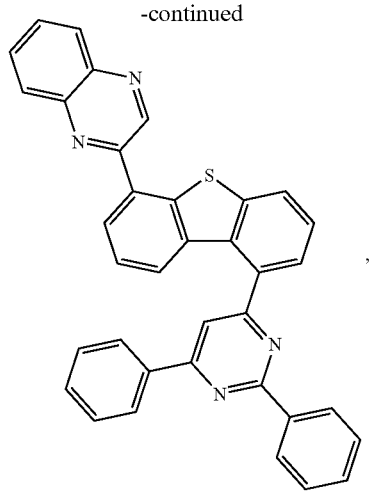
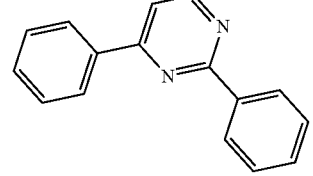
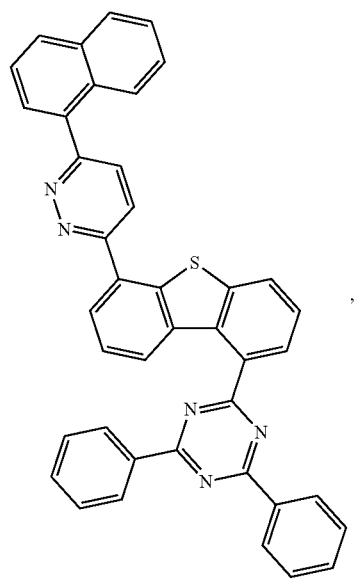
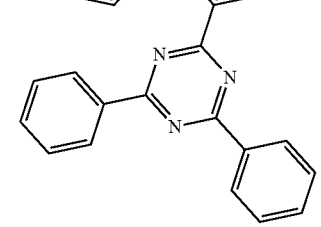
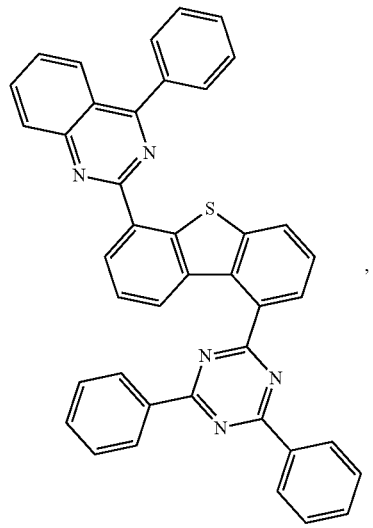
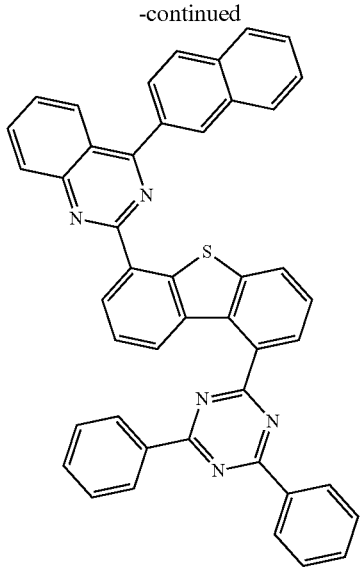
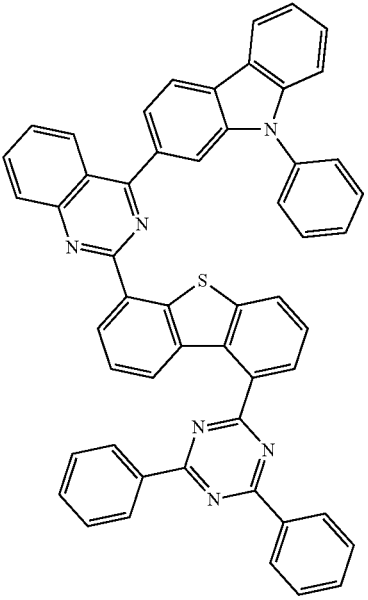
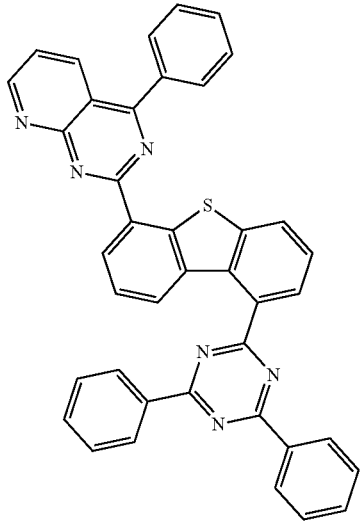

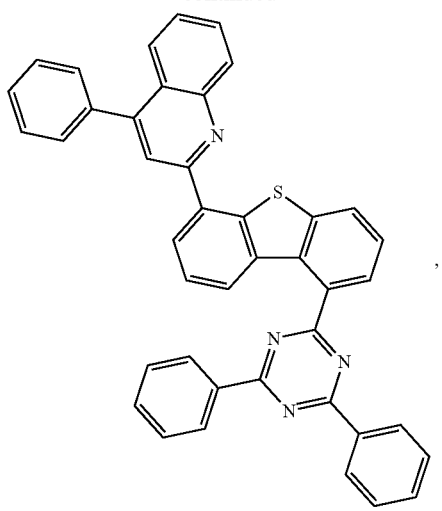
,
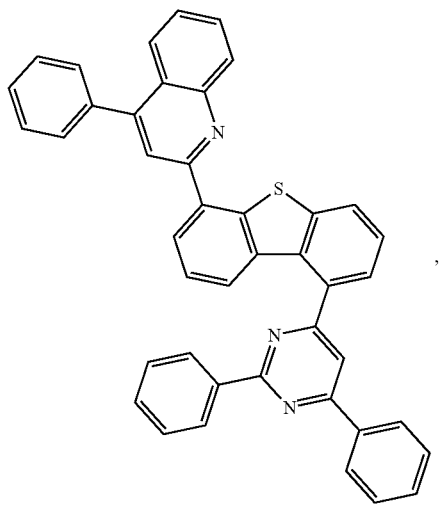
,
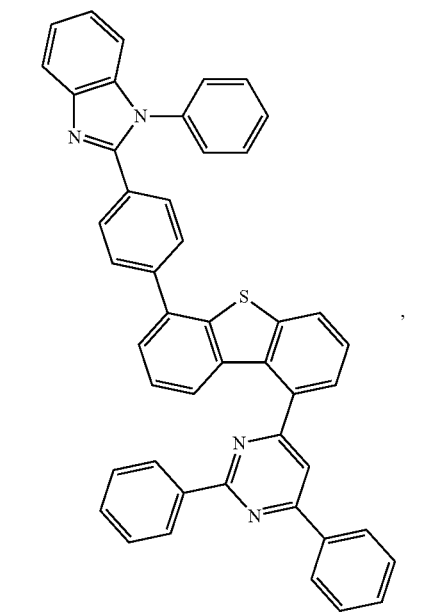
,
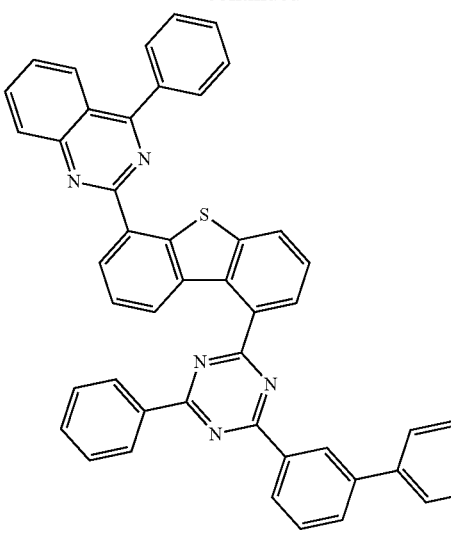
,
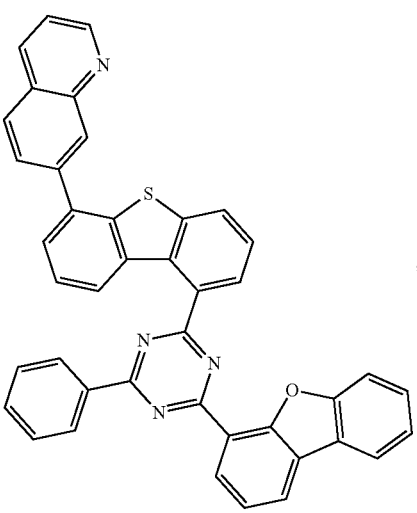
,
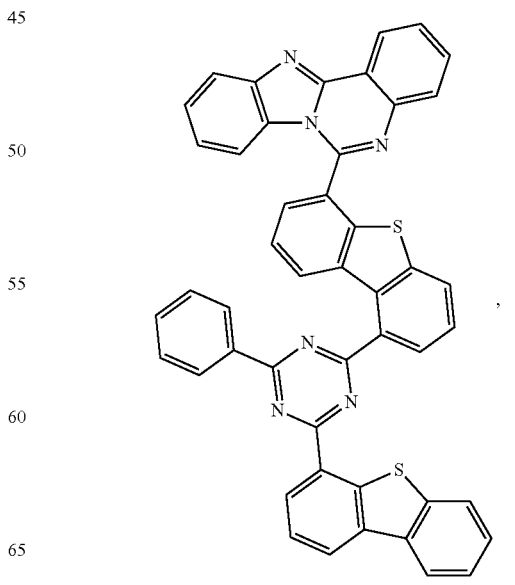
,

-continued
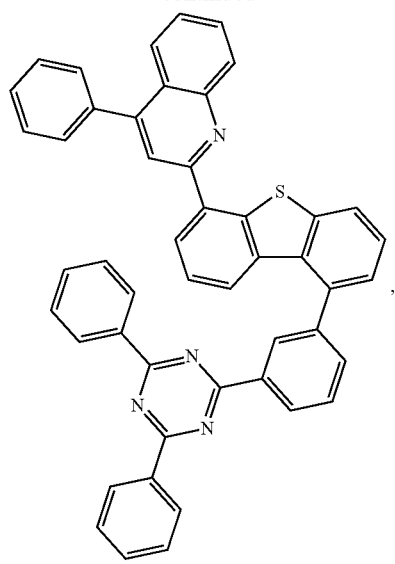
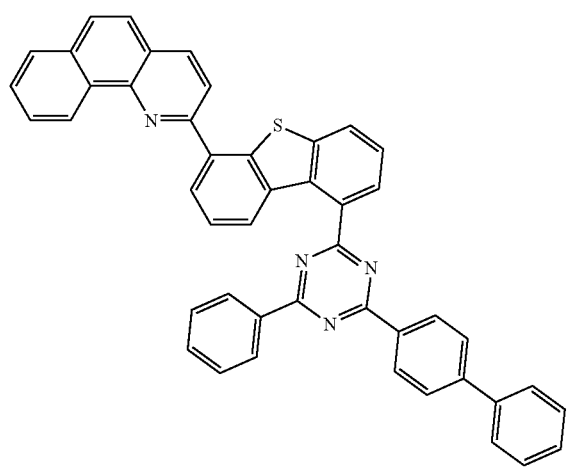
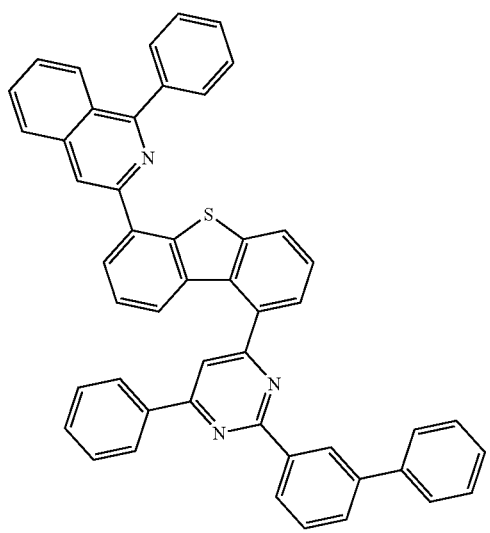
-continued
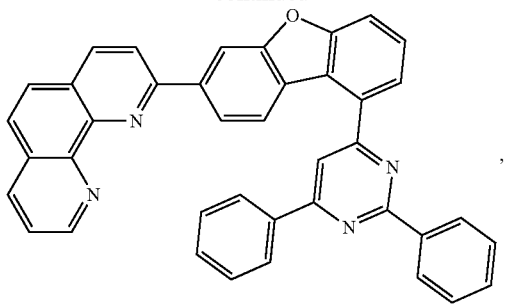
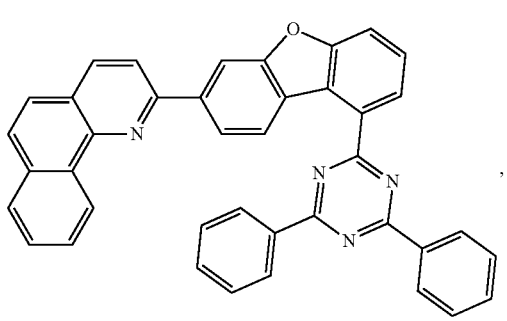
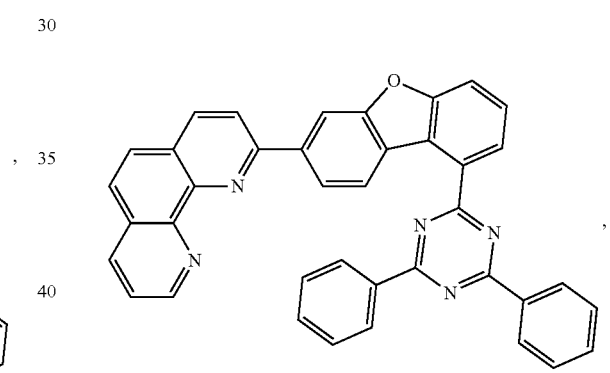
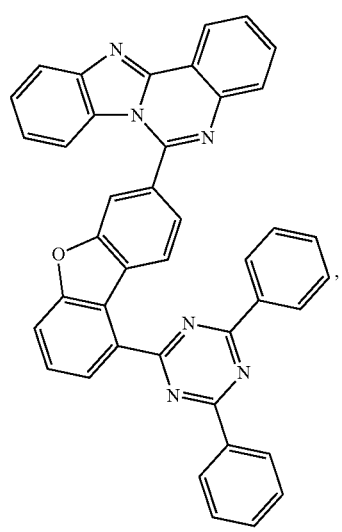

33
-continued
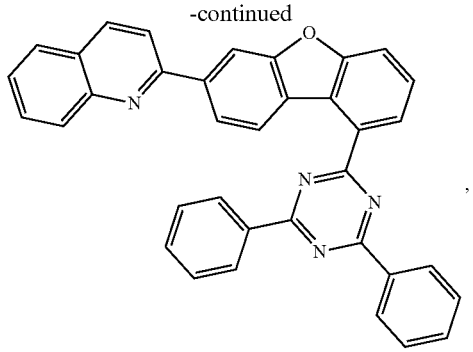
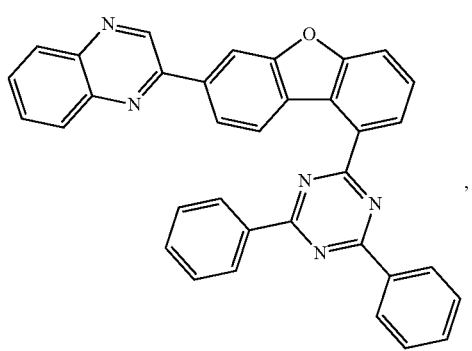
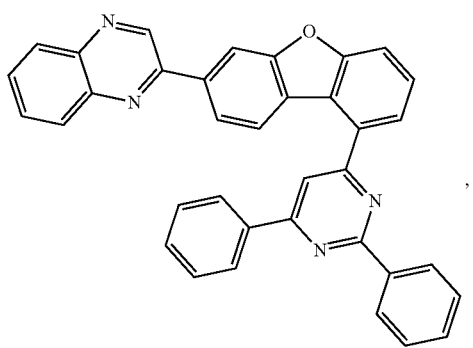
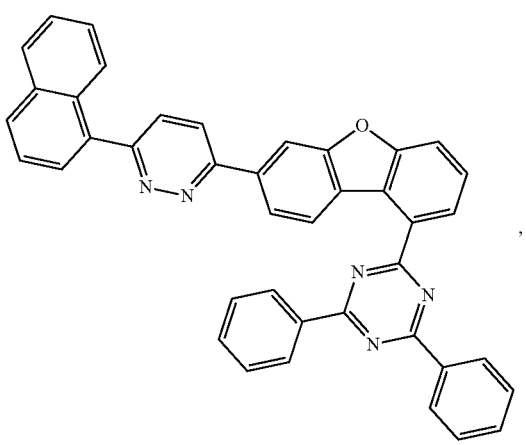
34
-continued
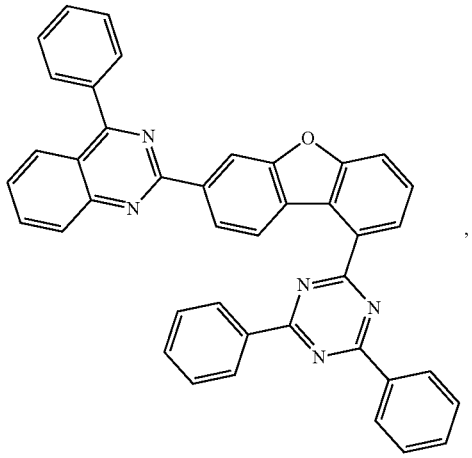
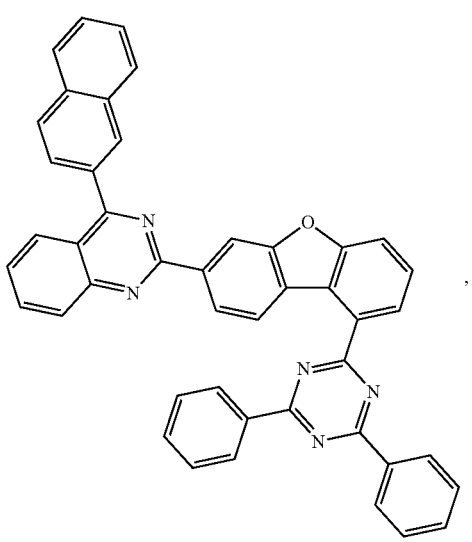
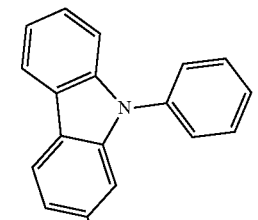
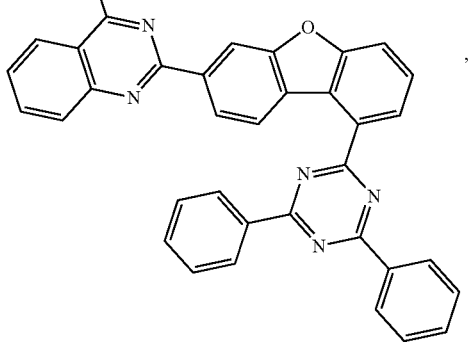

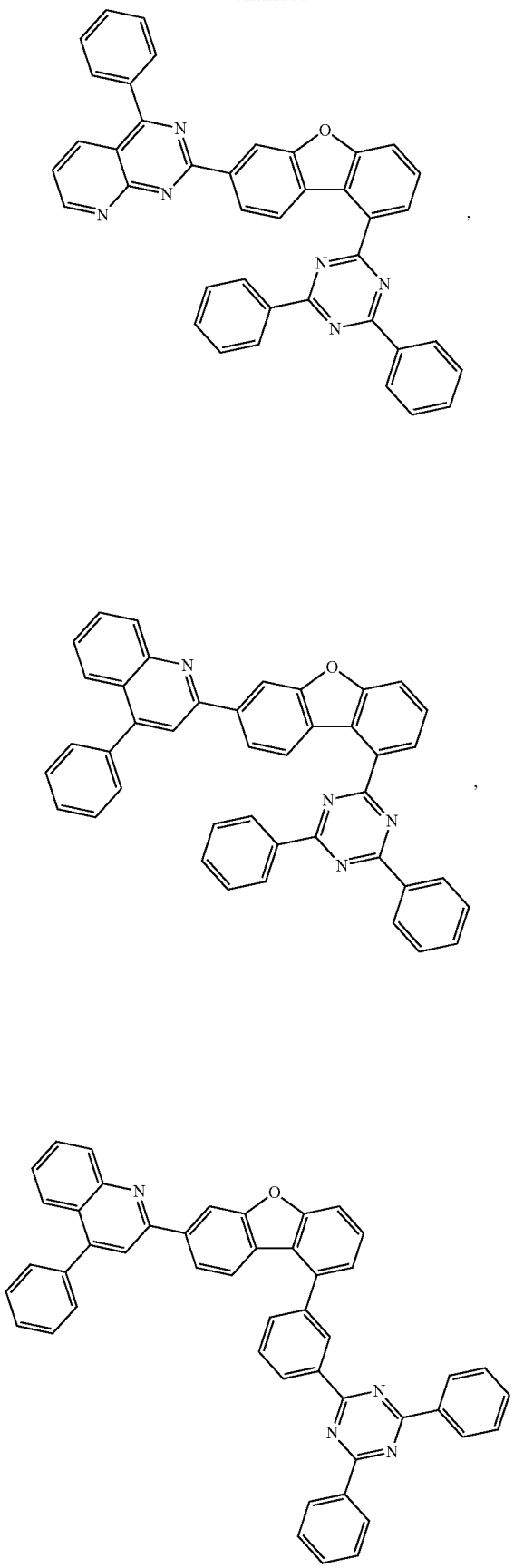
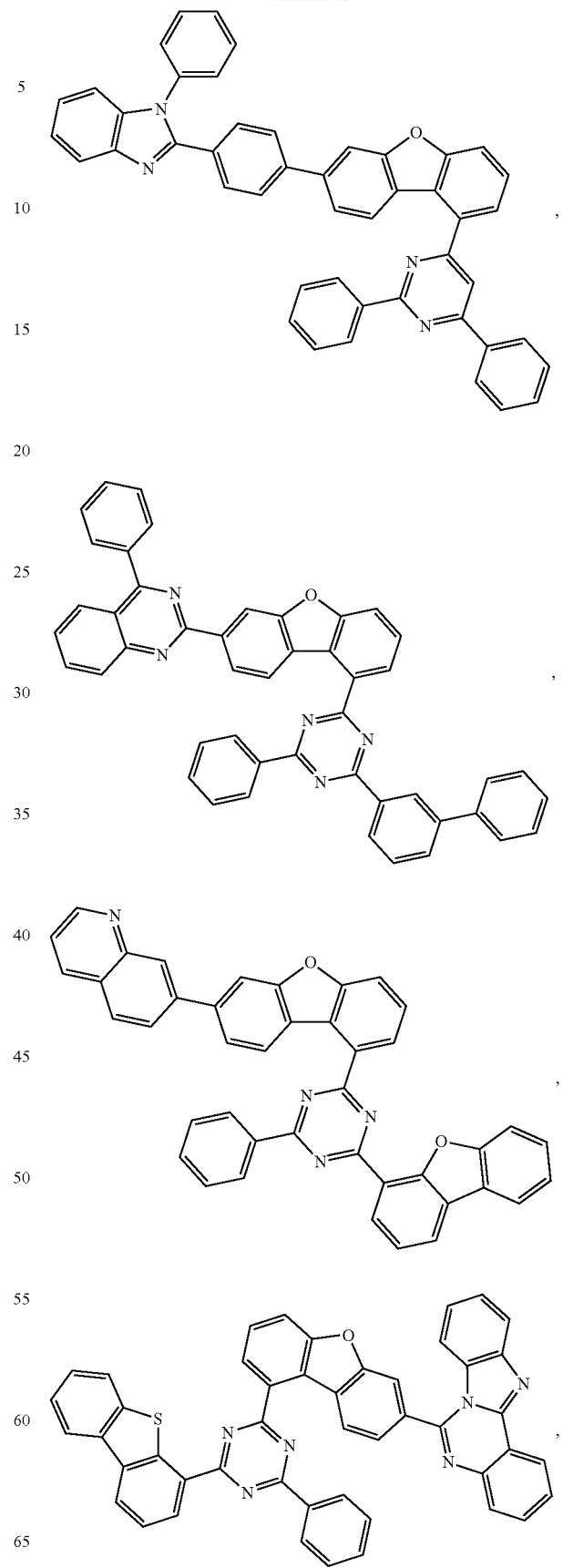

-continued
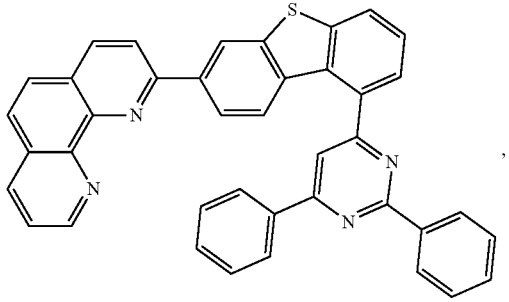
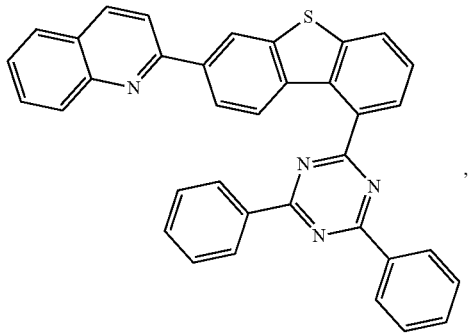
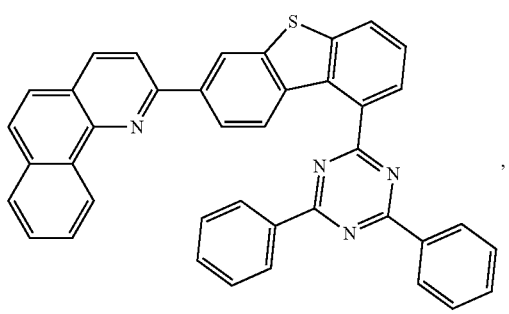
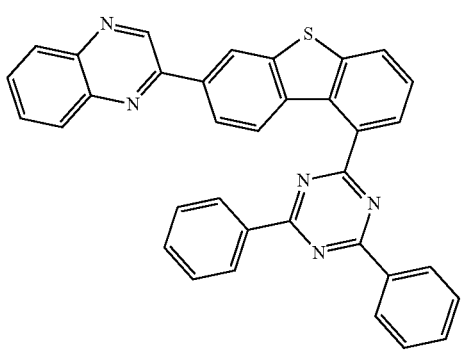
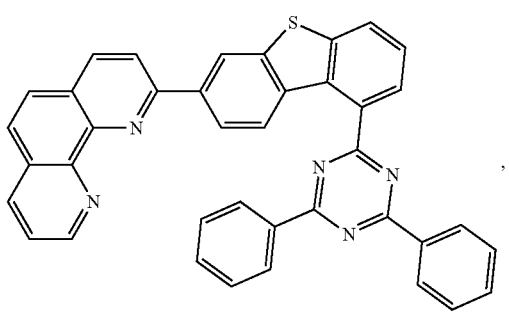
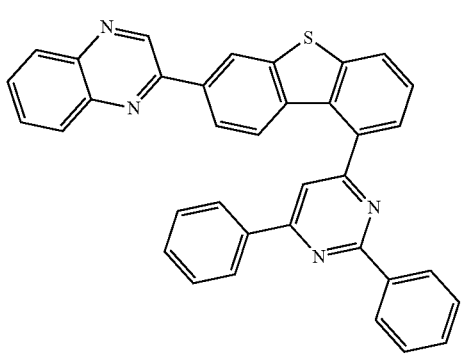
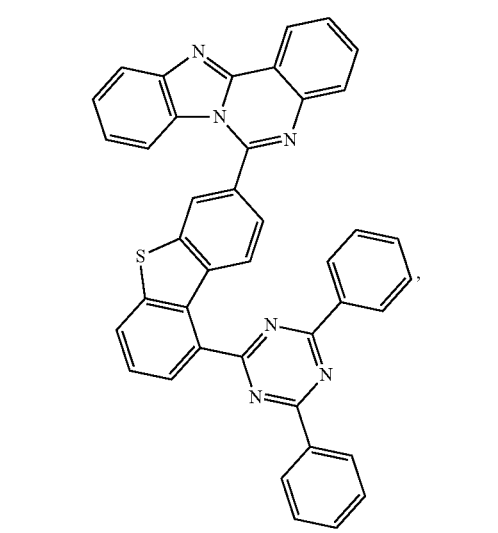
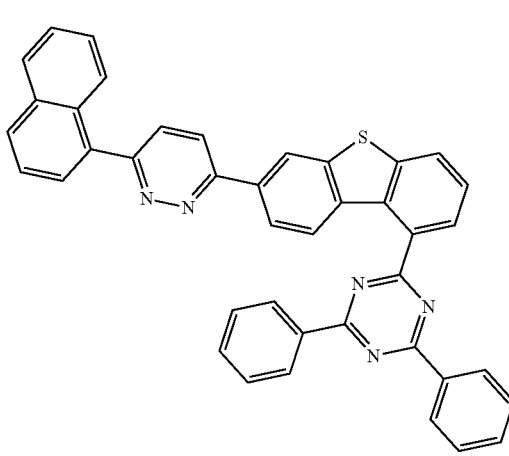

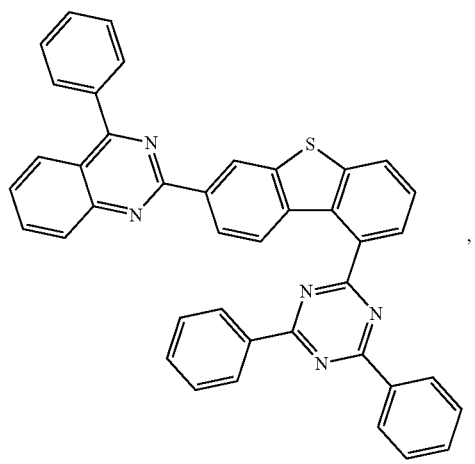
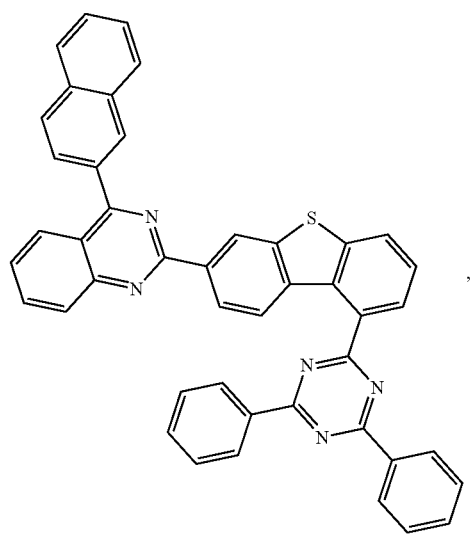
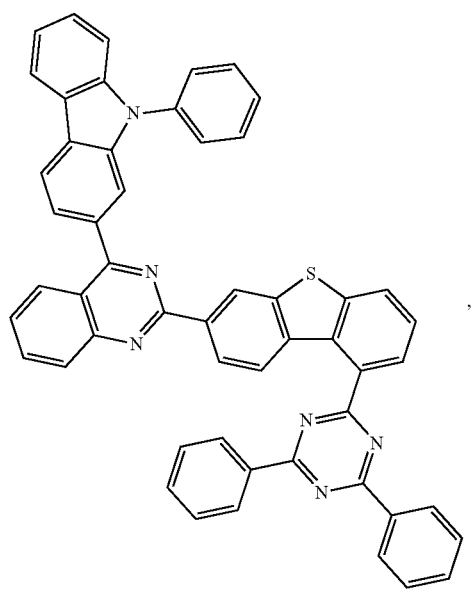
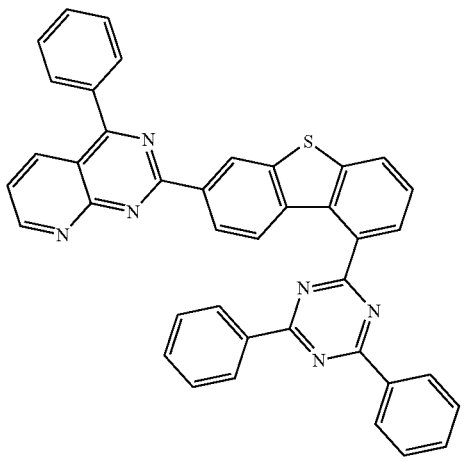
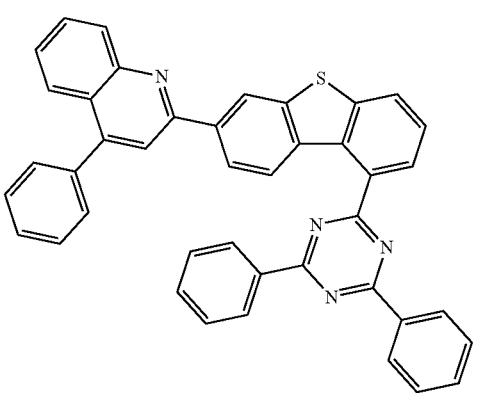
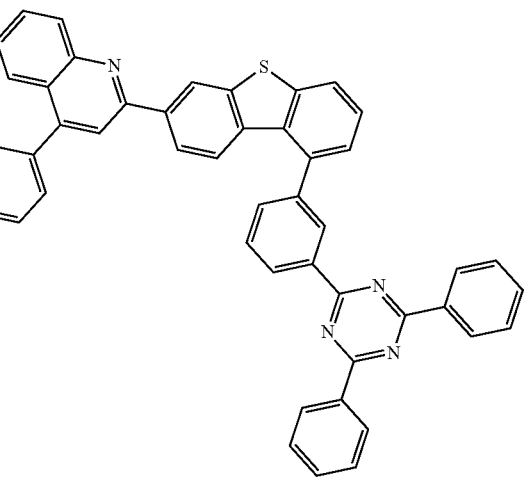

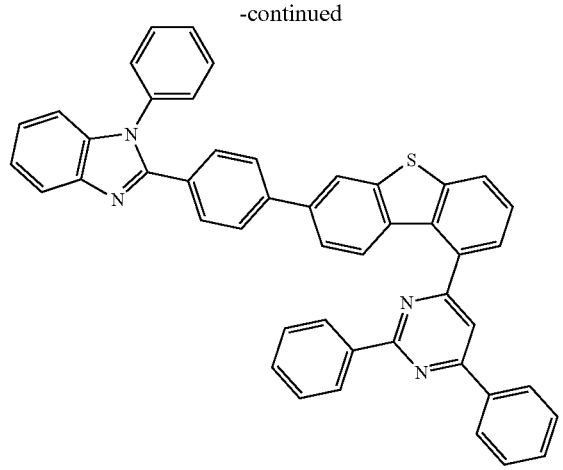
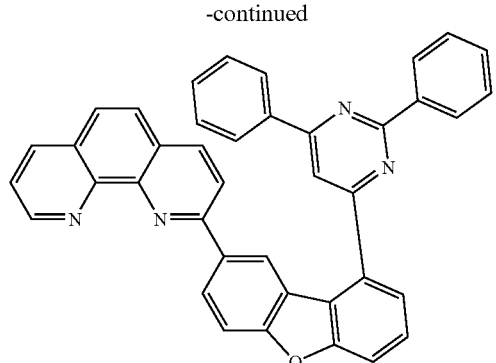
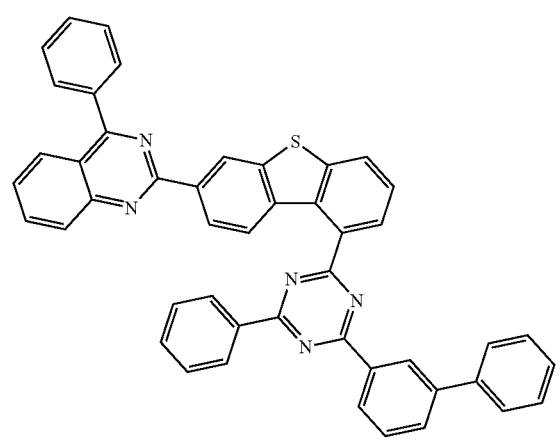
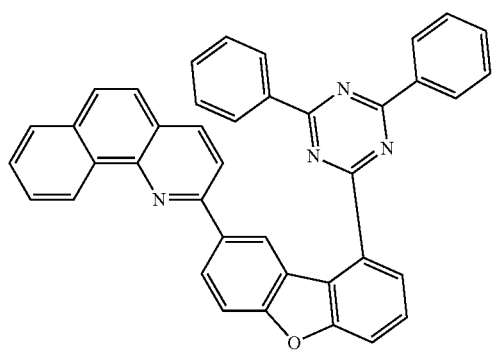
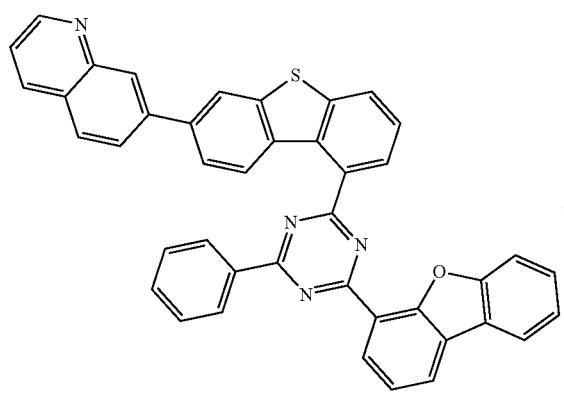
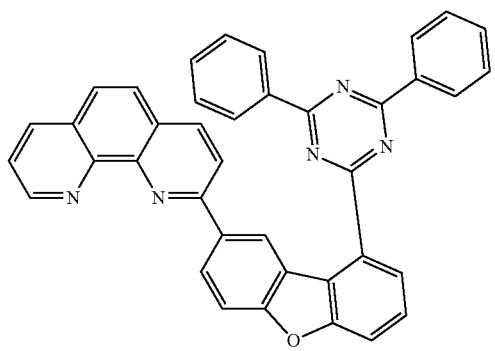
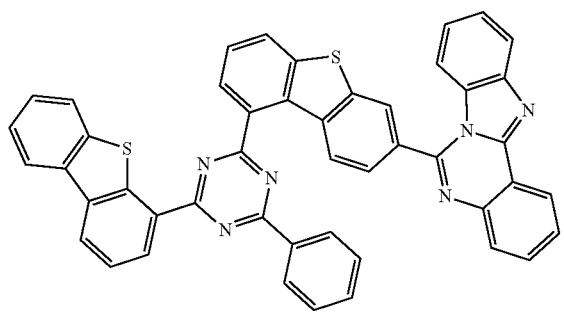
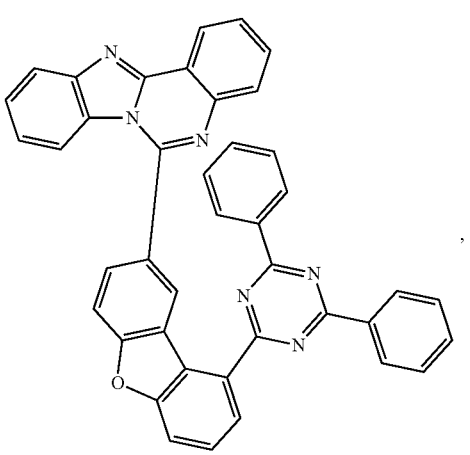

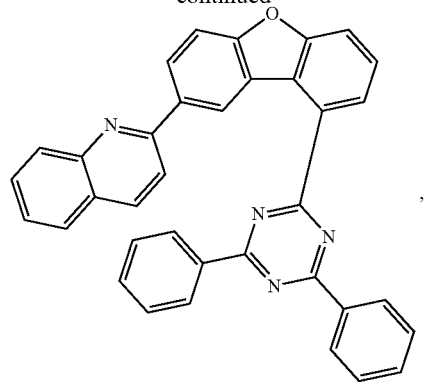
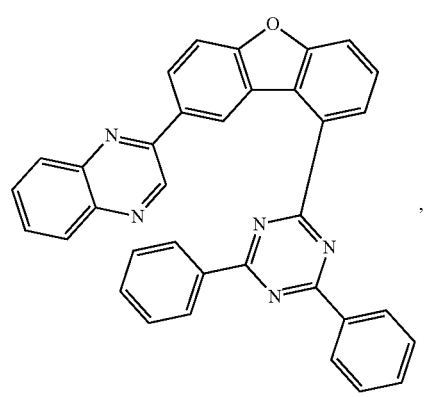
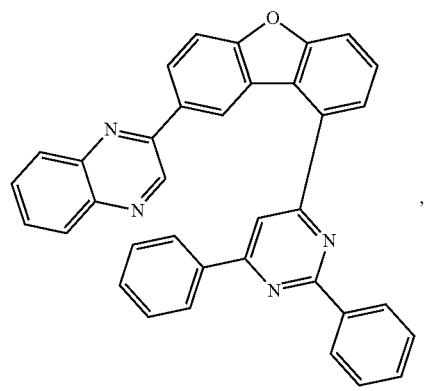
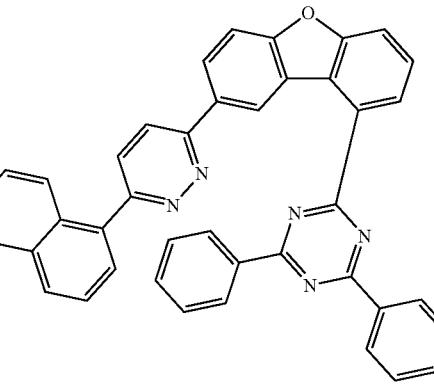
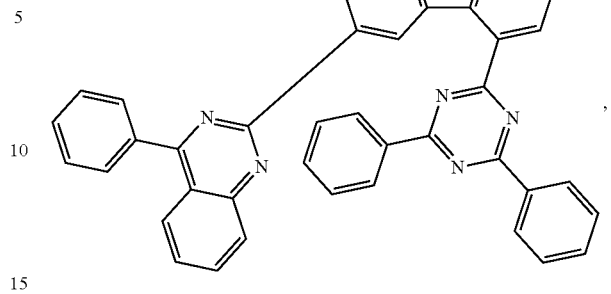
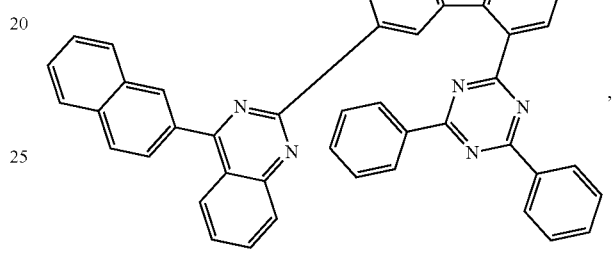
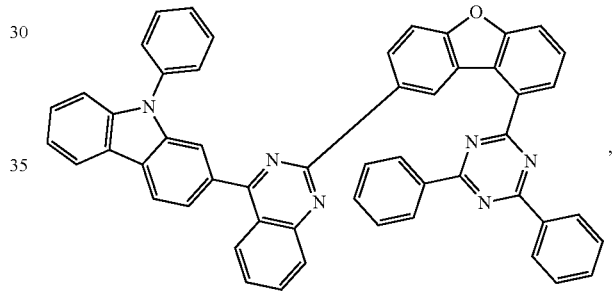
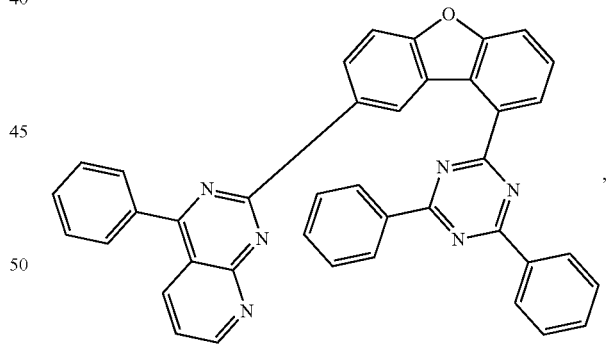
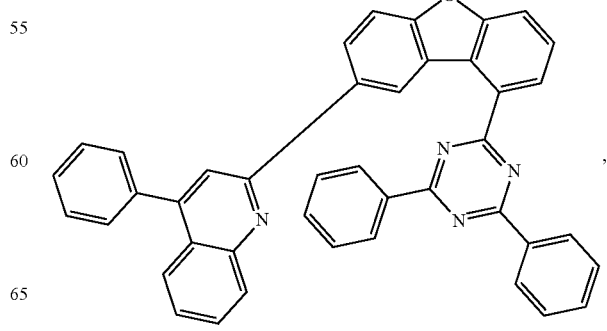

-continued
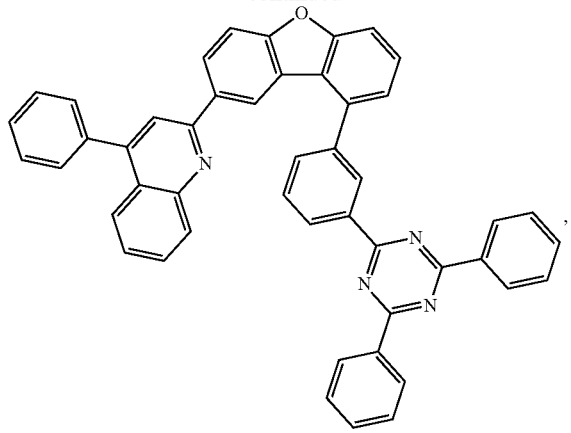
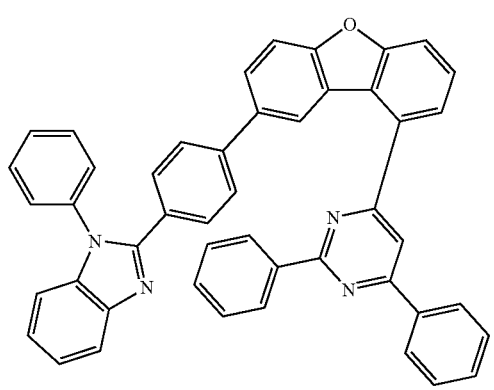
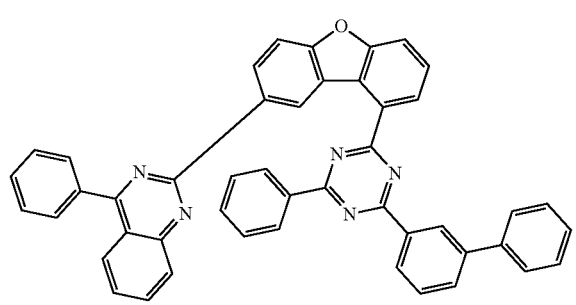
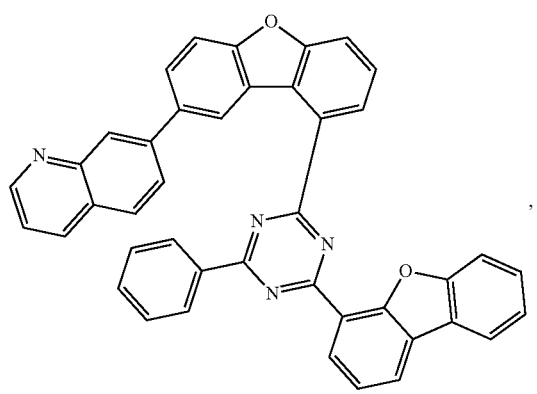
-continued
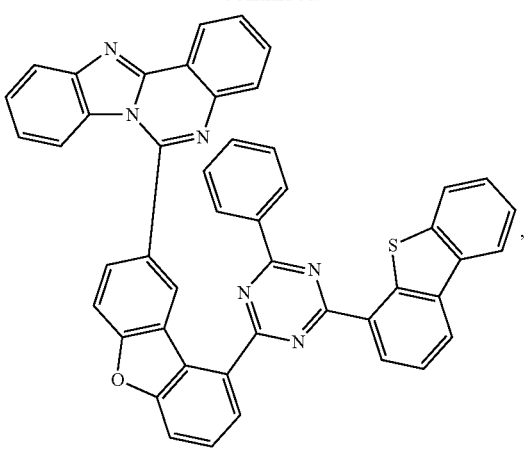
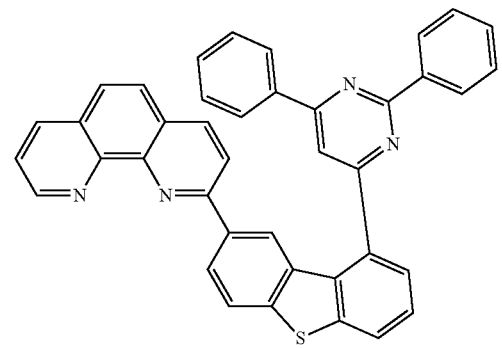

-continued
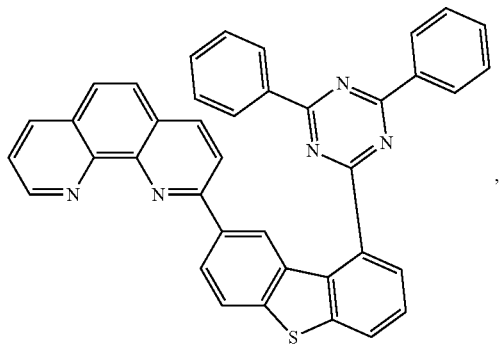
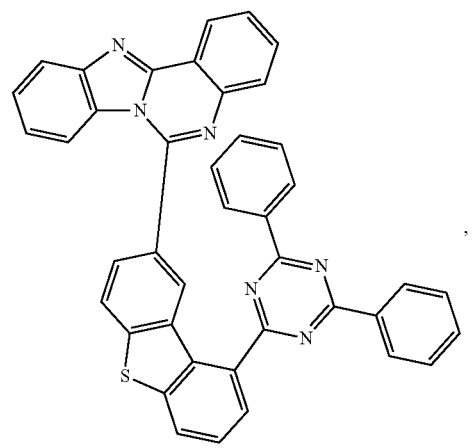
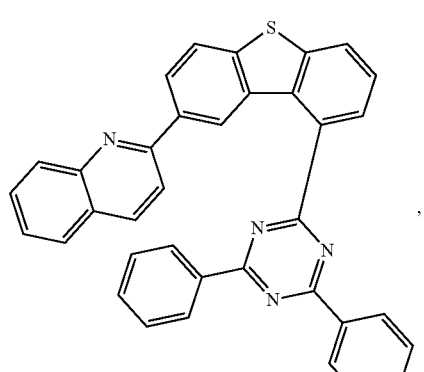
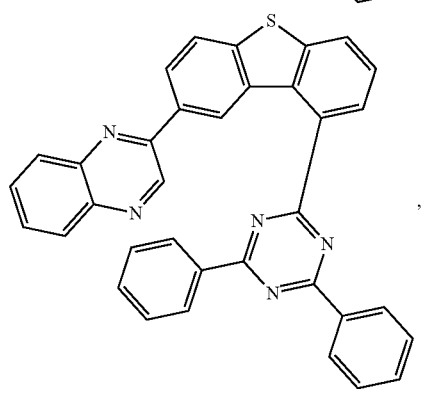
-continued
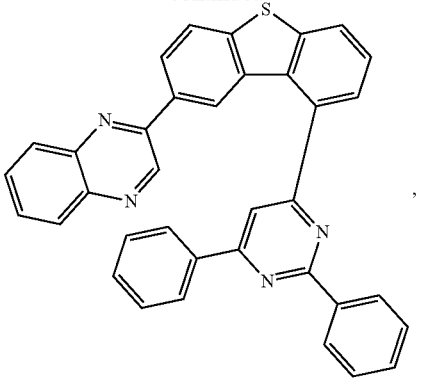
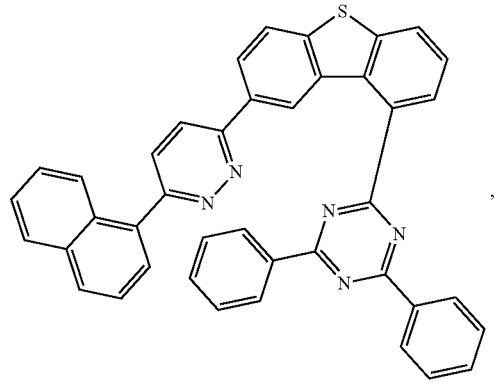
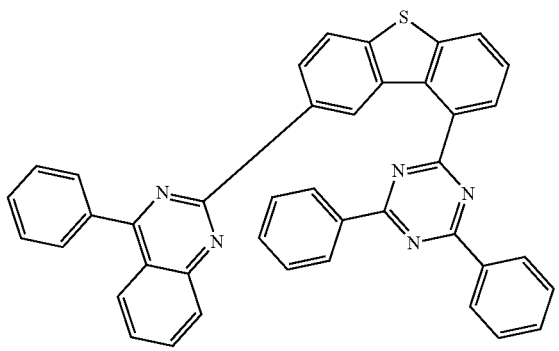
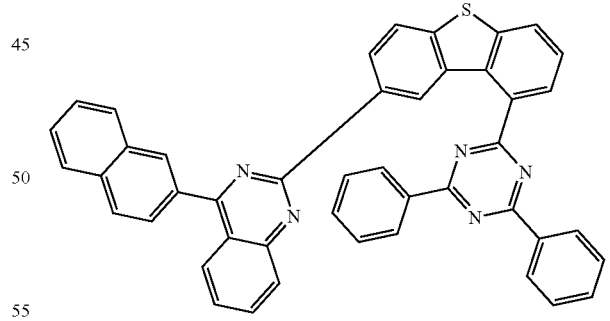
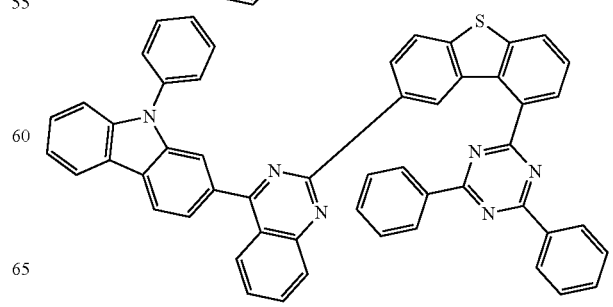

49
-continued
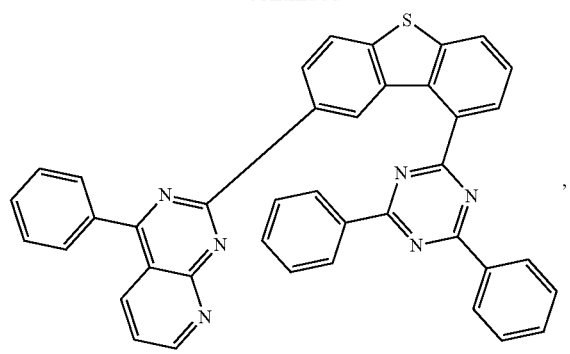
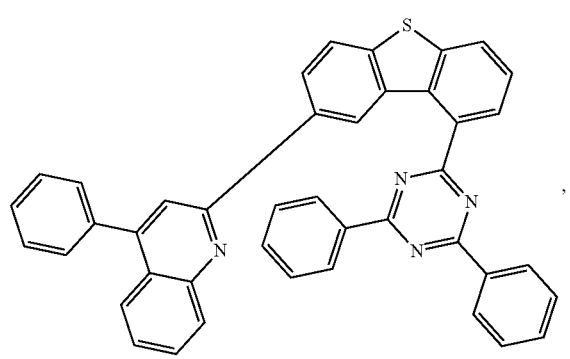
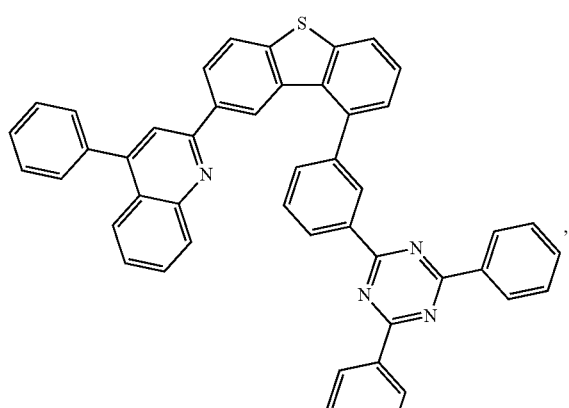
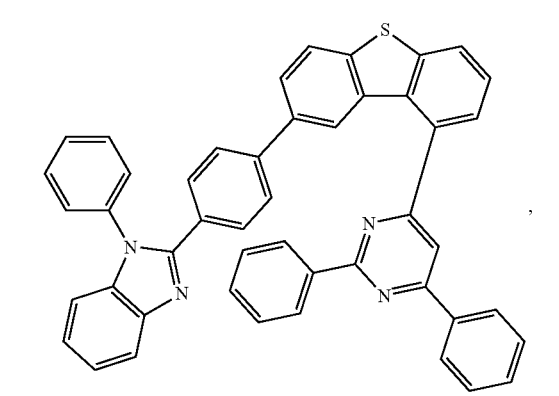
50
-continued
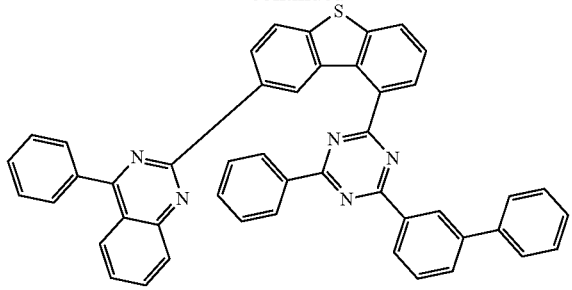
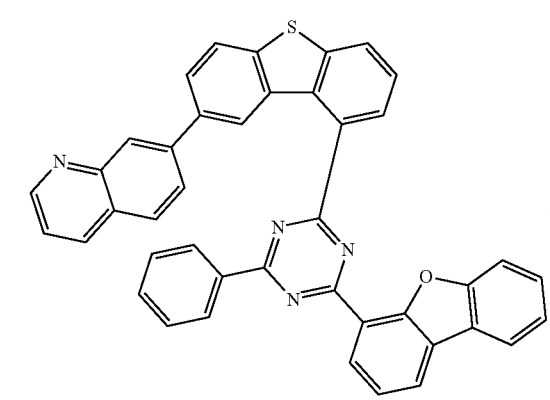
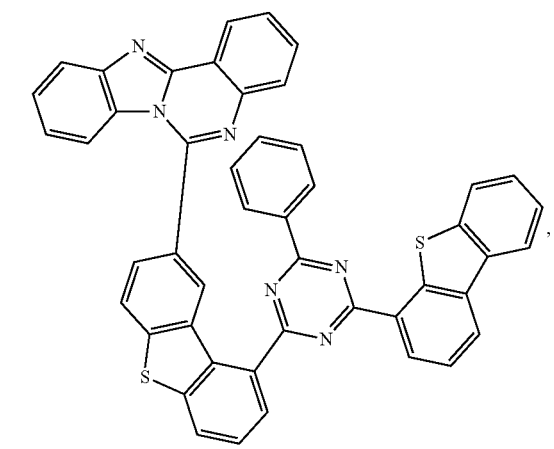
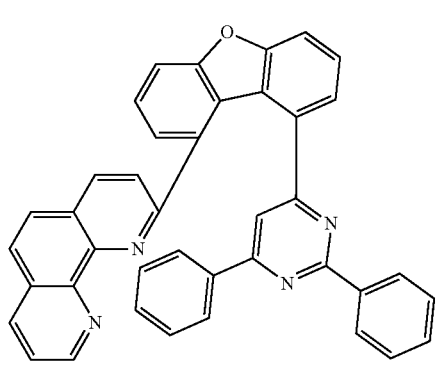

51
-continued
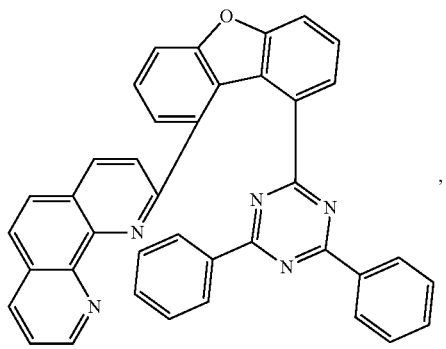
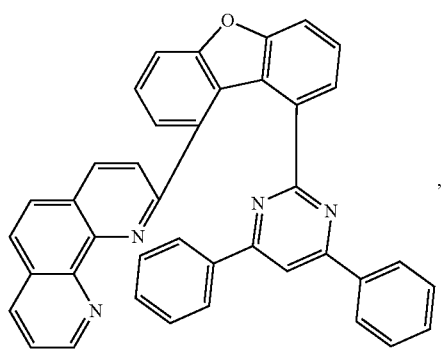
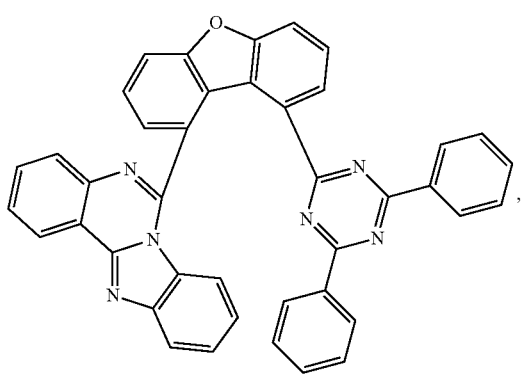
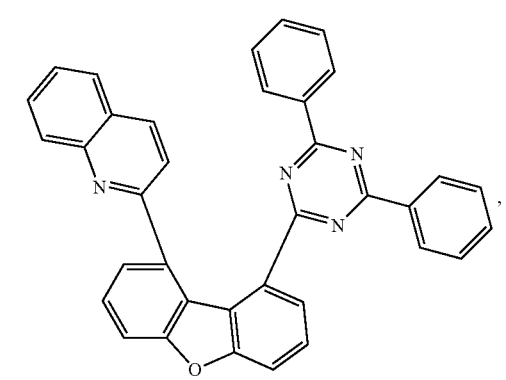
52
-continued
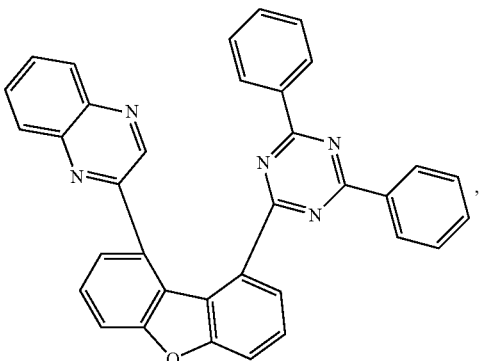
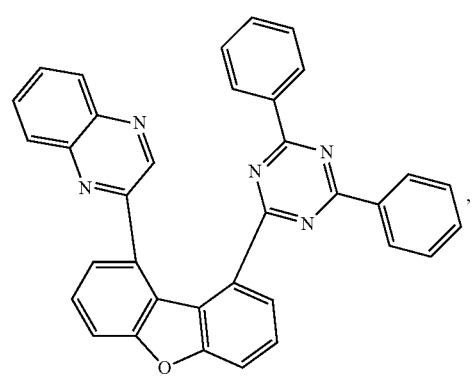
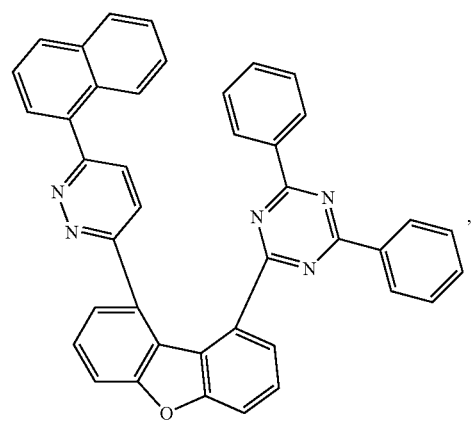
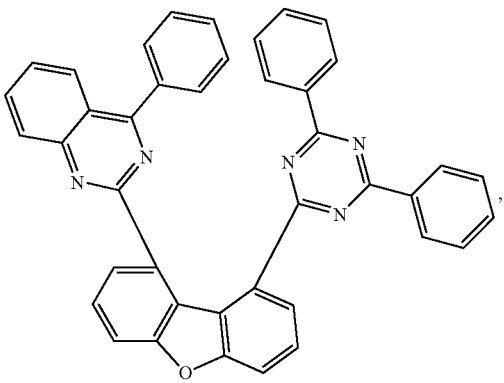

53
-continued
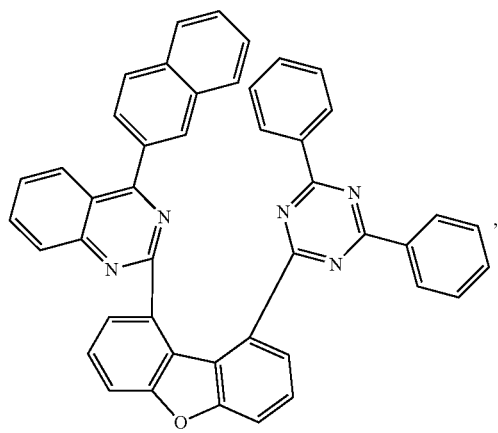
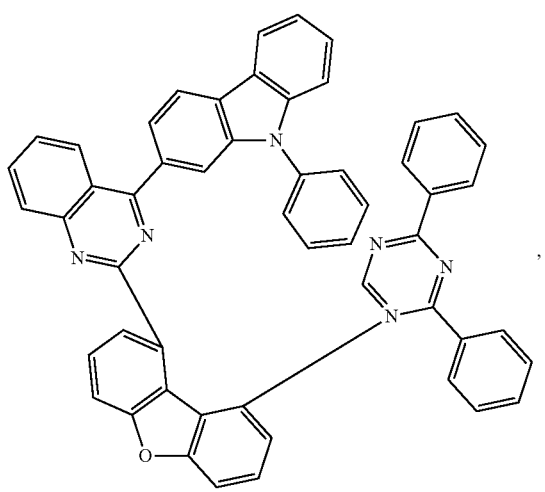
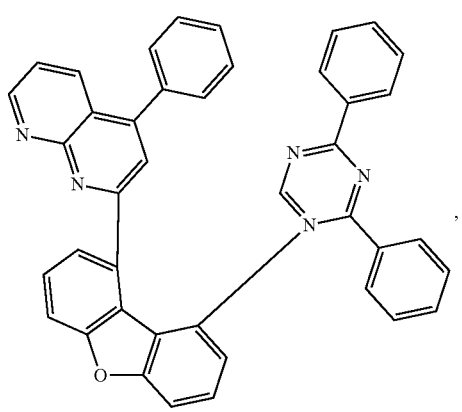
54
-continued
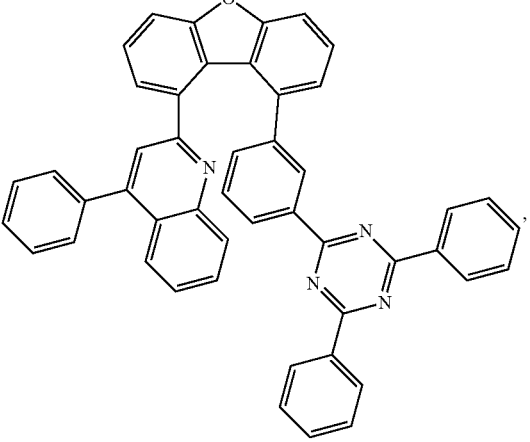
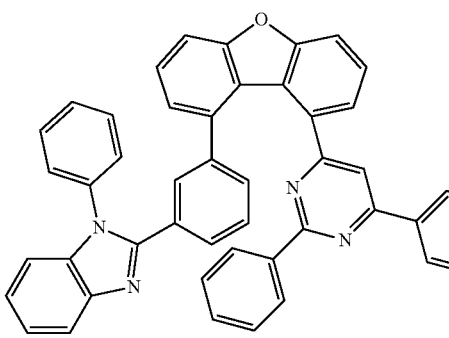
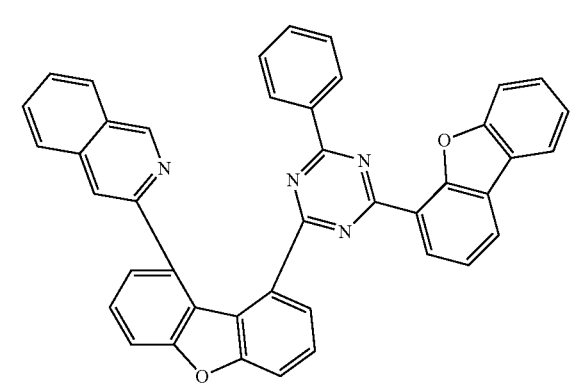

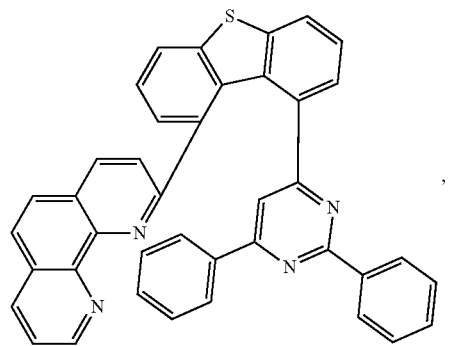
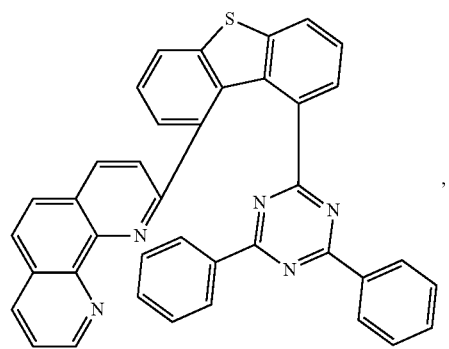
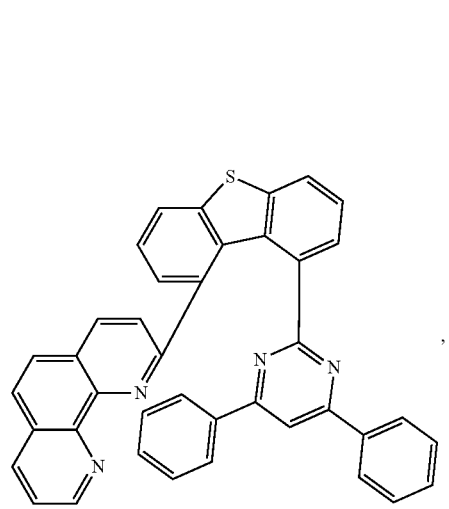
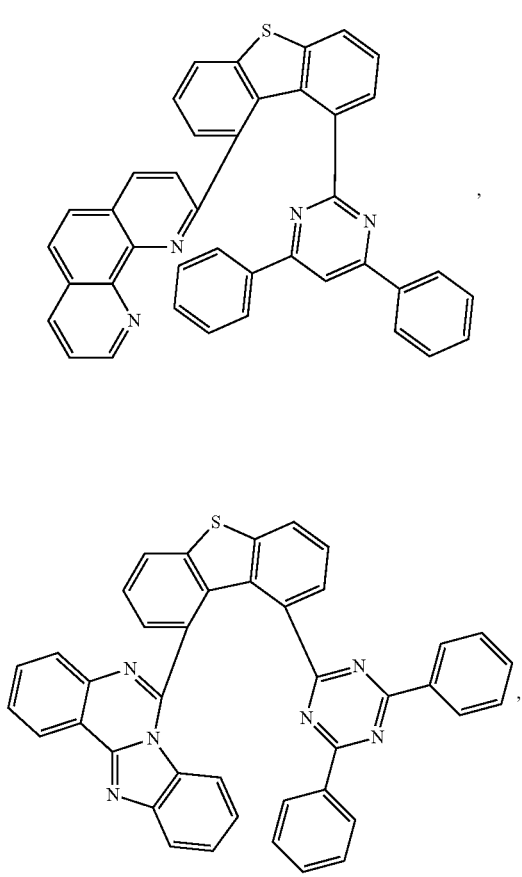
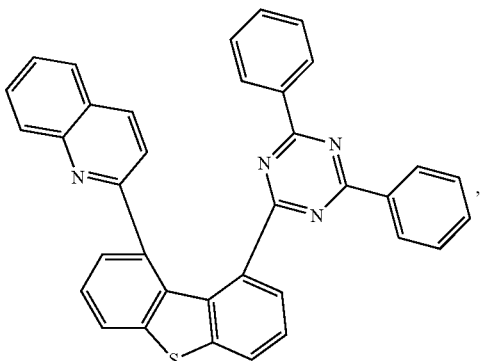
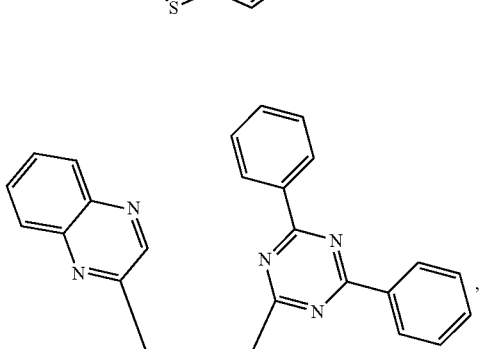
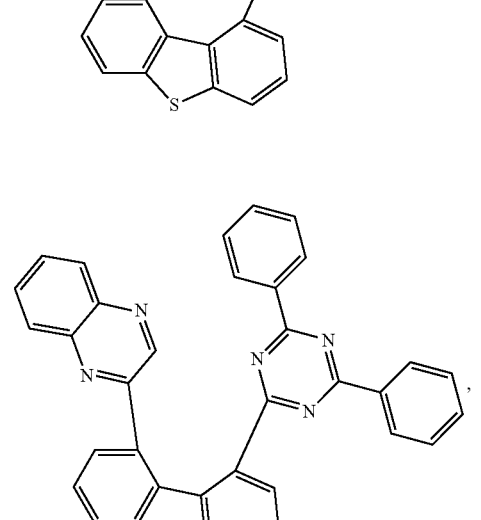
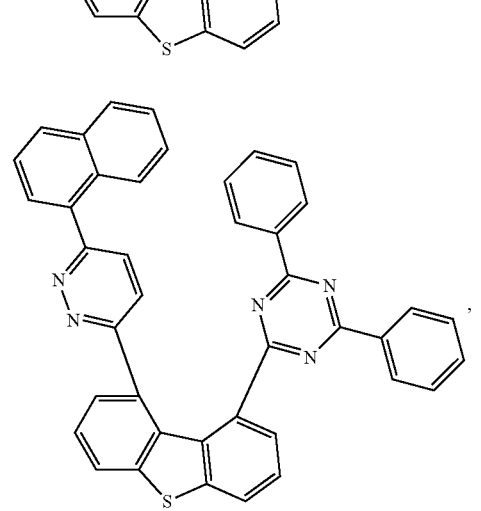

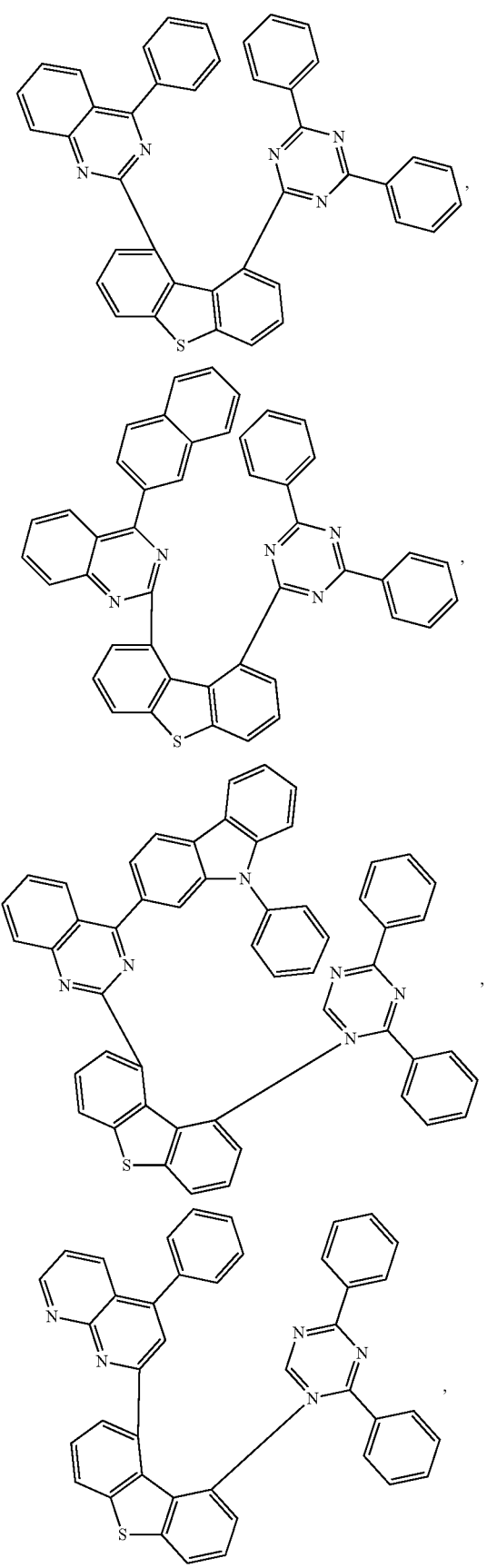
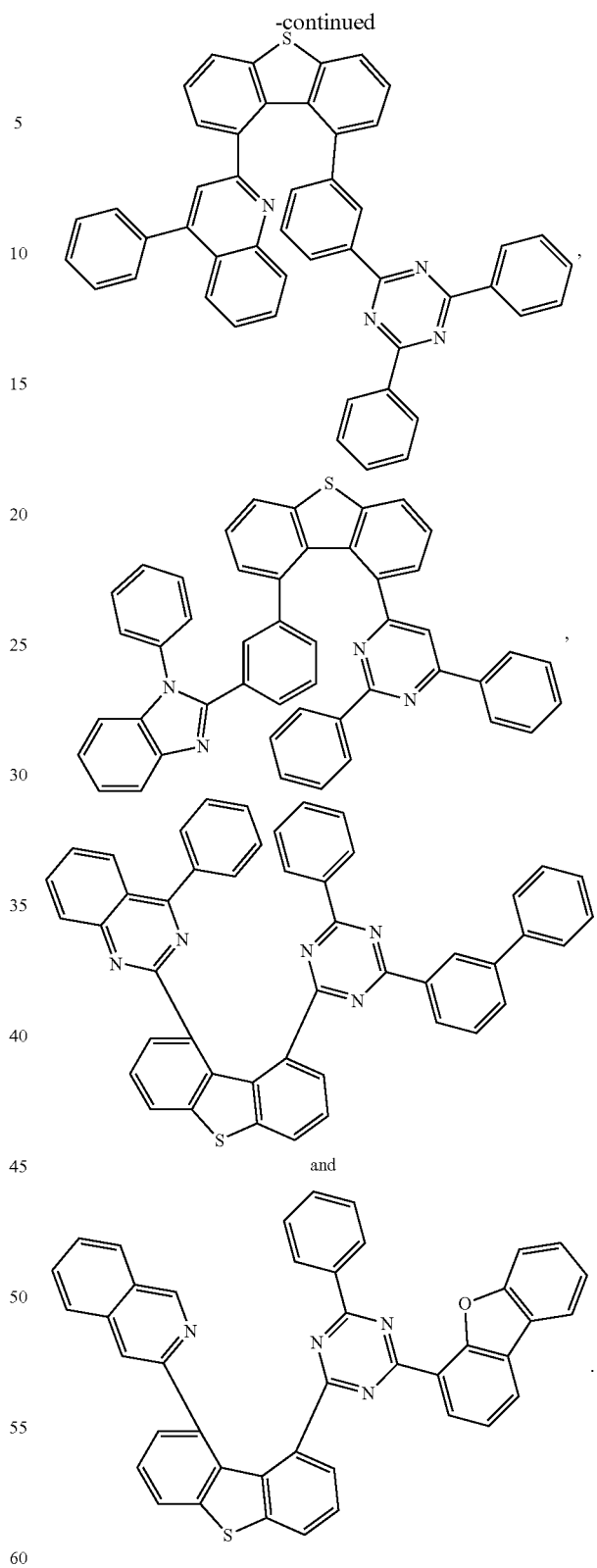
Since the compound of Formula 1 has a structure that simultaneously has a substituent such as triazine (pyridine, pyrimidine) substituted at the 1-position of the dibenzofuran (dibenzothiophene) core and the above-described substituent Het, it is possible to exhibit excellent heat resistance and simultaneously suppress the crystallization during the operation of the device. Therefore, an organic light emitting device using the same can have high efficiency, a low driving voltage, high luminance, a long lifetime, and the like.

The compound of Formula 1 can be prepared according to the preparation method as shown in Reaction Scheme 1 below.

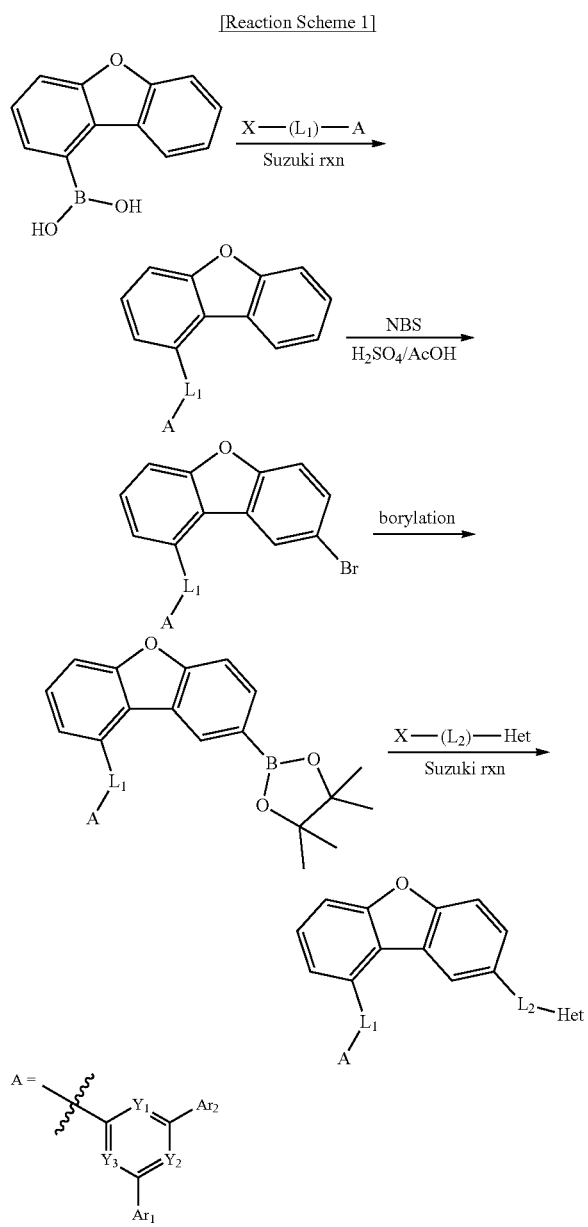

[Reaction Scheme 1]

In Reaction Scheme 1, $L_1$, $L_2$, $Y_1$, $Y_2$, $Y_3$, $Ar_1$, $Ar_2$, and Het are as defined above. The type of the reactive group and the catalyst used in Reaction Scheme 1 can be appropriately changed.

In addition, the present invention provides an organic light emitting device including the compound of Formula 1. In one example, the present invention provides an organic light emitting device including: a first electrode; a second electrode provided at a side opposite to the first electrode; and at least one organic material layer provided between the first electrode and the second electrode, wherein the at least one organic material layer includes a compound of Formula 1.

The organic material layer of the organic light emitting device of the present invention can have a single layer structure, or it can have a multilayered structure in which two or more organic material layers are stacked. For example, the organic light emitting device of the present invention can have a structure including a hole injection layer, a hole transport layer, a light emitting layer, an electron transport layer, an electron injection layer, and the like as the organic material layer. However, the structure of the organic light emitting device is not limited thereto, and it can include a smaller number of organic layers.

Further, the organic material layer can include a hole injection layer, a hole transport layer, or a layer simultaneously performing hole injection and transport, wherein the hole injection layer, the hole transport layer, and the layer simultaneously performing hole injection and transport include a compound of Formula 1.

Further, the organic material layer can include a light emitting layer, wherein the light emitting layer includes a compound of Formula 1.

Further, the organic material layer can include an electron transport layer or an electron injection layer, wherein the electron transport layer or the electron injection layer includes a compound of Formula 1.

Further, the electron transport layer, the electron injection layer, and the layer simultaneously performing electron injection and electron transport include a compound of Formula 1. In particular, the compound of Formula 1 according to one embodiment of the present invention has excellent thermal stability, a deep HOMO level of 6.0 eV or more, and high triplet energy (ET) and hole stability. Further, when the compound of Formula 1 is used for an organic material layer capable of simultaneously performing electron injection and electron transport, the n-type dopant used in the art can be mixed and used.

Further, the organic material layer can include a light emitting layer and an electron transport layer, wherein the electron transport layer can include a compound of Formula 1.

Further, the organic light emitting device according to the present invention can be a normal type of organic light emitting device in which an anode, at least one organic material layer, and a cathode are sequentially stacked on a substrate. Alternatively, the organic light emitting device according to the present invention can be an inverted type of organic light emitting device in which a cathode, at least one organic material layer, and an anode are sequentially stacked on a substrate. For example, the structure of an organic light emitting device according to an embodiment of the present invention is illustrated in FIGS. 1 and 2.

FIG. 1 shows an example of an organic light emitting device including a substrate 1, an anode 2, a light emitting layer 3, and a cathode 4. In such a structure, the compound of Formula 1 can be included in the light emitting layer.

FIG. 2 shows an example of an organic light emitting device including a substrate 1, an anode 2, a hole injection layer 5, a hole transport layer 6, a light emitting layer 7, an electron transport layer 8, and a cathode 4. In such a structure, the compound of Formula 1 can be included in at least one layer of the hole injection layer, the hole transport layer, the light emitting layer, and the electron transport layer.

The organic light emitting device according to the present invention can be manufactured by materials and methods known in the art, except that at least one organic material layer includes the compound of Formula 1. In addition, when the organic Tight emitting device includes a plurality of organic material layers, the organic material layers can be formed of the same material or different materials.

For example, the organic light emitting device according to the present invention can be manufactured by sequentially stacking a first electrode, an organic material layer, and a second electrode on a substrate. In this case, the organic light emitting device can be manufactured by depositing a metal, metal oxides having conductivity, or an alloy thereof on the substrate by using a PVD (physical vapor deposition) method such as a sputtering method or an e-beam evaporation method to form the anode, forming an organic material layer including the hole injection layer, the hole transport layer, the light emitting layer, and the electron transport layer thereon, and then depositing a material that can be used as the cathode thereon. In addition to such a method, the organic light emitting device can be manufactured by sequentially depositing a cathode material, an organic material layer, and an anode material on a substrate.

In addition, the compound of Formula 1 can be formed into an organic layer by a solution coating method as well as a vacuum deposition method at the time of manufacturing an organic light emitting element. Herein, the solution coating method means spin coating, dip coating, doctor blading, inkjet printing, screen printing, a spray method, roll coating, or the like, but is not limited thereto.

In addition to such a method, the organic light emitting device can be manufactured by sequentially depositing a cathode material, an organic material layer, and an anode material on a substrate (International Publication WO 2003/012890). However, the manufacturing method is not limited thereto.

For example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include: metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or SnO$_2$:Sb; conductive polymers such as poly(3-methylthiophene), poly[3,4-(ethylene-1,2-dioxy)thiophene](PEDOT), polypyrrole, and polyaniline; and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or alloys thereof; a multilayered structure material such as LiF/Al or LiO$_2$/Al, and the like, but are not limited thereto.

The hole injection layer is a layer for injecting holes from the electrode, and the hole injection material is preferably a compound which has an ability of transporting the holes, a hole injecting effect in the anode, and an excellent hole injecting effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline, and a polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which can receive holes from the anode or the hole injection layer and transfer holes to the light emitting layer. Specific examples thereof include an arylamine-based organic material, a conductive polymer, a block copolymer in which a conjugate portion and a non-conjugate portion are present together, and the like, but are not limited thereto.

The light emitting material is a material capable of emitting light in the visible light region by combining holes and electrons respectively transported from the hole transport layer and the electron transport layer, and having good quantum efficiency for fluorescence or phosphorescence. Specific examples include an 8-hydroxy-quinoline aluminum (Alq$_3$) complex; carbazole-based compounds; dimerized styryl compounds; BAlq; 10-hydroxybenzoquinoline-metal compounds; benzoxazole, benzothiazole, and benzimidazole-based compounds; poly(p-phenylene vinylene) (PPV)-based polymers; spiro compounds; and polyfluorene, rubrene, and the like, but are not limited thereto.

The light emitting layer can include a host material and a dopant material. The host material can be a fused aromatic ring derivative, a heterocycle-containing compound, or the like. Specific examples of the fused aromatic ring derivatives include anthracene derivatives, pyrene derivatives, naphthalene derivatives, pentacene derivatives, phenanthrene compounds, and fluoranthene compounds. Examples of heterocyclic compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specific examples of the aromatic amine derivatives include substituted or unsubstituted fused aromatic ring derivatives having an arylamino group, and examples thereof include pyrene, anthracene, chrysene, and periflanthene having the arylamino group, and the like. The styrylamine compound is a compound where at least one arylvinyl group is substituted in a substituted or unsubstituted arylamine, in which one or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer receiving the electrons from the electron injection layer and transporting the electrons to the light emitting layer, and the electron transport material is a material that can receive the electrons well from the cathode and transport the electrons to the light emitting layer, wherein a material having large mobility to the electrons is suitable. Specific examples thereof include an 8-hydroxyquinoline Al complex, a complex including Alq$_3$, an organic radical compound, a hydroxyflavone-metal complex, and the like, but are not limited thereto. The electron transport layer can be used together with a predetermined desired cathode material as used according to the prior art. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer which injects the electrons from the electrode, and is preferably a compound which has an ability of transporting the electrons, an electron injecting effect from the cathode, and an excellent electron injecting effect to the light emitting layer or the light emitting material, prevents movement of an exciton generated in the light emitting layer to the hole injection layer, and has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato) beryllium, bis(10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium, and the like, but are not limited thereto.

The organic light emitting device according to the present invention can be a front side emission type, a back side emission type, or a double side emission type according to the material used.

In addition, the compound of Formula 1 can be included in an organic solar cell or an organic transistor in addition to an organic light emitting device.

The preparation of the compound of Formula 1 and the organic light emitting device including the same will be described in detail in the following examples. However, these examples are presented for illustrative purposes only, and the scope of the present invention is not limited thereto.

PREPARATION EXAMPLE 1

Preparation Example 1-1

Synthesis of Intermediate Compound A-4

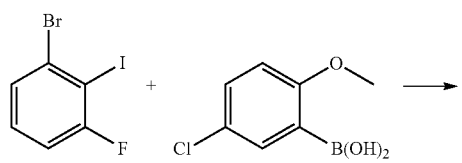

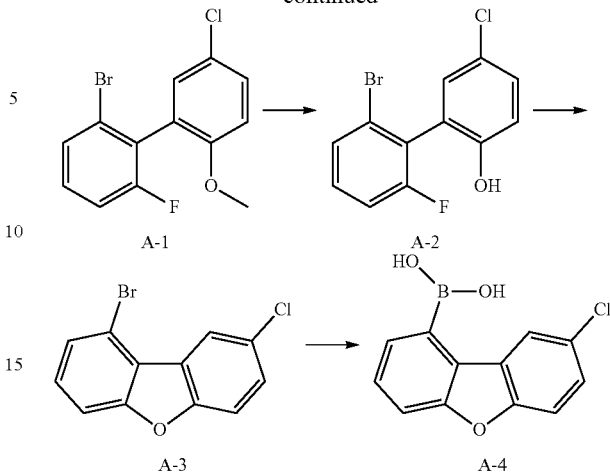

1) Preparation of Compound A-1

1-bromo-3-fluoro-2-iodobenzene (75 g, 249.3 mmol) and (5-chloro-2-methoxyphenyl)boronic acid (51.1 g, 249.3 mmol) were dissolved in 550 mL of tetrahydrofuran. A 2 M sodium carbonate (Na$_2$CO$_3$) solution (350 mL) and tetrakis (triphenylphosphine)palladium(0) (2.88 g, 2.49 mmol) were added thereto and refluxed for 11 hours. After the reaction was completed, the reaction mixture was cooled to room temperature. The aqueous layer was separated and removed, dried over anhydrous magnesium sulfate, and concentrated under reduced pressure. The resulting mixture was recrystallized using chloroform and ethanol to obtain Compound A-1 (63.2 g, yield 80%; MS: [M+H]$^+$=314).

2) Preparation of Compound A-2

Compound A-1 (63.2 g, 200.3 mmol) was dissolved in 750 mL of dichloromethane and then cooled to 0° C. Boron tribromide (20.0 mL, 210.3 mmol) was slowly added dropwise and then stirred for 12 hours. After the reaction was completed, the reaction mixture was washed three times with water, dried over magnesium sulfate, and filtered. The filtrate was distilled under reduced pressure and purified by column chromatography to obtain Compound A-2 (57.9 g, yield 96%; MS: [M+H]$^+$=300).

3) Preparation of Compound A-3

Compound A-2 (57.9 g, 192.0 mmol) and calcium carbonate (79.6 g, 576.0 mol) were dissolved in 350 mL of N-methyl-2-pyrrolidone, and then heated and stirred for 2 hours. After lowering the temperature to room temperature, the reaction mixture was subjected to reverse precipitation in water and filtered. The mixture was completely dissolved in dichloromethane, washed with water, dried over anhydrous magnesium sulfate, concentrated under reduced pressure, recrystallized using ethanol, and dried to obtain Compound A-3 (42.1 g, yield 78%; MS:[M+H]$^+$=280).

4) Preparation of Compound A-4

After Compound A-3 (42.1 q, 149.5 mmol) was dissolved in tetrahydrofuran (330 mi), the temperature was lowered to −78° C. and 2.5 M tert-butyllithium (t-BuLi) (60.4 mL, 151.0 mmol) was added slowly. The mixture was stirred at the same temperature for 1 hour, and then triisopropylborate (51.8 mL, 224.3 mmol) was added thereto, and stirred for 3 hours while gradually raising the temperature to room temperature. To the reaction mixture was added a 2N aqueous hydrochloric acid solution (300 mL), and the mixture was stirred at room temperature for 1.5 hours. The resulting precipitate was filtered, washed with water and ethyl ether, and then vacuum dried to obtain Intermediate A-4 (34.3 g, yield 93%; MS: [M+H]$^+$=247).

PREPARATION EXAMPLE 1-2

Synthesis of Intermediate Compound B-5

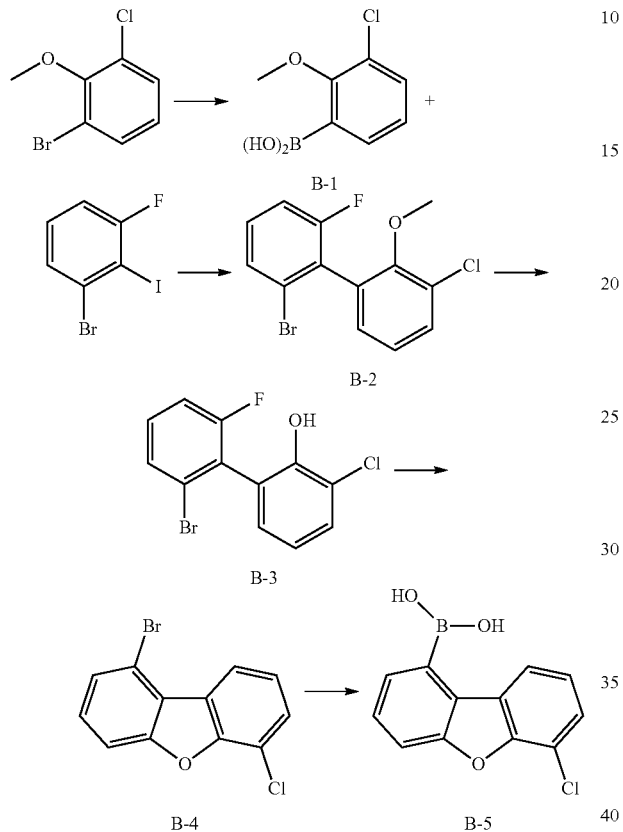

1) Preparation of Compound B-1

After 1-bromo-3-fluoro-2-methoxybenzene (100.0 g, 451.5 mmol) was dissolved in tetrahydrofuran (1000 mL), the temperature was lowered to −78° C. and 2.5 M tert-butyl lithium (t-BuLi) (182.4 mL, 456.0 mmol) was slowly added dropwise. The mixture was stirred at the same temperature for 1 hour, and triisopropylborate (B(OiPr)$_3$) (156.3 mL, 677.3 mmol) was added thereto and stirred for 3 hours while gradually raising the temperature to room temperature. A 2N aqueous hydrochloric acid solution (150 mL) was added to the reaction mixture and the mixture was stirred at room temperature for 1.5 hours. The resulting precipitate was filtered, washed sequentially with water and ethyl ether, and then vacuum dried. After drying, it was recrystallized from chloroform and ethyl acetate and dried to produce Compound B-1 (84.2 g, yield 90%; MS: [M+H]$^+$=230).

2) Preparation of Compound B-2

Compound B-2 (74.6 g, yield 52%; MS: [M+H]$^+$=314) was prepared in the same manner as in the preparation of Compound A-1 or Preparation Example 1, except that Compound B-1 (84.2 g, 451.7 mmol) was used instead of (5-chloro-2-methoxyphenyl) boronic acid.

3) Preparation of Compound B-3

Compound B-3 (60.3 g, yield 85%; MS: [M+H]$^+$=300) was prepared in the same manner as in the preparation of Compound A-2, except that Compound B-2 (74.6 g, 236.4 mmol) was used instead of Compound A-1.

4) Preparation of Compound B-4

Compound B-4 (48.1 g, yield 85%; MS: [M+H]$^+$=280) was prepared in the same manner as in the preparation of Compound A-3, except, that Compound B-3 (60.3 g, 199.9 mmol) was used instead of Compound A-2.

5) Preparation of Compound B-5

Compound B-5 (40.1 g, yield 95%; MS:[M+H]$^+$=247) was prepared in the same manner as in the preparation of Compound A-4, except that Compound B-4 (48.1 g, 170.9 mmol) was used instead of Compound A-3.

PREPARATION EXAMPLE 1-3

Synthesis of Intermediate Compound C-4

1) Preparation of Compound C-1

Compound C-1 (60.1 g, yield 76%; MS: [M+H]$^+$=314) was prepared in the same manner as in the preparation of Compound A-1 of Preparation Example 1, except that (4-chloro-2-methoxyphenyl)boronic acid (51.1 g, 249.3 mmol) was used instead of (5-chloro-2-methoxyphenyl) boronic acid.

2) Preparation of Compound C-2

Compound C-2 (54.0 g, yield 94%; MS: [M+H]$^+$=300) was prepared in the same manner as in the preparation of Compound A-2, except that Compound C-1 (60.1 g, 190.4 mmol) was used instead of Compound A-1.

3) Preparation of Compound C-3

Compound C-3 (42.2 g, yield 83%; MS: [M+H]$^+$=280) was prepared in the same manner as in the preparation of Compound A-3, except that compound C-2 (54.0 g, 179.1 mmol) was used instead of Compound A-2.

4) Preparation of Compound C-4

Compound C-4 (34.1 g, yield 92%; MS: [M+H]$^+$=247) was prepared in the same manner as in the preparation of Compound A-4, except that Compound C-3 (42.2 g, 170.9 mmol) was used instead of Compound A-3.

PREPARATION EXAMPLE 1-4

Synthesis of Intermediate Compound D-4

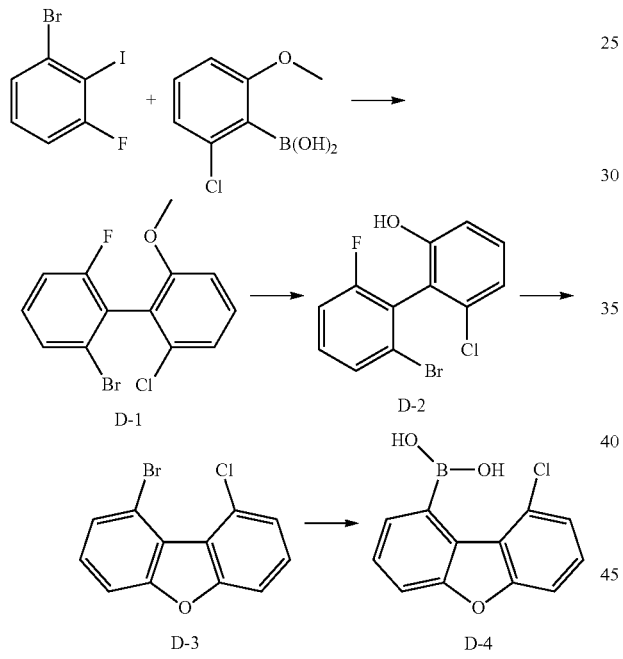

1) Preparation of Compound D-1

Compound D-1 (63.5 g, yield 81%; MS: [M+H]$^+$=314) was prepared in the same manner as in the preparation of Compound A-1 of Preparation Example 1, except that (2-chloro-6-methoxyphenyl)boronic acid (51.1 g, 249.3 mmol) was used instead of (5-chloro-2-methoxyphenyl) boronic acid.

2) Preparation of Compound D-2

Compound D-2 (55.1 g, yield 91%; MS: [M+H]$^+$=300) was prepared in the same manner as in the preparation of Compound A-2, except that Compound D-1 (63.5 g, 201.2 mmol) was used instead of Compound A-1.

3) Preparation of Compound D-3

Compound D-3 (42.0 g, yield 82%; MS: [M+H]$^+$=280) was prepared in the same manner as in the preparation of Compound A-3, except that Compound D-2 (55.1 g, 182.7 mmol) was used instead of Compound A-2.

4) Preparation of Compound D-4

Compound D-4 (35.7 g, yield 85%; MS: [M+H]$^+$=247) was prepared in the same manner as in the preparation of Compound A-4, except that Compound D-3 (42.0 g, 149.2 mmol) was used instead of Compound A-3.

PREPARATION EXAMPLE 2

Preparation Example 2-1

Synthesis of Intermediate Compound A-6

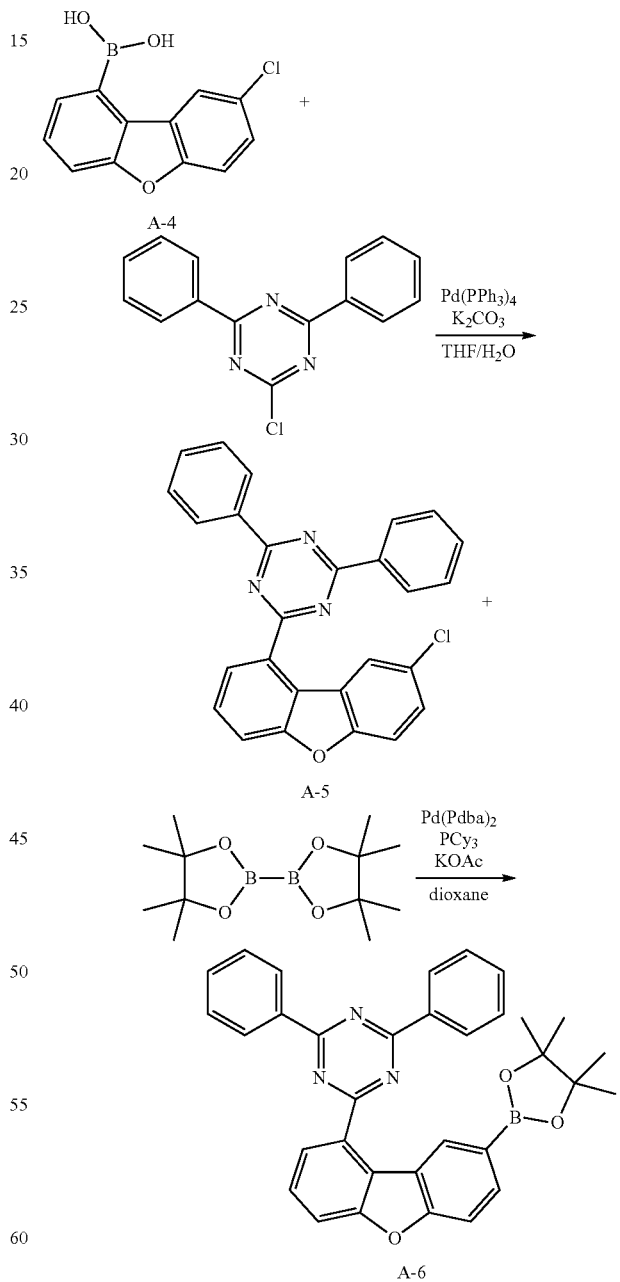

1) Preparation of Compound A-5

Compound A-4 (20.0 g, 61 mmol) and 2-chloro-4,6-diphenyltriazine (16.3 g, 61 mmol) were dissolved in 200 mL of tetrahydrofuran in a 500 mL round bottom flask under a nitrogen atmosphere. Then, a 1.5 M potassium carbonate aqueous solution (100 mL) was added and tetrakis(triphenylphosphine)palladium (0.93 g, 1.8 mmol) was added thereto, and then stirred while heating for 7 hours. The temperature of the mixture was lowered to room temperature, and the aqueous layer was separated and removed, dried over anhydrous magnesium sulfate, and concentrated under reduced pressure. The resulting material was recrystallized using a mixed solution of tetrahydrofuran and ethyl acetate and dried to produce Compound. A-5 (20.5 g, yield 78%, MS: [M+H]$^+$=434).

2) Preparation of Compound A-6

Under nitrogen atmosphere, Formula A-5 (20.5 g, 47 mmol), bis(pinacolato)diboron (13.2 g, 52 mmol) and potassium acetate (16.2 g, 165 mmol) were mixed and added to 250 ml of dioxane and heated with stirring. Bis(dibenzylideneacetone)palladium (0.81 g, 1 mmol) and tricyclohexylphosphine (0.8 g, 2 mmol) were added thereto under reflux and stirred while heating for 13 hours. After the reaction was completed, the reaction solution was cooled to room temperature and then filtered. The filtrate was poured into water, extracted with chloroform, and the organic layer was dried over anhydrous magnesium sulfate. The resulting material was distilled under reduced pressure and recrystallized from ethyl acetate to produce Compound A-6 (20.7 g, 83%).

PREPARATION EXAMPLE 2-2

Synthesis of Intermediate Compound A-8

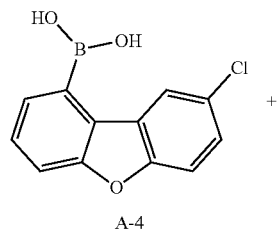

A-4

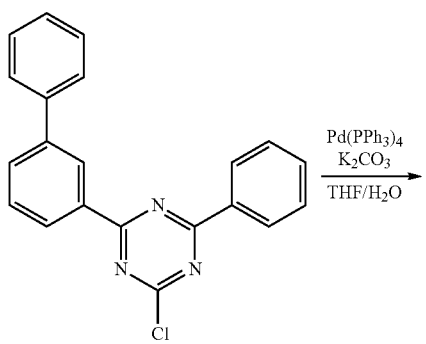

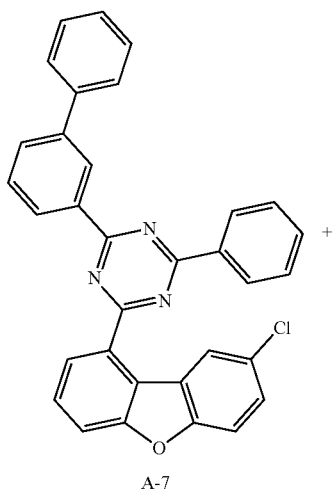

A-7

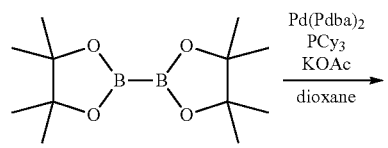

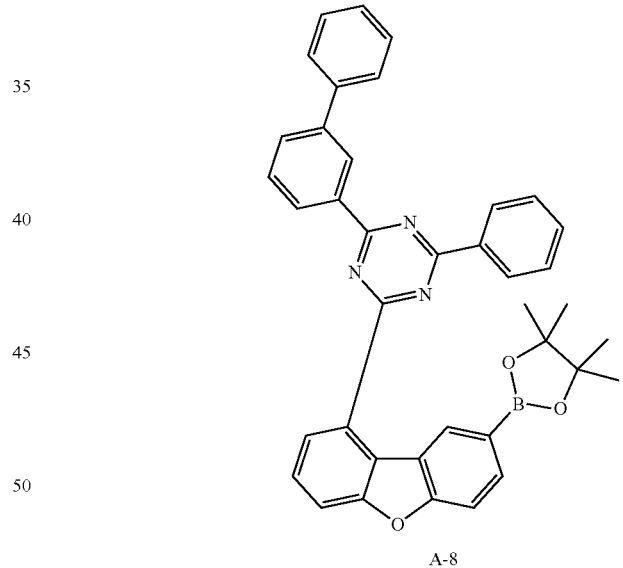

A-8

1) Preparation of Compound A-7

Compound A-7 (14.2 g, yield 68%, MS: [M+H]$^+$=510) was prepared in the same manner as in the preparation of Compound A-5, except that 2-([1,1'-biphenyl]-3-yl)-4-chloro-6-phenyl-1,3,5-triazine was used instead of 2-chloro-4,6-diphenyltriazine.

2) Preparation of Compound A-8

Compound A-8 (13.9 g, yield 82%, MS: [M+H]$^+$=602) was prepared in the same manner as in the preparation of Compound A-6, except that Compound A-7 was used instead of Compound A-5.

PREPARATION EXAMPLE 3-1

Synthesis of Intermediate Compound B-7

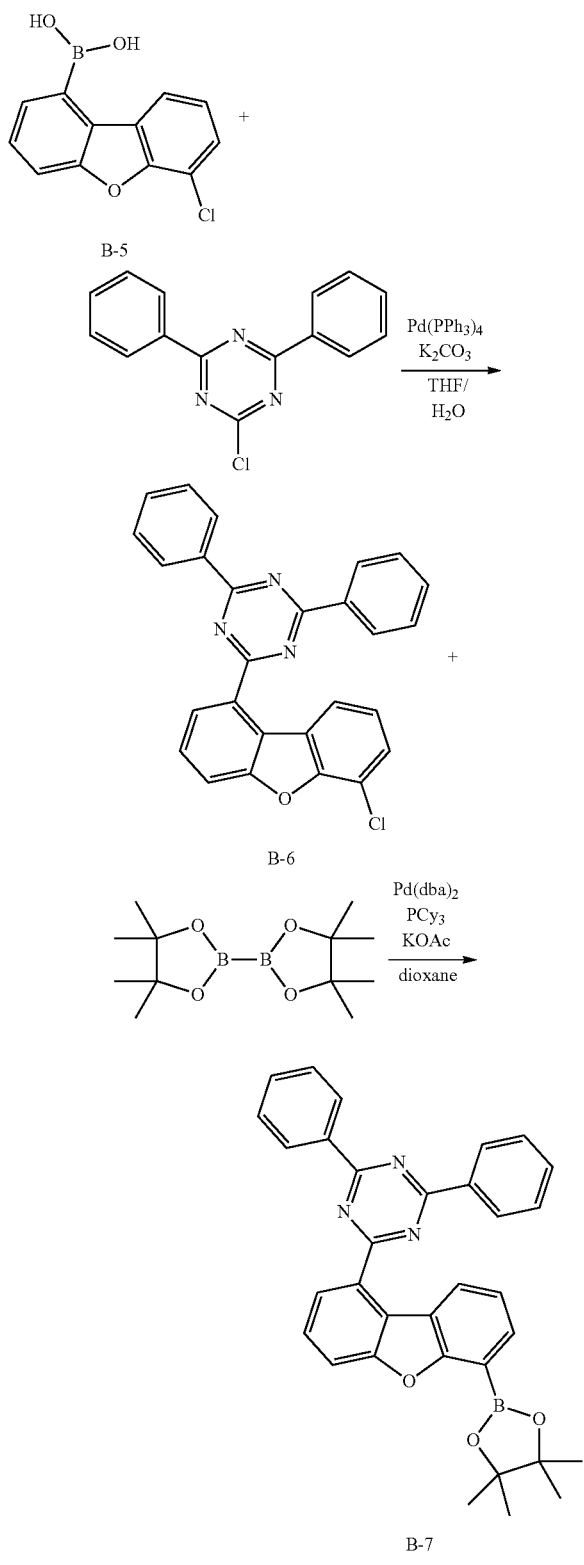

1) Preparation of Compound B-6

Compound B-6 (14.2 g, yield 82%, MS: [M+H]$^+$=434) was prepared in the same manner as in the preparation of Compound A-5, except that Compound B-5 was used instead of Compound A-4.

2) Preparation of Compound B-7

Compound B-7 (15.0 g, yield 82%, MS: [M+H]$^+$=526) was prepared in the same manner as in the preparation of Compound A-6, except that Compound B-6 was used instead of Compound A-5.

PREPARATION EXAMPLE 3-2

Synthesis of Intermediate Compound B-9

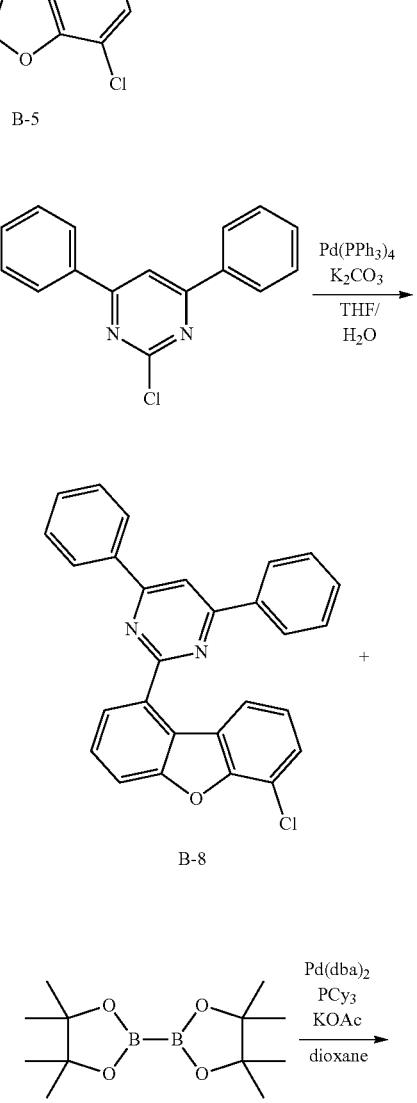

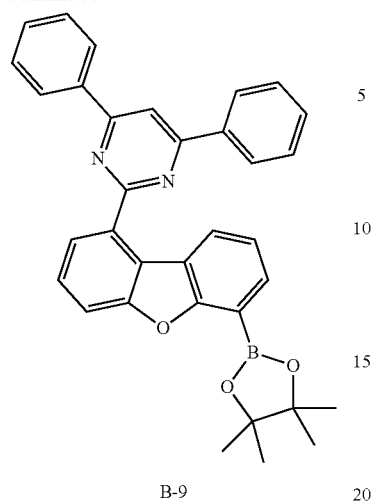

B-9

1) Preparation of Compound B-8

Compound B-8 (13.4 g, yield 76%, MS: $[M+H]^+=433$) was prepared in the same manner as in the preparation of Compound A-5, except that Compound B-5 and 2-chloro-4,6-diphenylpyrimidine were used instead of Compound A-4 and 2-chloro-4,6-diphenyltriazine.

2) Preparation of Compound B-9

Compound B-9 (10.4 g, yield 64%, MS: $[M+H]^+=525$) was prepared in the same manner as in the preparation of Compound A-6, except that Compound B-8 was used instead of Compound A-5.

PREPARATION EXAMPLE 4-1

Synthesis of Intermediate Compound C-6

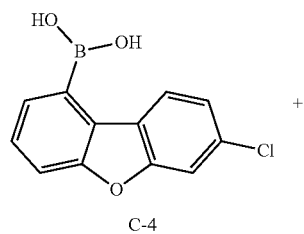

C-4

+

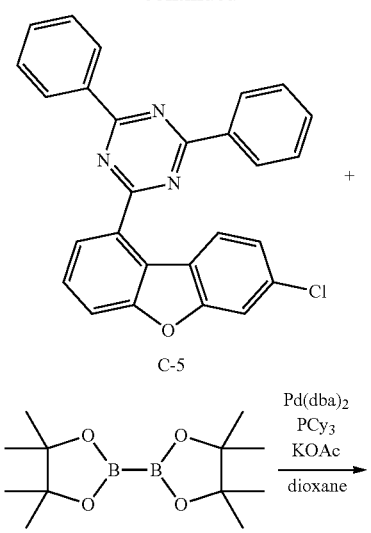

C-5

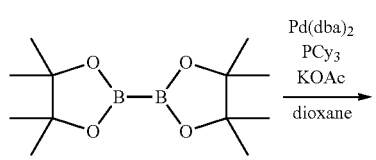

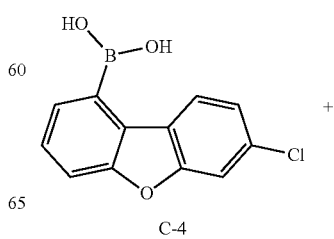

C-6

1) Preparation of Compound C-5

Compound C-5 (13.0 g, yield 77%, MS: $[M+H]^+=434$) was prepared in the same manner as in the preparation of Compound A-5, except that Compound C-4 was used instead of Compound A-4.

2) Preparation of Compound C-6

Compound C-6 (12.8 g, yield 82%, MS: $[M+H]^+=526$) was prepared in the same manner as in the preparation of Compound A-6, except that Compound C-5 was used instead of Compound A-5.

PREPARATION EXAMPLE 4-2

Synthesis of Intermediate Compound C-9

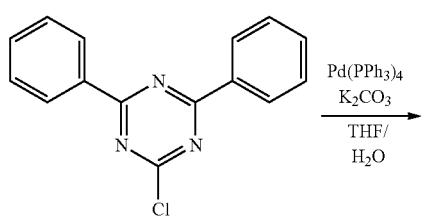

+

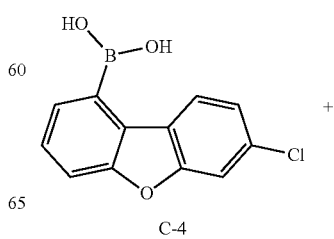

C-4

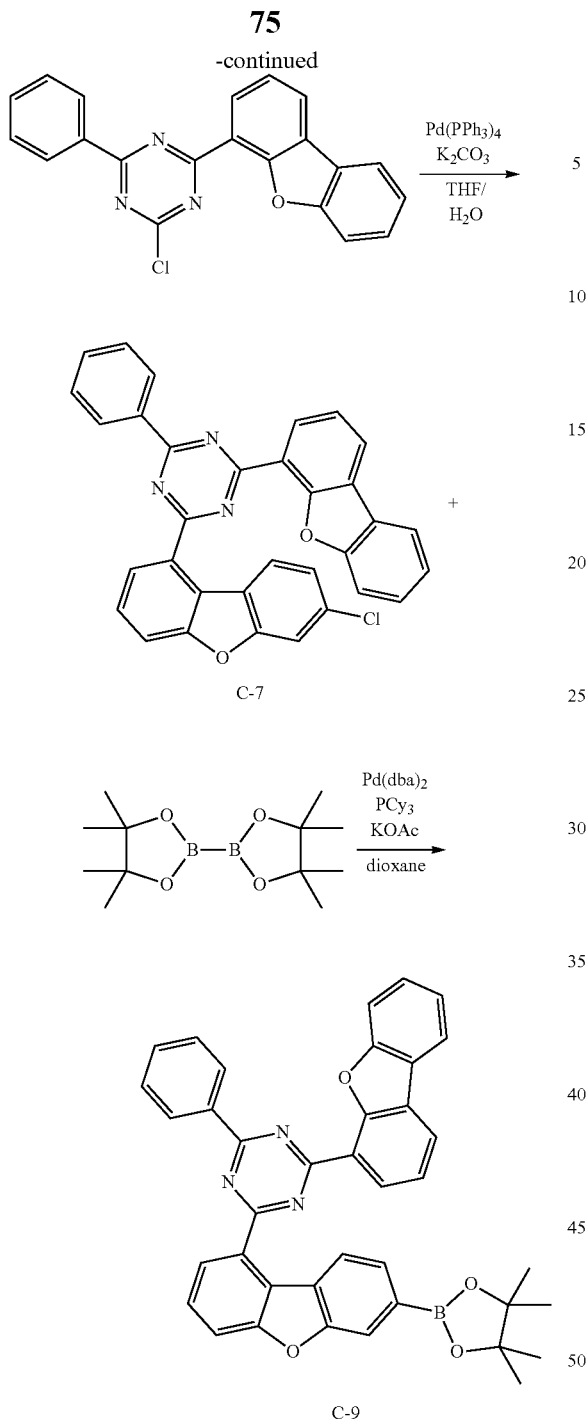

1) Preparation of Compound C-7

Compound C-7 (12.1 g, yield 56%, MS: [M+H]⁺=524) was prepared in the same manner as in the preparation of Compound A-5, except that Compound C-4 and 2-chloro-4-(dibenzofuran-4-yl)-6-phenyl-1,3,5-triazine were used instead of Compound A-4 and 2-chloro-4,6-diphenyltriazine.

2) Preparation of Compound C-9

Compound C-9 (12.5 g, yield 73%, MS: [M+H]⁺=616 was prepared in the same manner as in the preparation of Compound A-6, except that Compound C-7 was used instead of Compound A-5.

PREPARATION EXAMPLE 5-1

Synthesis of Intermediate Compound D-6

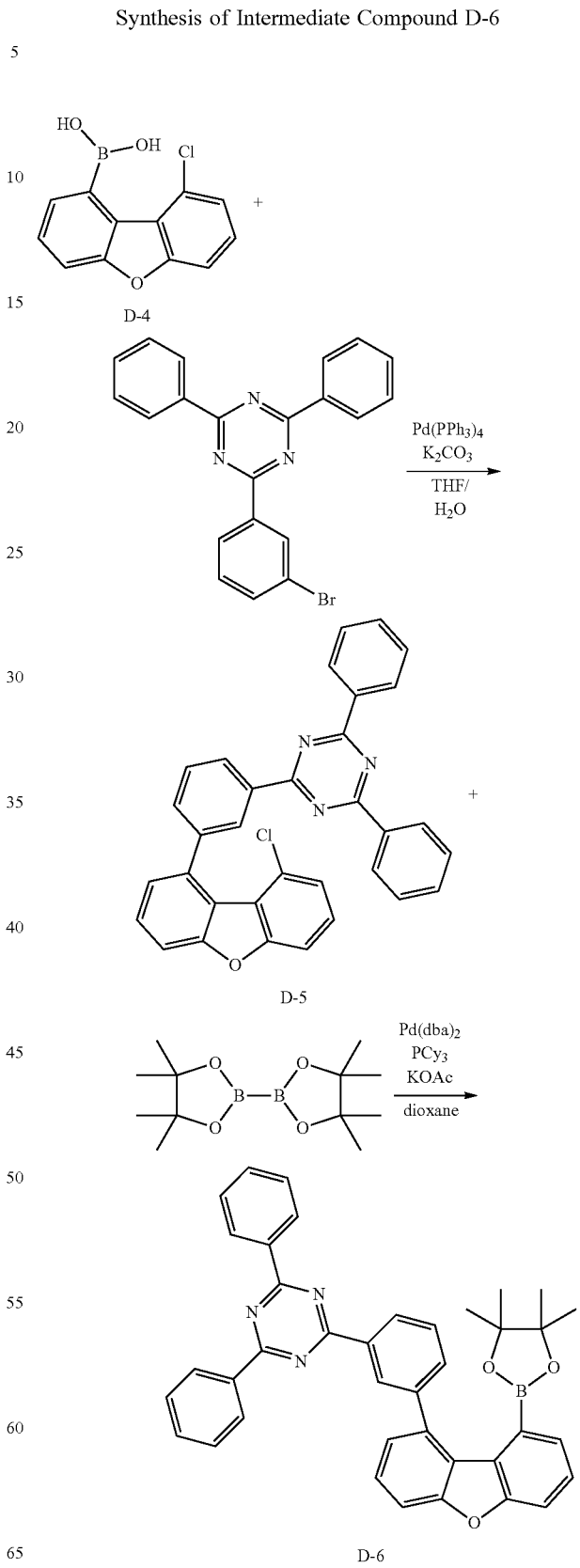

1) Preparation of Compound D-5

Compound D-5 (13.0 g, yield 74%, MS: [M+H]⁺=434) was prepared in the same manner as in the preparation of Compound A-5, except that Compound D-4 was used instead of Compound A-4.

2) Preparation of Compound D-6

Compound D-6 (9.5 g, yield 60%, MS: [M+H]⁺=526) was prepared in the same manner as in the preparation of Compound A-6, except that Compound D-5 was used instead of Compound A-5.

EXAMPLE

Example 1

Preparation of Compound 1

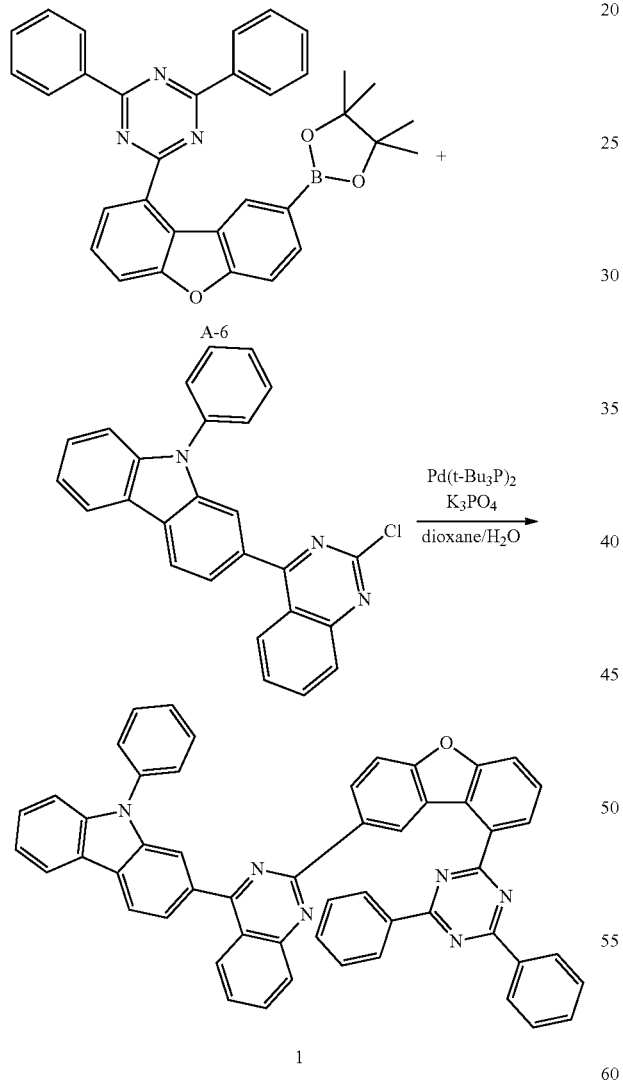

After Compound A-6 (10.0 g, 19 mmol) and 2-(2-chloroquinazolin-4-yl) 9-phenyl-9H-carbazole (7.8 g, 19 mmol) were dissolved in 130 ml of dioxane, K₃PO₄ (12.1 g, 57 mmol) was added and bis(tri-tert-butylphosphine)palladium (0) (0.09 g, 0.2 mmol) was added thereto, and then stirred while heating for 15 hours. The temperature of the mixture was lowered to room temperature and filtered. The filtrate was extracted with chloroform and water, and then the organic layer was dried with magnesium sulfate. After that, the organic layer was distilled under reduced pressure, and recrystallized using a mixed solution of tetrahydrofuran and ethyl acetate and dried to produce Compound 1 (9.2 g, 63%, MS: [M+H]⁺=769).

Example 2

Preparation of Compound 2

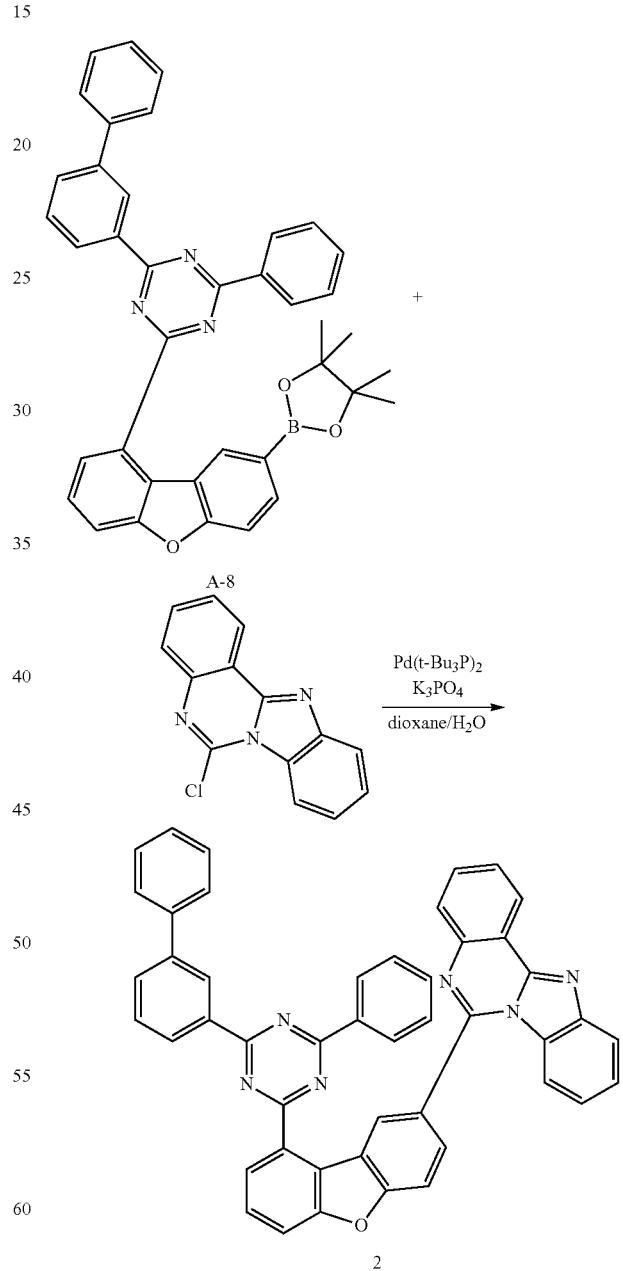

Compound 2 (7.7 g, yield 67%, MS: [M+H]⁺=693) was prepared in the same manner as in the preparation of Compound 1 of Example 1, except that Compound A-8 and 6-chlorobenzo[4,5]imidazo[1,2-c]quinazoline were used instead of Compound A-6 and 2-(2-chloroquinazolin-4-yl)9-phenyl-9H-carbazole.

Example 3

Preparation of Compound 3

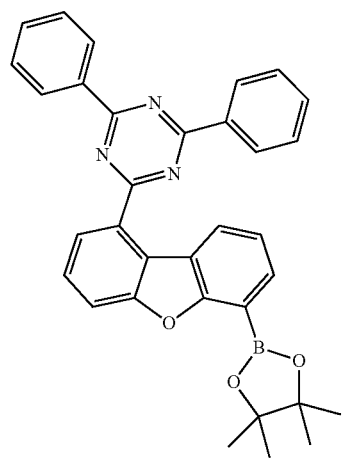

B-7

+

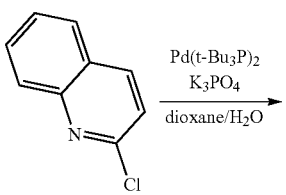

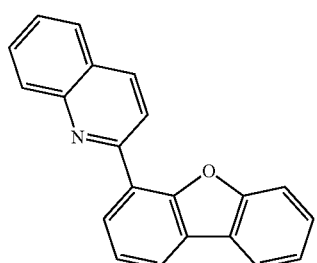

3

Compound 3 (4.3 g, yield 53%, MS: [M+H]$^+$=527) was prepared in the same manner as in the preparation of Compound 1 of Example 1, except that Compound B-7 and 2-chloroquinoline were used instead of Compound A-6 and 2-(2-chloroquinazolin-4-yl)9-phenyl-9H-carbazole.

Example 4

Preparation of Compound 4

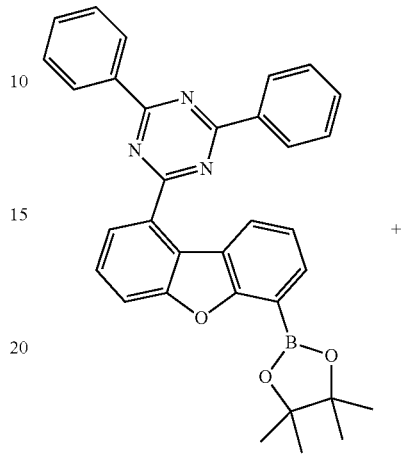

B-7

+

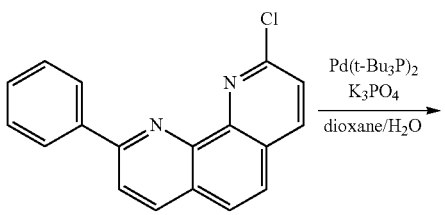

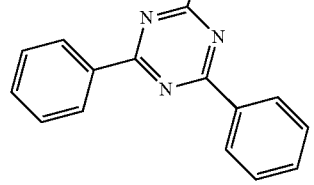

4

Compound 4 (6.0 g, yield 48%, MS: [M+H]$^+$=634) was prepared in the same manner as in the preparation of Compound 1 of Example 1, except that Compound B-7 and 2-chloro-9-phenyl-1,10-phenanthroline were used instead of Compound A-6 and 2-(2-chloroquinazolin-4-yl)9-phenyl-9H-carbazole.

Example 5

Preparation of Compound 5

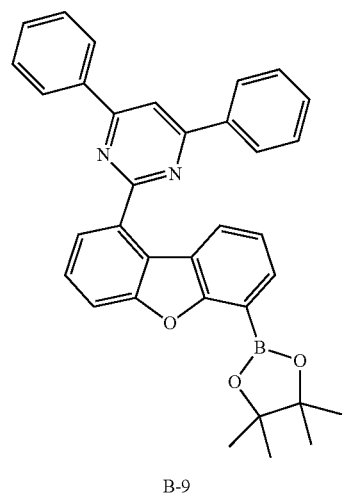

B-9

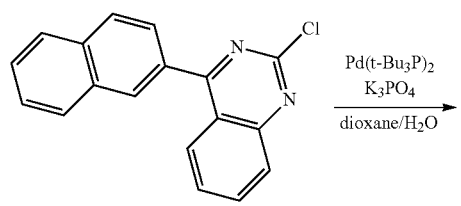

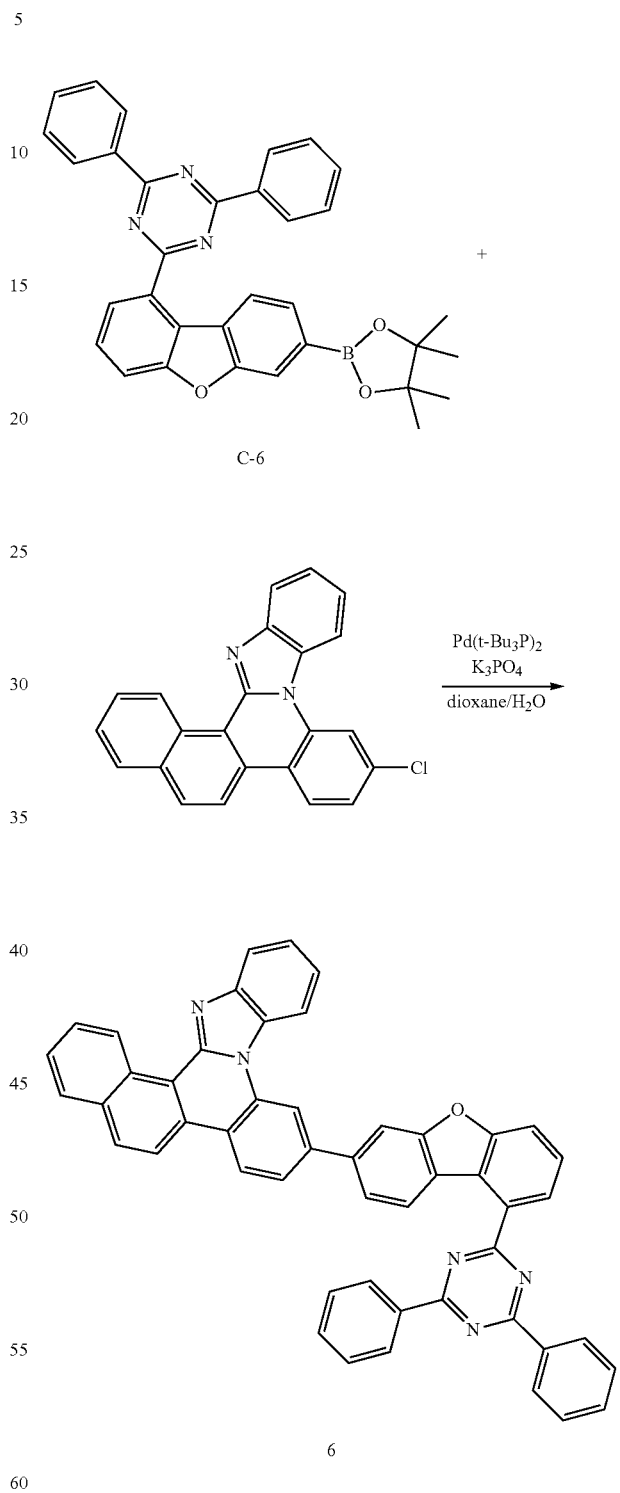

Compound 5 (6.2 g, yield 54%, MS: [M+H]$^+$=653) was prepared in the same manner as in the preparation of Compound 1 of Example 1, except that Compound B-9 and 2-chloro-4-(naphthalen-2-yl)quinazoline were used instead of Compound A-6 and 2-(2-chloroquinazolin-4-yl)9-phenyl-9H-carbazole.

Example 6

Preparation of Compound 6

Compound 6 (7.4 g, yield 54%, MS: [M+H]$^+$=716) was prepared in the same manner as in the preparation of Compound 1 of Example 1, except that Compound C-6 and 9-chlorobenzo[i]benzo[4,5]imidazo[1,2-f]phenanthrdine were used instead of Compound A-6 and 2-(2-chloroquinazolin-4-yl)9-phenyl-9H-carbazole.

Example 7

Preparation of Compound 7

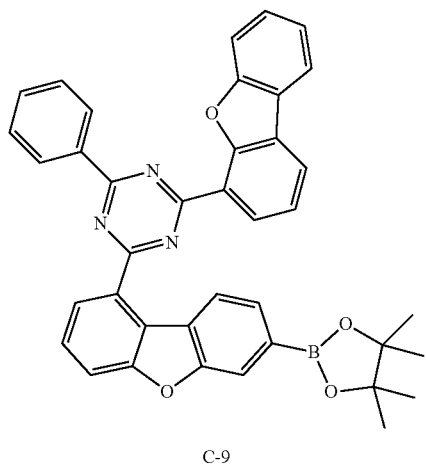

C-9

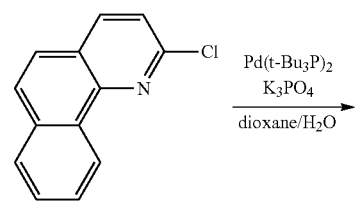

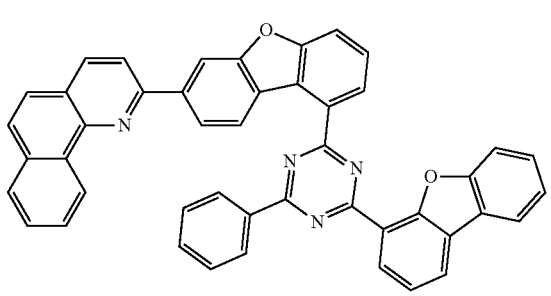

7

Compound 7 (5.1 g, yield 47%, MS: [M+H]$^+$=667) was prepared in the same manner as in the preparation of Compound 1 of Example 1, except that Compound C-9 and 2-chlorobenzo[h]quinoline were used instead of Compound A-6 and 2-(2-chloroquinazolin-4-yl)9-phenyl-9H-carbazole.

Example 8

Preparation of Compound 8

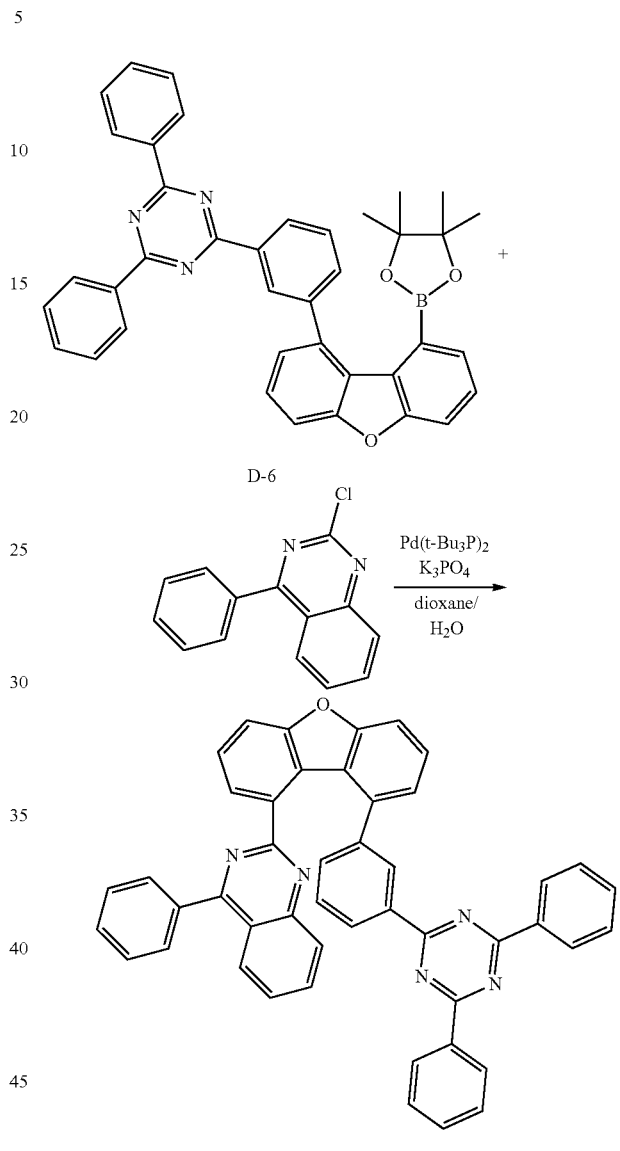

8

Compound 8 (6.0 g, yield 53%, MS: [M+H]$^+$=680) was prepared in the same manner as in the preparation of Compound 1 of Example 1, except that Compound D-6 and 2-chloro-4-phenylquinazoline were used instead Compound A-6 and 2-(2-chloroquinazolin-4-yl)9-phenyl-9H-carbazole.

EXPERIMENTAL EXAMPLES

Experimental Example 1

A glass substrate on which a thin film of ITO (indium tin oxide) was coated at a thickness of 1300 Å was put into distilled water containing a detergent dissolved therein and washed by ultrasonic waves. In this case, the detergent used was a product commercially available from Fisher Co., and the distilled water was one which had been filtered twice by using a filter that is commercially available from Millipore Co. The ITO was washed for 30 minutes, and ultrasonic washing was then repeated twice for 10 minutes by using distilled water. After the washing with distilled water was completed, the substrate was ultrasonically washed with a solvent of isopropyl alcohol, acetone, and methanol, and dried, after which it was transported to a plasma cleaner. Then, the substrate was cleaned with oxygen plasma for 5 minutes, and then transferred to a vacuum evaporator.

On the ITO transparent electrode thus prepared, a hexanitrile hexaazatriphenylene (HAT) compound below was thermally vacuum-deposited to a thickness of 50 Å to form a hole injection layer. 4,4'-[bis-(1-naphthyl)-N-phenylamino] biphenyl (NPB; HT-1) as a hole transport material was thermally vacuum-deposited thereon to a thickness of 250 Å to form a hole transport layer, and a compound of Formula HT-2 below was vacuum-deposited on the HT-1 deposited film to a thickness of 50 Å to form an electron blocking layer. Then, Compound 2 prepared as a host, a compound of Formula YGH-1 below, and a phosphorescent dopant of Formula YGD-1 below were co-deposited on the HT-2 deposited film at a weight ratio of 44:44:12 to form the light-emitting layer having a thickness of 400 Å. A material of Formula ET-1 below was vacuum-deposited on the light-emitting layer to a thickness of 250 Å, and additionally a material of Formula ET-2 below was co-deposited with 2 wt % Li to a thickness of 100 Å to form an electron transport layer and an electron injection layer. Aluminum was evaporated to a thickness of 1000 Å on the electron injection layer to form a cathode.

In the above process, the vapor deposition rate of the organic material was maintained at 0.4 to 0.7 Å/s, the vapor deposition rate of aluminum was maintained at 2 Å/s, and the degree of vacuum during vapor deposition was maintained at $1\times10^{-7}$ to $5\times10^{-8}$ torr to manufacture an organic light emitting device.

HAT

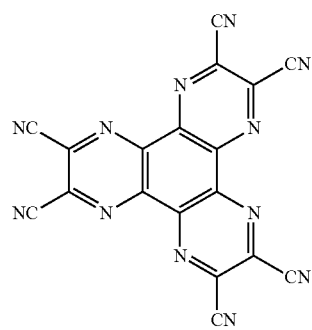

HT-1

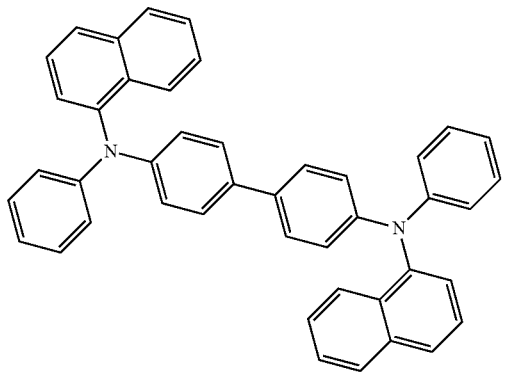

-continued

HT-2

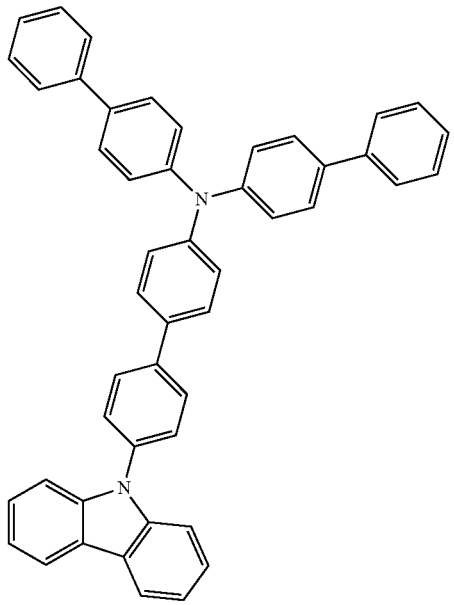

YGH-1

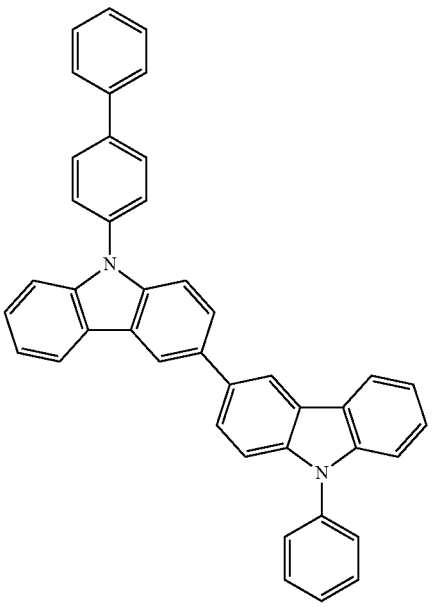

YGD-1

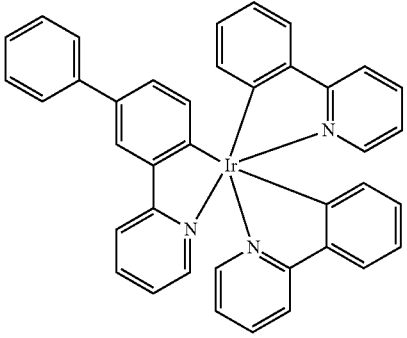

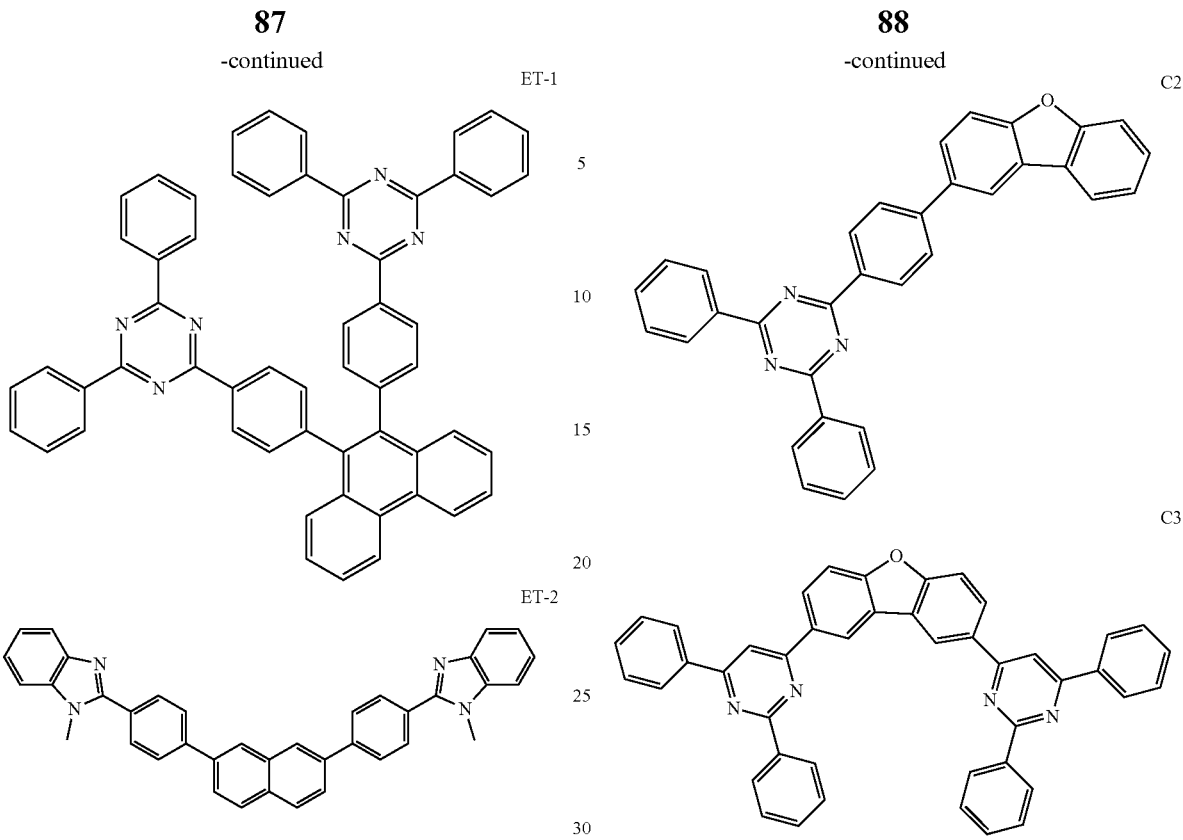

Experimental Examples 2 to 9

The organic light emitting device was manufactured in the same manner as in Experimental Example 1, except that the compounds shown in Table 1 below were used instead of Compound 2 as a phosphorescent host during the formulation of the light emitting layer in Experimental Example 1.

Comparative Examples 1 to 3

The organic light emitting devices of Comparative Examples 1 to 3 were respectively manufactured in the same manner as in Experimental Example 1, except that Compounds C1 to C3 shown in Table 1 below were used instead of Compound 2 as a host during the formulation of the light emitting layer.

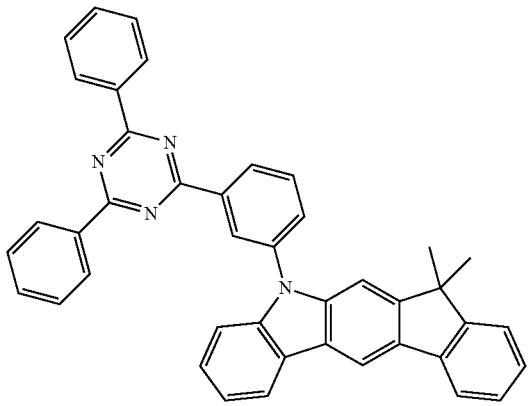

The voltage, efficiency, color coordinates, and lifetime were measured by applying a current to the organic light emitting devices manufactured in Experimental Examples 1 to 9 and Comparative Examples 1 to 3, and the results are shown in Table 1 below. T95 means the time required for the luminance to be reduced to 95% of the initial luminance.

TABLE 1

| Category | Compound | Voltage (V) (@10 mA/cm$^2$) | Efficiency (Cd/A) (@10 mA/cm$^2$) | Color coordinates (x, y) | Lifetime (h) (LT$_{95}$ at 50 mA/cm$^2$) |
|---|---|---|---|---|---|
| Experimental Example 1 | Compound 1 | 3.5 | 80 | 0.46, 0.52 | 105 |
| Experimental Example 2 | Compound 2 | 3.4 | 74 | 0.45, 0.54 | 120 |
| Experimental Example 3 | Compound 5 | 3.6 | 79 | 0.45, 0.53 | 110 |
| Experimental Example 4 | Compound 6 | 3.6 | 76 | 0.46, 0.53 | 120 |
| Experimental Example 5 | Compound 8 | 3.7 | 78 | 0.46, 0.52 | 100 |
| Comparative Experimental Example 1 | C1 | 3.6 | 68 | 0.45, 0.54 | 91 |
| Comparative Experimental Example 2 | C2 | 4.0 | 60 | 0.46, 0.53 | 61 |
| Comparative Experimental Example 3 | C3 | 4.2 | 60 | 0.45, 0.53 | 65 |

As shown in Table 1, it can be confirmed that the case of using the compounds of the present invention as a light emitting layer material exhibits superior characteristics in terms of efficiency and lifetime, as compared with the comparative experimental examples.

| Description of Item Numbers | |
|---|---|
| 1: substrate | 2: anode |
| 3: light emitting layer | 4: cathode |
| 5: hole injection layer | 6: hole transport layer |
| 7: light emitting layer | 8: electron transport layer |

The invention claimed is:

1. A compound selected from compounds of the following Formulas 2 to 5:

[Formula 2]

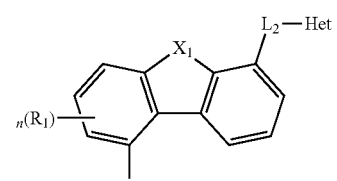

[Formula 3]

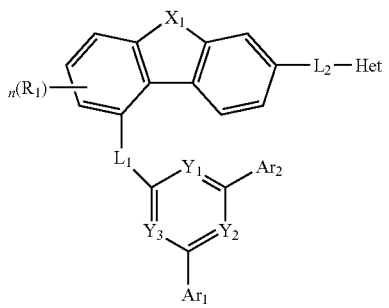

[Formula 4]

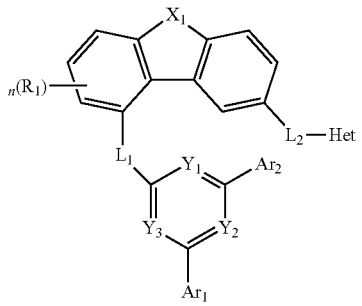

[Formula 5]

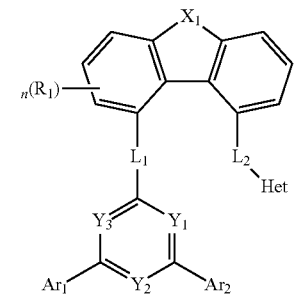

wherein in Formulas 2 to 5 above:

$X_1$ is O or S;

$R_1$ is hydrogen or a substituted or unsubstituted $C_{1-60}$ alkyl;

$L_1$ and $L_2$ are each independently a direct bond or

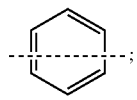

$Y_1$, $Y_2$, and $Y_3$ are each independently N or $CR_2$, provided that at least one of $Y_1$, $Y_2$, and $Y_3$ is N;

$R_2$ is hydrogen or a substituted or unsubstituted $C_{1-60}$ alkyl;

$Ar_1$ and $Ar_2$ are each independently a substituted or unsubstituted $C_{6-60}$ aryl or a substituted or unsubstituted $C_{5-60}$ heteroaryl containing at least one of N, O, and S;

n is 1 or 2; and

Het is any one substituent selected from the group consisting of the following formulas:

[1-1]

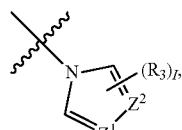

[1-2]

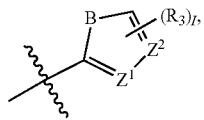

[1-7]

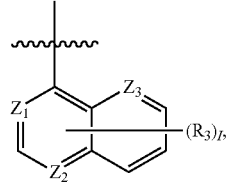

[1-8]

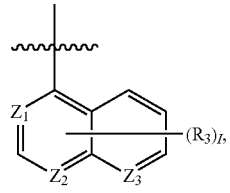

[1-9]

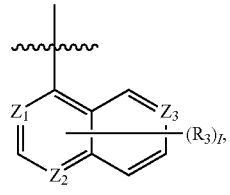

[1-10]

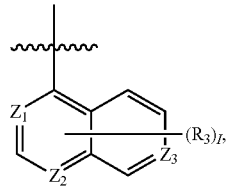

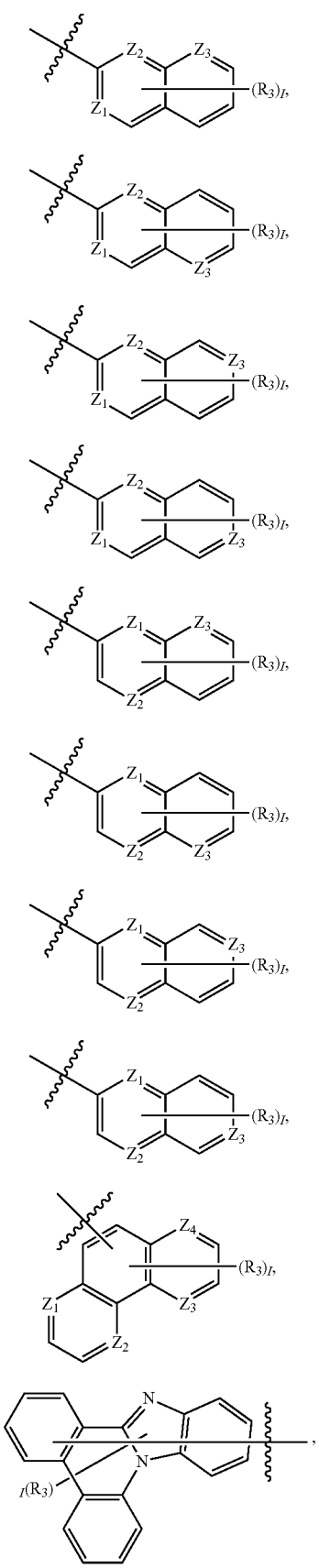

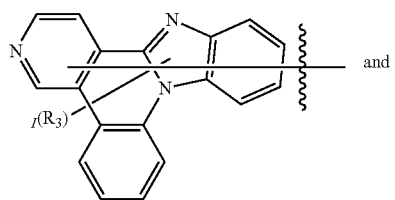

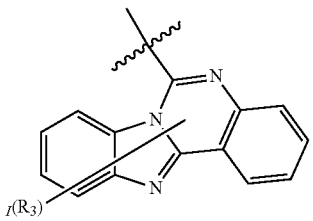

B is O or S;

in Formulas [1-1] and [1-2], $Z_1$, $Z_2$, $Z_3$, and $Z_4$ are each independently N or CH, provided that at least one of $Z_1$, $Z_2$, $Z_3$, and $Z_4$ in each formula is N, in Formulas [1-7] to [1-18], $Z_1$, $Z_2$ and $Z_3$ are N, and in Formula [1-19], $Z_1$, $Z_2$, $Z_3$, and $Z_4$ are each independently N or CH, provided that one of $Z_1$, $Z_2$, $Z_3$, and $Z_4$ is N;

l is independently 1 or 2, and wherein each $R_3$ in Formulas [1-1], [1-2] and [1-7] to [1-22] is independently hydrogen, a substituted or unsubstituted $C_{1-60}$ alkyl, a substituted or unsubstituted $C_{6-60}$ aryl, or a substituted or unsubstituted $C_{5-60}$ heteroaryl containing at least one of N, O, and S.

2. The compound of claim 1, wherein in Formulas 2, 3 and 5, Het is any one substituent selected from the group consisting of the following formulas:

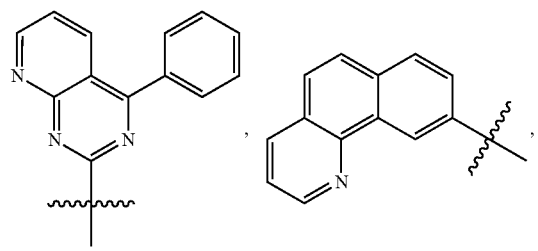

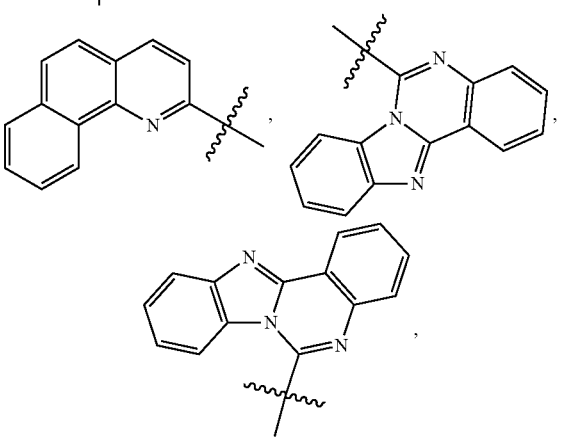

-continued

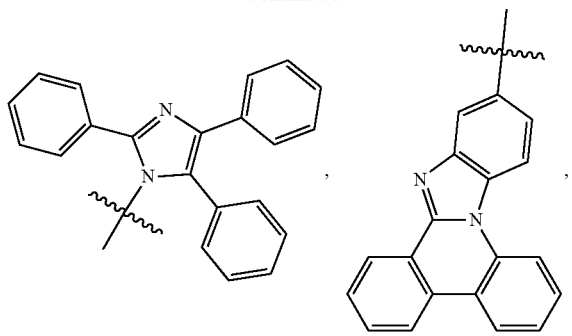

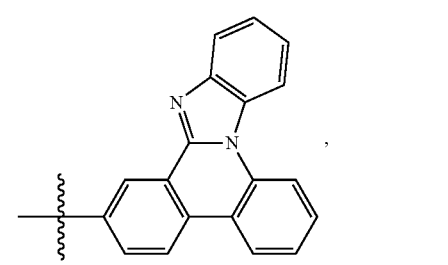

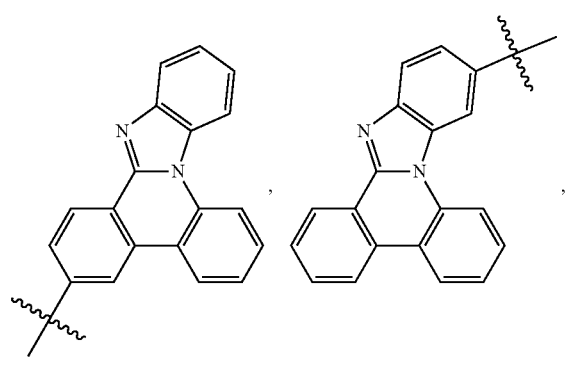

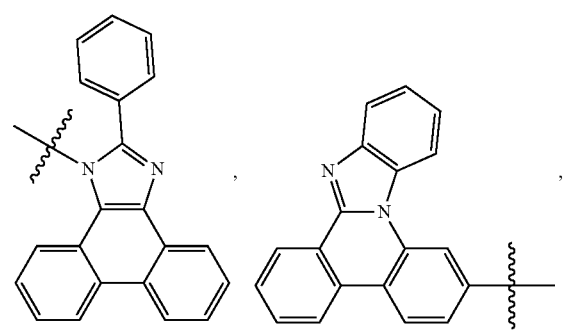

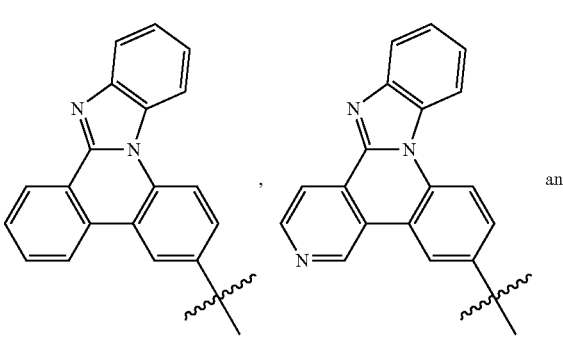

-continued

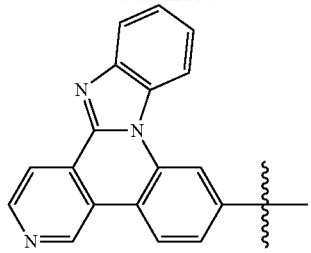

3. The compound of claim 1, wherein the substituent of

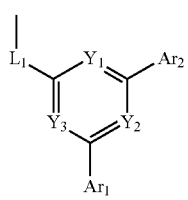

in Formulas 2 to 5 is any one substituent selected from the group consisting of the following formulas:

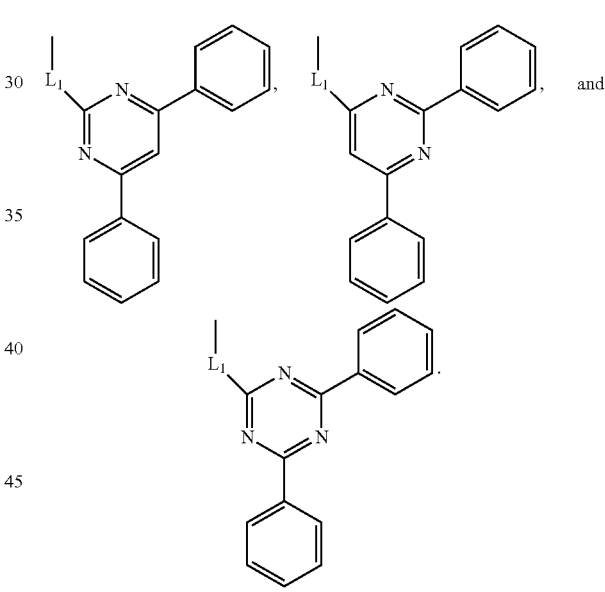

4. The compound of claim 1, wherein $R_1$ is hydrogen or a substituted or unsubstituted $C_{1-10}$ alkyl.

5. The compound of claim 1 wherein in Formulas 2, 3 and 5, $R_3$ is hydrogen or any one substituent selected from the group consisting of the following formulas:

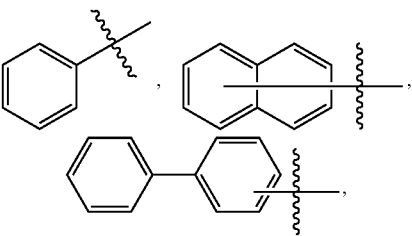

-continued
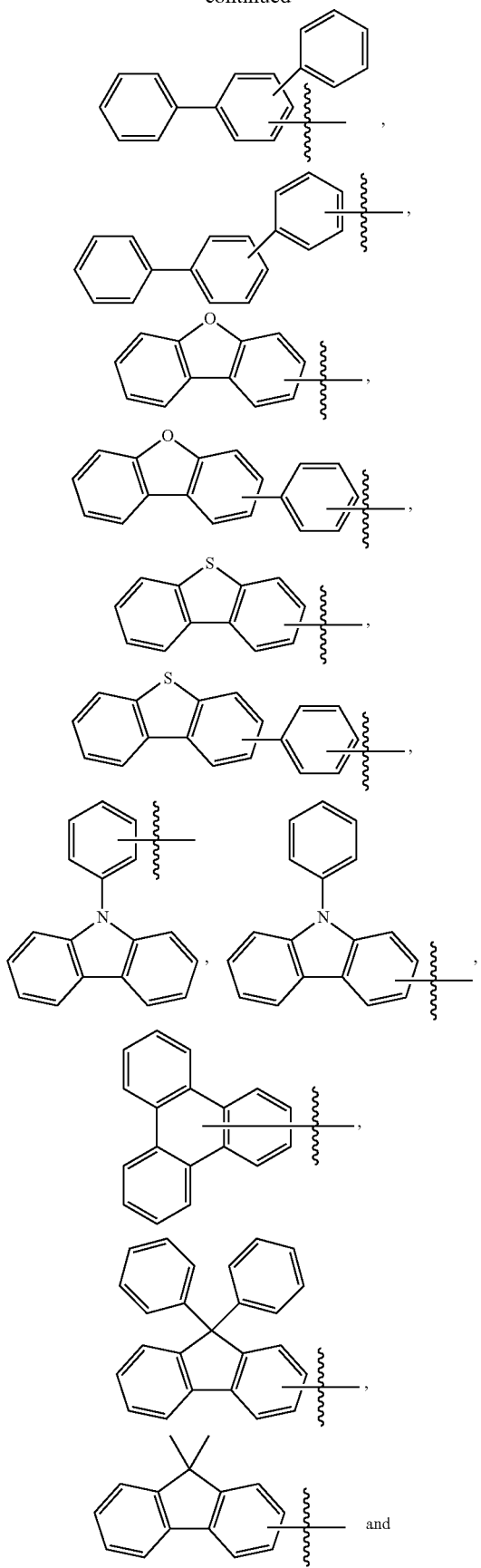
-continued
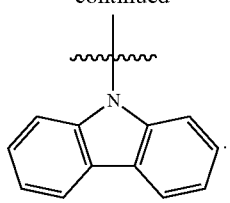
6. The compound of claim 1, wherein the compound of Formulas 2 to 5 is any one compound selected from the group consisting of compounds of the following formulas:
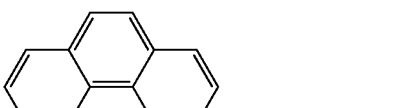
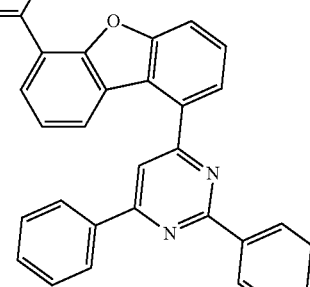
,
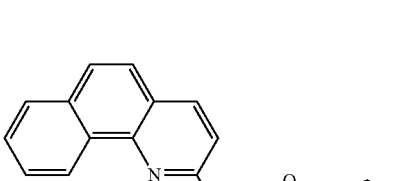
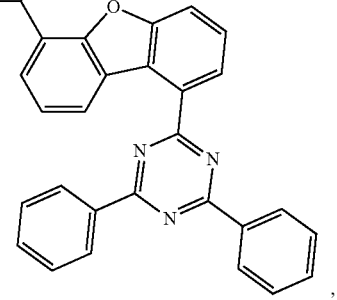
,
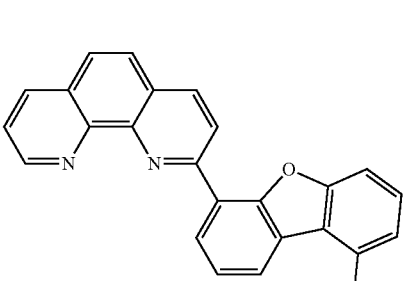
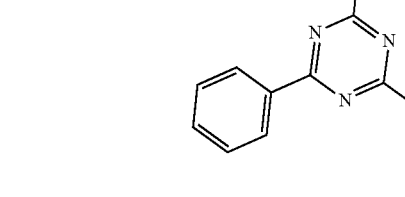
, 97
-continued
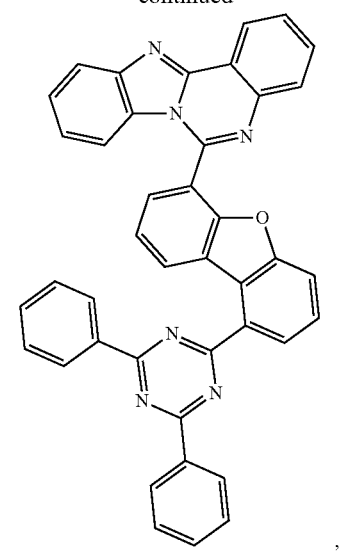
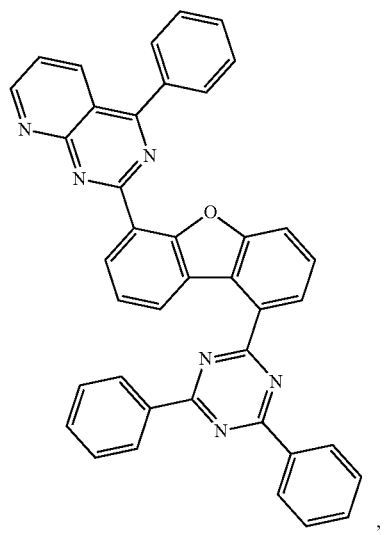
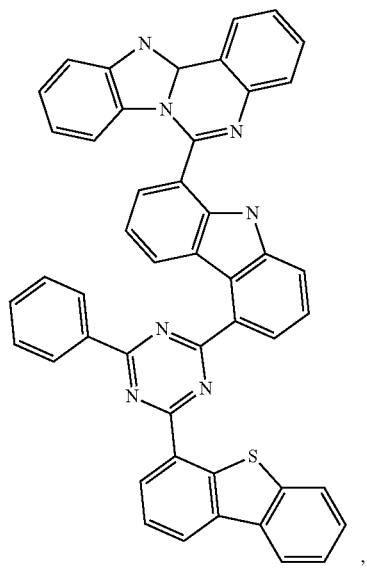
98
-continued
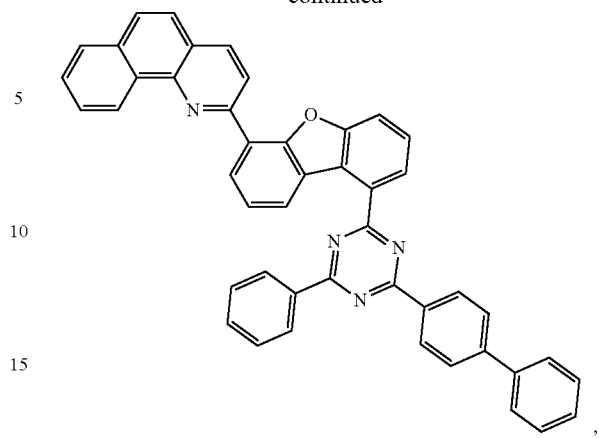
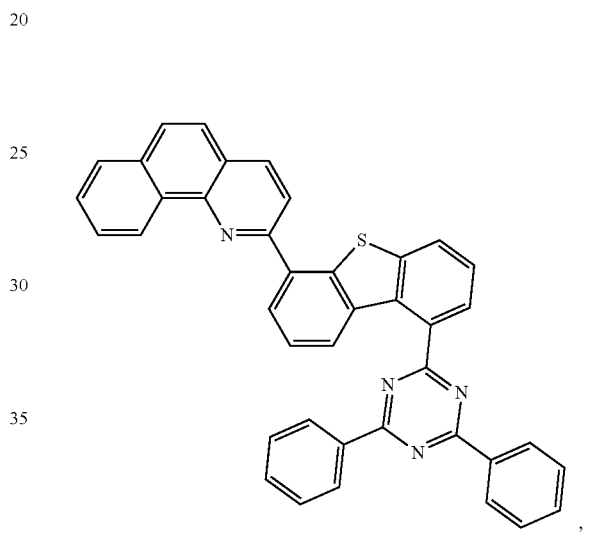
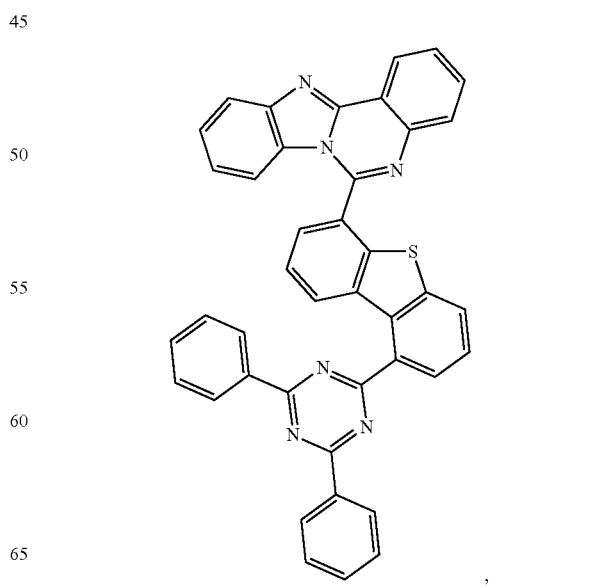

99
-continued
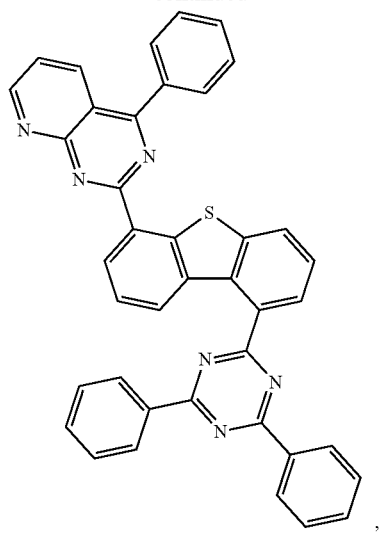
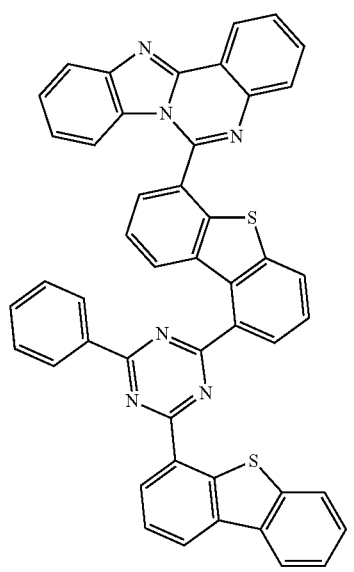
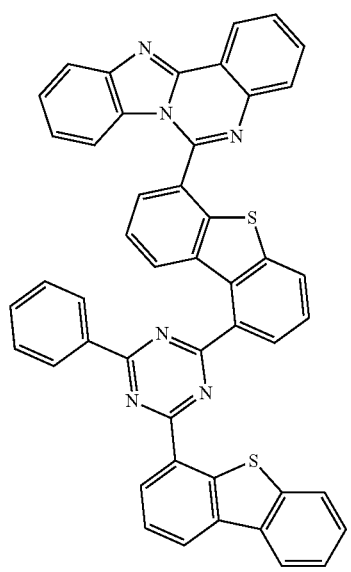
100
-continued
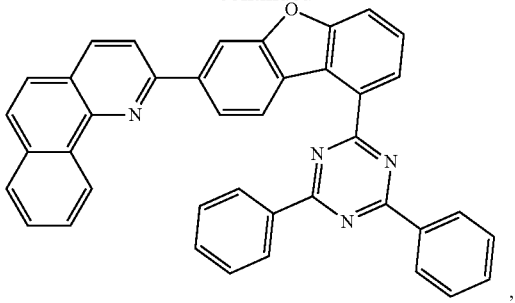
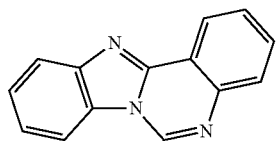
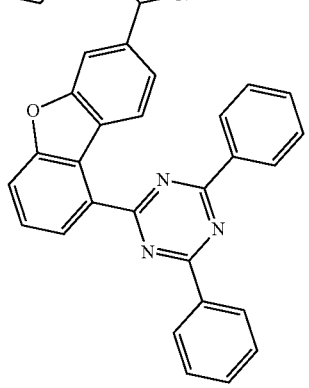
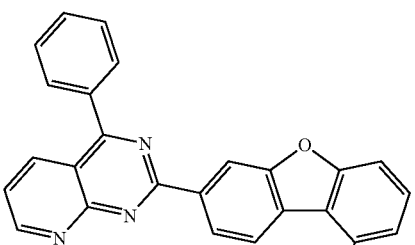
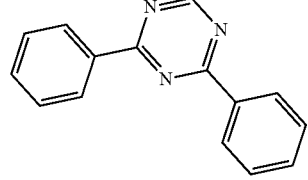
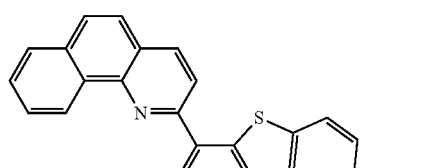
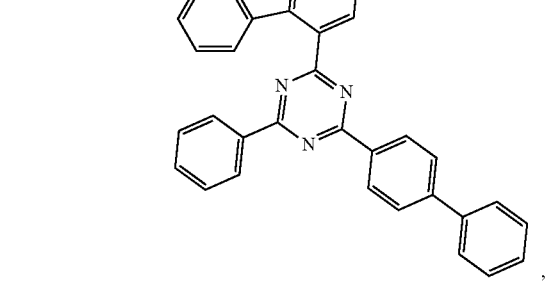
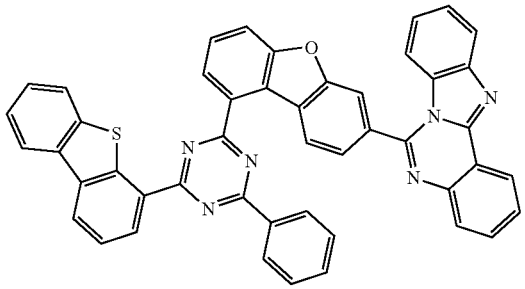

101
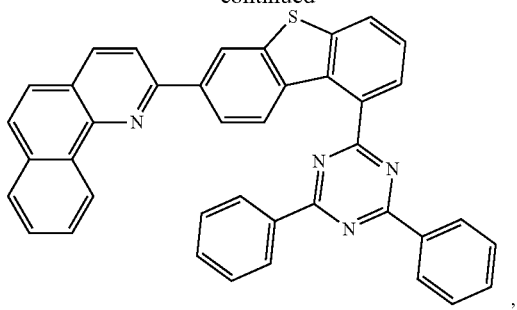
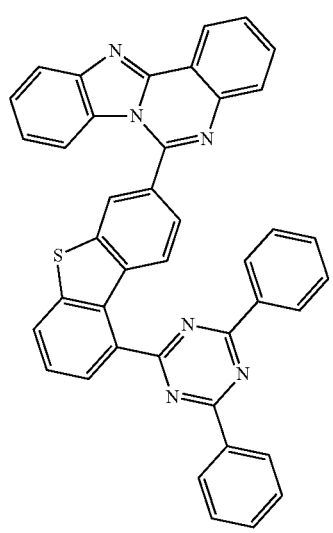
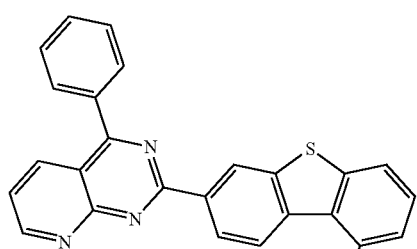
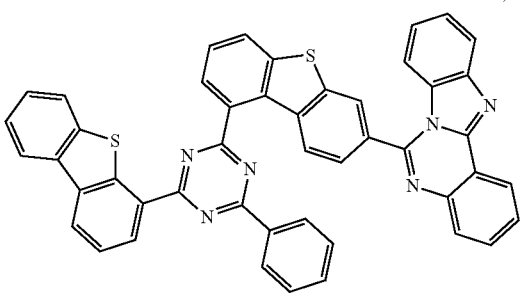
102
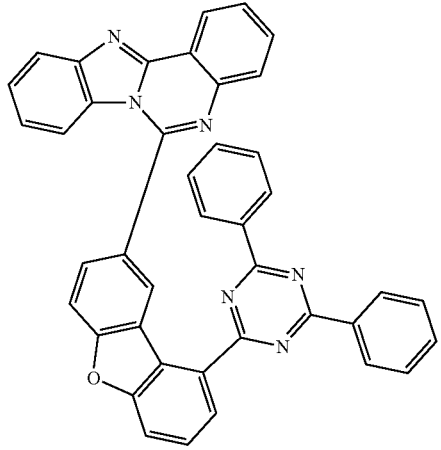
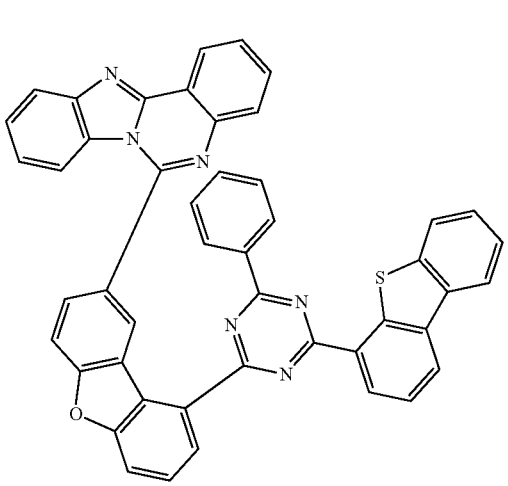
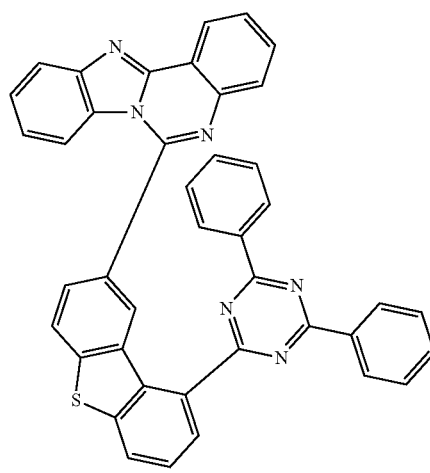

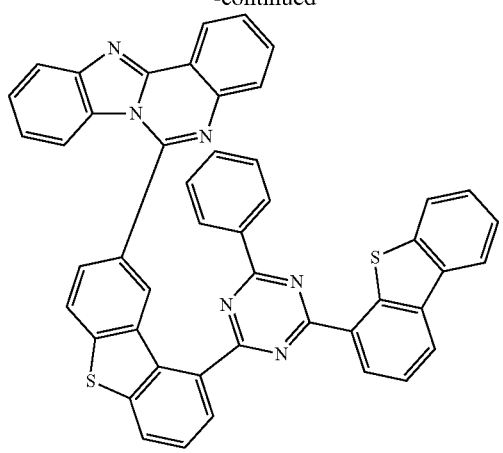

,

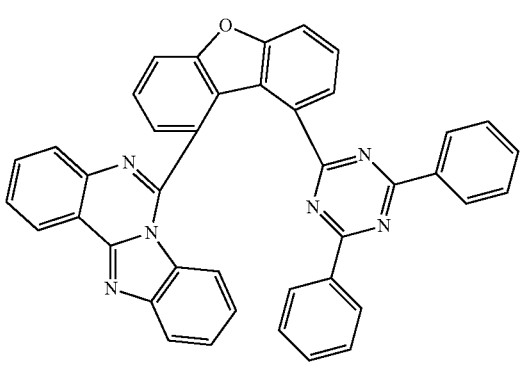

,

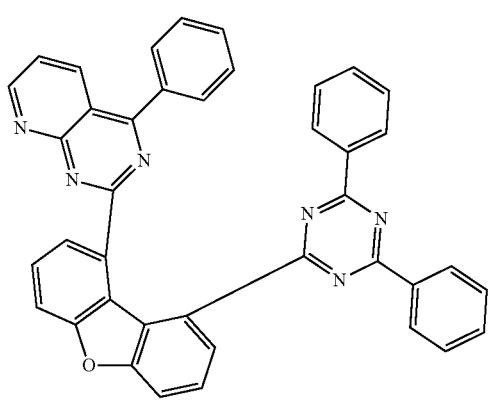

,

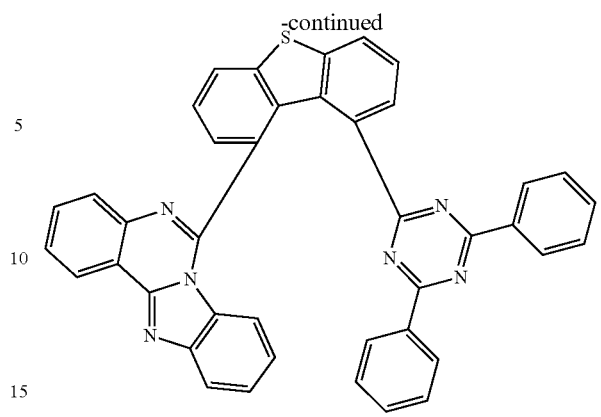

and

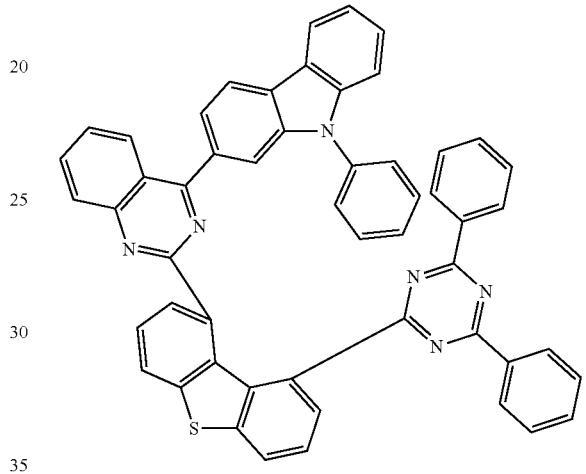

.

7. An organic light emitting device comprising:
a first electrode:
a second electrode provided at a side opposite to the first electrode; and
at least one organic material layer provided between the first electrode and the second electrode,
wherein the at east one organic material layer comprises the compound of claim 1.

8. The organic light emitting device of claim 7, wherein the organic material layer comprising said compound is a light emitting layer.

9. The organic light emitting device of claim 8, wherein the compound is a host material in the light emitting layer.

10. The organic light emitting device of claim 9, wherein the light emitting layer further comprises a dopant material.

11. The organic light emitting device of claim 7, wherein the organic material layer is an electron injection layer, an electron transport layer, or a layer simultaneously performing electron injection and electron transport.

* * * * *